(12) United States Patent
Shih et al.

(10) Patent No.: US 11,634,464 B2
(45) Date of Patent: Apr. 25, 2023

(54) RECOMBINANT POLYPEPTIDES DERIVED FROM FBP1 AND FBP2 AND USES OF THE SAME

(71) Applicant: CHANG GUNG UNIVERSITY, Taoyuan (TW)

(72) Inventors: Shin-Ru Shih, New Taipei (TW); Yu-An Kung, Taoyuan (TW); Chuan-Tien Hung, Taichung (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 282 days.

(21) Appl. No.: 16/908,179

(22) Filed: Jun. 22, 2020

(65) Prior Publication Data

US 2020/0317739 A1  Oct. 8, 2020

Related U.S. Application Data

(62) Division of application No. 15/956,478, filed on Apr. 18, 2018, now Pat. No. 10,730,920.

(30) Foreign Application Priority Data

Apr. 19, 2017  (TW) ................. 106113165

(51) Int. Cl.

| C07K 14/47 | (2006.01) |
| C12N 15/86 | (2006.01) |
| C12N 7/00 | (2006.01) |
| A61K 39/125 | (2006.01) |
| C07K 14/005 | (2006.01) |
| A61K 39/12 | (2006.01) |
| A61K 39/00 | (2006.01) |

(52) U.S. Cl.
CPC ............ *C07K 14/47* (2013.01); *A61K 39/12* (2013.01); *A61K 39/125* (2013.01); *C07K 14/005* (2013.01); *C07K 14/4702* (2013.01); *C12N 7/00* (2013.01); *C12N 15/86* (2013.01); *A61K 2039/525* (2013.01); *C12N 2770/32022* (2013.01); *C12N 2770/32034* (2013.01); *C12N 2770/32051* (2013.01); *C12N 2770/32321* (2013.01); *C12N 2770/32322* (2013.01); *C12N 2770/32334* (2013.01); *C12N 2770/32343* (2013.01); *C12N 2770/32351* (2013.01); *C12N 2840/203* (2013.01)

(58) Field of Classification Search
None
See application file for complete search history.

(56) References Cited

PUBLICATIONS

Huang PN, Lin JY, Locker N, Kung YA, Hung CT, Lin JY, Huang HI, Li ML, Shih SR. Far upstream element binding protein 1 binds the internal ribosomal entry site of enterovirus 71 and enhances viral translation and viral growth. Nucleic Acids Res. Dec. 2011;39(22):9633-48. (Year: 2011).*

(Continued)

*Primary Examiner* — Michelle S Horning
(74) *Attorney, Agent, or Firm* — Fox Rothschild LLP

(57) ABSTRACT

Disclosed herein are recombinant polypeptides derived from FBP1 and FBP2. Also disclosed herein are recombinant expression vectors and recombinant host cells for producing the aforesaid recombinant polypeptides. The recombinant polypeptides are proven to be useful and effective in producing a picornavirus with a type I internal ribosome entry site (IRES), so as to facilitate the preparation of a viral vaccine.

16 Claims, 22 Drawing Sheets

Specification includes a Sequence Listing.

(56) References Cited

PUBLICATIONS

Kung YA, Hung CT, Chien KY, Shih SR. Control of the negative IRES trans-acting factor KHSRP by ubiquitination. Nucleic Acids Res. Jan. 9, 2017;45(1):271-287. doi: 10.1093/nar/gkw1042. Epub Nov. 28, 2016. (Year: 2016).*

Kung et al., Control of the negative IRES trans-acting factor KHSRP by ubiquitination. Nucleic Acids Res. Jan. 9, 2017; 44(1):271-287. Epub Nov. 28, 2016 (Year: 2017).

Huang et al, Far upstream element binding protein 1 binds the internal ribosomal entry site of enterovirus 71 and enhances viral translation and viral growth. Nucleic Acids Res. Dec. 2011; 39(22): 9633-9648 (Year: 2011).

GenBank ARV77948.1.

Zheng Y, Miskimins WK. Far upstream element binding protein 1 activates translation of p27Kip1 mRNA through its internal ribosomal entry site. Int J Biochem Cell Biol. Nov. 2011;43(11):1641-8. doi: 10.1016/j.biocel.2011.08.001. Epub Aug. 9, 2011. PMID: 21855647; PMCID: PMC3206725.

\* cited by examiner

RECOMBINANT POLYPEPTIDES DERIVED FROM FBP1 AND FBP2 AND USES OF THE SAME

CROSS-REFERENCE TO RELATED APPLICATION

This application is a divisional application of U.S. patent application Ser. No. 15/956,478 (filed on Apr. 18, 2018), which claims priority of Taiwanese Patent Application No. 106113165 (filed on Apr. 19, 2017). This application claims the benefits and priority of all these prior applications and incorporates by reference the contents of these prior applications in their entirety.

FIELD

The disclosure relates to recombinant polypeptides derived from FBP1 and FBP2. Such recombinant polypeptides are useful and effective in increasing viral yield.

BACKGROUND

Many RNA viruses utilize internal ribosome entry sites (IRESs) located in the 5' untranslated region (UTR) of genomic RNA to translate viral proteins in a cap-independent manner. Several cellular host proteins that can bind to and stabilize IRES structures and regulate IRES-driven translation have been reported, and these proteins are known as IRES trans-acting factors (ITAFs). Far upstream element-binding protein 1 (FUBP1, also known as FBP1) and far upstream element-binding protein 2 (KHSRP, also known as KH-type splicing regulatory protein, KSRP, FUBP2, FBP2 or P75) are among the known ITAFs that are functionally important in modulating viral IRES-driven translation.

IRES elements have been shown to exist in all genera of Picornaviridae, a type of cytoplasmic RNA virus known for its infectability on both animals and humans. At present, at least five different types of IRESs have been identified in picornaviruses, and each type is characterized by a distinct secondary structure and a different eIF (eukaryotic initiation factor)/ITAF-requirement. The picornavirus type I IRES is only found in enteroviruses such as enterovirus A71 (EVA71 or EV71), coxsackievirus B3 (CVB3), and human rhinovirus type 2 (HRV2).

EV71 is a positive single-strand RNA virus containing type I IRES in the Picornaviridae family, and is emerging as a potent threat worldwide. EV71 infections normally cause mild diseases, such as hand-foot-and-mouth disease (HFMD) or herpangina. However, children under five years of age are particularly susceptible to the most severe forms of EV71-associated neurological complications, including aseptic meningitis, brainstem and/or cerebellar encephalitis, acute flaccid paralysis (AFP), myocarditis, and rapid fatal pulmonary edema and hemorrhage.

The applicants previously found that FBP2 is a negative regulator (Lin J. Y. et al. (2009), *Nucleic Acids Res.*, 37:47-59), while FBP1 is a positive regulator of EV71 IRES-dependent translation (Huang P. N. et al. (2011), *Nucleic Acids Res.*, 39:9633-9648). Moreover, when the C-terminal of FBP2 is cleaved upon EV71 infection, the cleaved form of FBP2 (FBP2$^{1-503}$) then becomes a positive regulator of EV71 IRES-driven translation. Ubiquitination, and proteasomal and lysosomal activities may be involved in EV71-induced FBP2 truncation (Chen L. L. et al. (2013), *J Virol.*, 87:3828-3838).

By conducting research, the applicants surprisingly found that polypeptides derived from FBP1 and FBP2, respectively, can enhance viral IRES activity and increase viral yield. Therefore, these FBP1 and FBP2 polypeptides are expected to be useful in vaccine production.

SUMMARY

Therefore, according to a first aspect, the disclosure provides a method for producing a picornavirus with a type I internal ribosome entry site (IRES), the method comprising the steps of:
providing a recombinant cell including a recombinant expression vector, the recombinant expression vector containing a recombinant nucleic acid encoding a recombinant polypeptide which has an amino acid sequence corresponding to that of a truncated mutant product of a wild-type FBP1 protein having 644 amino acids in length, the truncated mutant product lacking a C-terminal domain of the wild-type FBP1 protein;
infecting the recombinant cell with the picornavirus;
incubating the infected recombinant cell; and
harvesting the picornavirus produced.

According to a second aspect, the disclosure provides a method for preparing a viral vaccine, which uses a harvested picornavirus as obtained by the method described in the first aspect.

According to a third aspect, the disclosure provides a method for producing a picornavirus with a type I internal ribosome entry site (IRES), the method comprising the steps of:
providing a recombinant cell including a recombinant expression vector, the recombinant expression vector containing a recombinant nucleic acid encoding a recombinant polypeptide which has an amino acid sequence corresponding to that of a mutant product of a wild-type FBP2 protein having 711 amino acids in length, each of amino acid residues at positions 109, 121 and 122 of the wild-type FBP2 protein being lysine, at least one of amino acid residues at positions 109, 121 and 122 of the mutant product being arginine instead of lysine;
infecting the recombinant cell with the picornavirus;
incubating the infected recombinant cell; and
harvesting the picornavirus produced.

According to a fourth aspect, the disclosure provides a method for preparing a viral vaccine using a harvested picornavirus as obtained by the method described in the third aspect.

According to a fifth aspect, the disclosure provides a method for preparing a viral vaccine using a harvested picornavirus as obtained by the method in the third aspect, wherein the recombinant cell further includes a recombinant expression vector that contains a recombinant nucleic acid encoding a recombinant polypeptide which has an amino acid sequence corresponding to that of a truncated mutant product of a wild-type FBP1 protein having 644 amino acids in length, the truncated mutant product lacking a C-terminal domain of the wild-type FBP1 protein.

BRIEF DESCRIPTION OF THE DRAWINGS

Other features and advantages of the present disclosure will become apparent in the following detailed description of the embodiments with reference to the accompanying drawings, of which.

Figure 1:
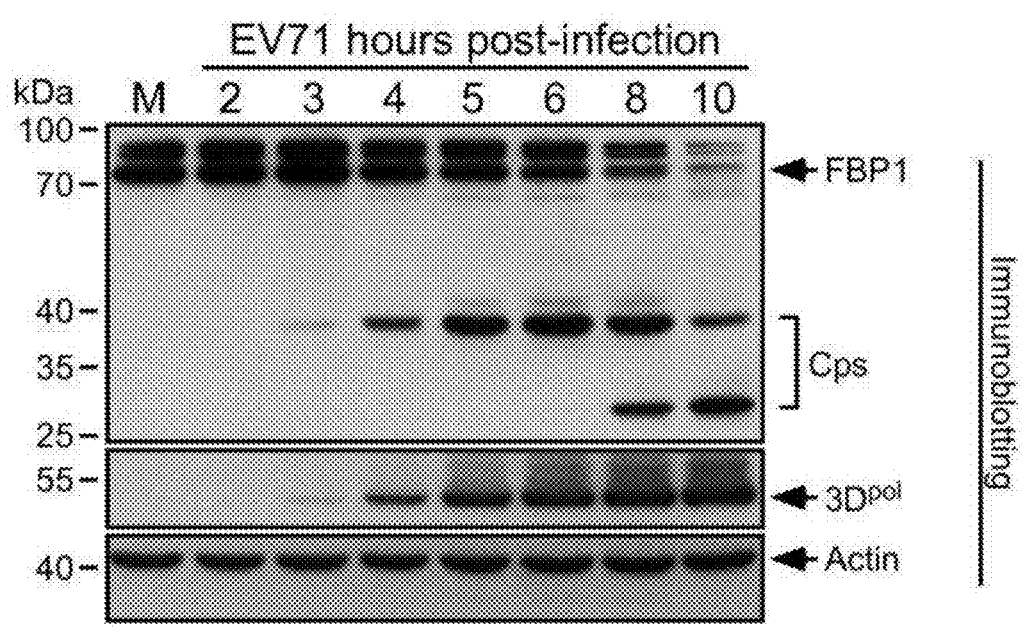
FIG. 1 shows the expression of FBP1 protein and its cleavage products in EV71 virus-infected human embryonal rhabdomyosarcoma (RD) cells at 2-10 hours post-infection (h.p.i.), in which viral $3D^{pol}$ protein was used as an indicator for virus infection, actin served as a loading control, and Cps represents the cleavage products of FBP1.

indicates non-significance, and the symbols "*" and "#" respectively represent p<0.05.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it should be clearly understood that the word "comprising" means "including but not limited to", and that the word "comprise" has a corresponding meaning.

Unless otherwise defined, all technical and scientific terms used herein have the meaning as commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The terms "polypeptide", "peptide", and "protein" as used herein can be interchangeably used, and refer to a polymer formed of amino acid residues, wherein one or more amino acid residues are naturally occurring amino acids or artificial chemical mimics. The term "recombinant polypeptide" or "recombinant protein" as used herein refers to polypeptides or proteins produced by recombinant DNA techniques, i.e., produced from cells transformed by an exogenous DNA construct encoding the desired polypeptide or the desired protein.

As used herein, an amino acid can be represented by the full name thereof, by the three-letter symbol corresponding thereto, or by the one-letter symbol corresponding thereto, as well-known in the art. In addition, the proteins are represented in accordance with the conventional way of describing peptides, that is, with the N-terminus (amino terminus) on the left side and the C-terminus (carboxyl terminus) on the right side.

A "wild-type" protein means that the protein will be active at a level of activity found in nature and typically will be the amino acid sequence found in nature. In an aspect, the term "wild type" or "parental sequence" can indicate a starting or reference sequence prior to a manipulation of this invention.

As used herein, the term "mutation" refers to a change introduced into a parental sequence, including, but not limited to, substitutions, insertions, and deletions (including truncations). The consequences of a mutation include, but are not limited to, the creation of a new character, property, function, phenotype or trait not found in the protein encoded by the parental sequence.

As used herein, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product. The mutant may be one that exists in nature, such as an allelic mutant, or one not yet identified in nature. The mutant may be conservatively altered, wherein substituted amino acid(s) retain structural or chemical characteristics similar to those of the original amino acid(s). Rarely, mutants may be substituted non-conservatively.

The term "truncated product" with reference to a protein, polypeptide or fragment thereof generally denotes such product that has a N-terminal and/or C-terminal deletion of one or more amino acid residues as compared to said protein, polypeptide or fragment thereof.

A "DNA coding sequence" is a double-stranded DNA sequence that is transcribed into an RNA (further translated into a polypeptide) in vivo under the control of appropriate regulatory sequences. The boundaries of the DNA coding sequence are determined by a start codon at the 5' (amino) terminus and a stop codon at the 3' (carboxyl) terminus. A coding sequence may include, but is not limited to, cDNA from eukaryotic mRNA, genomic DNA sequences from eukaryotic (e.g., mammalian) DNA, and even synthetic DNA sequences. "cDNA" is defined as copy DNA or complementary DNA, and is a product of a reverse transcription reaction from an mRNA transcript.

The terms "nucleic acid", "nucleic acid sequence", and "nucleic acid fragment" as used herein refer to a deoxyribonucleotide or ribonucleotide sequence in single-stranded or double-stranded form, and comprise naturally occurring nucleotides or artificial chemical mimics. The term "nucleic acid" as used herein is interchangeable with the terms "gene", "cDNA", "mRNA", "oligo-nucleotide", and "polynucleotide" in use.

As used herein, the term "DNA fragment" refers to a DNA polymer, in the form of a separate segment or as a component of a larger DNA construct, which has been derived either from isolated DNA or synthesized chemically or enzymatically such as by methods disclosed elsewhere.

Unless otherwise indicated, a nucleic acid sequence, in addition to the specific sequences described herein, also covers its complementary sequence, and the conservative analogs, related naturally occurring structural variants and/or synthetic non-naturally occurring analogs thereof, for example, homologous sequences having degenerative codon substitution, and conservative deletion, insertion, substitution, or addition. Specifically, degenerative codon substitution may be produced by, for instance, a nucleotide residue substitution at the third position of one or more selected codons in a nucleic acid sequence with other nucleotide residue(s).

The terms "recombinant vector" and "expression vector" as used herein can be interchangeably used, and refer to any recombinant expression system capable of expressing a selected nucleic acid sequence, in any competent host cell in vitro or in vivo, constitutively or inducibly. The recombinant vector may be an expression system in linear or circular form, and covers expression systems that remain episomal or that integrate into the host cell genome. The recombinant expression system may or may not have the ability to self-replicate, and it may drive only transient expression in a host cell.

As used herein, the term "transformation" can be used interchangeably with the term "transfection" and refers to the introduction of an exogenous nucleic acid molecule into a selected host cell. According to techniques known in the art, a nucleic acid molecule (e.g., a recombinant DNA construct or a recombinant vector) can be introduced into a selected host cell in various ways, such as calcium phosphate- or calcium chloride-mediated transfection, electroporation, microinjection, particle bombardment, liposome-mediated transfection, transfection using bacteriophages, or other methods.

The terms "cell", "host cell", "transformed host cell", and "recombinant host cell" as used herein can be interchangeably used, and not only refer to specific individual cells but also include sub-cultured offsprings or potential offsprings thereof. Sub-cultured offsprings formed in subsequent generations may include specific genetic modifications due to mutation or environmental influences and, therefore, may factually not be fully identical to the parent cells from which the sub-cultured offsprings were derived. However, sub-cultured cells still fall within the coverage of the terms used herein.

In order to increase viral yield for use in vaccine production, the applicants endeavored to develop improved methods and found that polypeptides derived from FBP1 and/or FBP2 can enhance viral IRES activity and increase viral yield.

Accordingly, the present disclosure provides a first recombinant polypeptide having an amino acid sequence corresponding to that of a truncated mutant product of a wild-type FBP1 protein having 644 amino acids in length. The truncated mutant product lacks a C-terminal domain of the wild-type FBP1 protein.

The term "corresponding to" is used herein to describe a polypeptide or nucleic acid of this disclosure which is similar or homologous to a corresponding mutant product modified from a parental polypeptide or nucleic acid, wherein the sequence of the polypeptide or nucleic acid of this disclosure differs from the sequence of the corresponding mutant product modified from the parental polypeptide or nucleic acid only by the presence of at least one amino acid residue or nucleotide residue variation.

Typically, the sequences of the polypeptide or nucleic acid of the disclosure and the corresponding mutant product modified from the parental polypeptide or nucleic acid exhibit a high percentage of identity, such as at least about 70%, at least about 80%, at least about 90%, at least about 95%, at least about 98% identity, or at least about 99% identity.

In certain embodiments, the truncated mutant product of the wild-type FBP1 protein has amino acid deletions at positions 372-644 of the wild-type FBP1 protein. In an embodiment of the present disclosure, the truncated mutant product of the wild-type FBP1 protein has an amino acid sequence of SEQ ID NO: 4.

In certain embodiments, the truncated mutant product of the wild-type FBP1 protein has amino acid deletions at positions 63-78 and positions 372-644 of the wild-type FBP1 protein. In an embodiment of the present disclosure, the truncated mutant product of the wild-type FBP1 protein has an amino acid sequence of SEQ ID NO: 46.

The present disclosure also provides a first recombinant nucleic acid encoding the first recombinant polypeptide as described above. In certain embodiments, the first recombinant nucleic acid has a nucleotide sequence selected from SEQ ID NO: 3, SEQ ID NO: 44 and SEQ ID NO: 45.

In addition, the present disclosure also provides a second recombinant polypeptide having an amino acid sequence corresponding to that of a mutant product of a wild-type FBP2 protein having 711 amino acids in length. Each of amino acid residues at positions 109, 121 and 122 of the wild-type FBP2 protein is lysine, and at least one of amino acid residues at positions 109, 121 and 122 of the mutant product is not lysine.

In certain embodiments, the at least one amino acid residue at positions 109, 121 and 122 of the mutant product is arginine. In an exemplary embodiment, one amino acid residue at positions 109, 121 and 122 of the mutant product is arginine. In an exemplary embodiment, two of the amino acid residues at positions 109, 121 and 122 of the mutant product are arginine. In yet another exemplary embodiment, all of the amino acid residues at positions 109, 121 and 122 of the mutant product are arginine.

In an embodiment of the present disclosure, the amino acid sequence of the second recombinant polypeptide is selected from the group consisting of SEQ ID NO: 8, SEQ ID NO: 10, SEQ ID NO: 12, SEQ ID NO: 14 and SEQ ID NO: 16.

The present disclosure also provides a second recombinant nucleic acid encoding the aforesaid second recombinant polypeptide derived from FBP2. In certain embodiments, the second nucleotide sequence is selected from the group consisting of SEQ ID NO: 7, SEQ ID NO: 9, SEQ ID NO: 11, SEQ ID NO: 13 and SEQ ID NO: 15.

The first and second recombinant nucleic acid sequences according to the present disclosure can be utilized to construct various recombinant expression vectors for expressing the aforementioned recombinant polypeptides using a standard technique known to one of ordinary skill in the art.

Therefore, the present disclosure provides a recombinant expression vector comprising the first recombinant nucleic acid and/or the second recombinant nucleic acid.

In certain embodiments, the first and/or second recombinant nucleic acids of the recombinant expression vector may be introduced into a genome of the recombinant cell. In an exemplary embodiment, an endogenous FBP2 gene in the genome of the recombinant cell is deleted, disrupted, or disabled.

As used herein, the term "delete" refers to partial or entire removal of a coding region of a gene.

As used herein, the term "disrupt" refers to removal, insertion, or mutation of a nucleotide of a gene.

As used herein, the term "disable" refers to inactivating a gene or the protein encoded by the gene so as to force the gene or protein to lose its activity or function.

The recombinant expression vector according to the present disclosure can be used to transform or transfect a desired host cell. Consequently, the disclosure also provides a recombinant cell comprising the aforementioned recombinant expression vector.

According to the disclosure, the host cell may be a mammalian cell. Examples of the mammalian cell suitable for used in the present disclosure include, but are not limited to, an RD cell, a 293T cell, a Vero cell, a MDCK cell, a PER.C6 cell, a MRC-5 cell, a WI-38 cell, etc.

Since the aforementioned recombinant polypeptides derived from FBP1 and/or FBP2 can promote picornavirus type I IRES-driven translation and increase viral yield, these polypeptides are expected to be useful in the production of viral vaccine. Therefore, the present disclosure provides a method for producing a picornavirus with a type I IRES, which includes the steps of:

providing the aforesaid recombinant cell;
infecting the recombinant cell with the picornavirus;
incubating the infected recombinant cell; and
harvesting the picornavirus produced.

According to the disclosure, the picornavirus with the type I IRES may be an enterovirus selected from the group consisting of enterovirus A (such as enterovirus A71 and coxsackieviruses A6 and A16), enterovirus B (such as coxsackievirus B3), enterovirus C (such as coxsackieviruses A21 and A24, and polioviruses 1, 2 and 3), enterovirus D (such as enterovirus D68), rhinovirus A, rhinovirus B, and rhinovirus C, and combinations thereof. In an embodiment of the disclosure, the enterovirus is enterovirus A71. In another embodiment of the disclosure, the enterovirus is coxsackievirus B3.

The disclosure also provides a method for preparing a viral vaccine using the harvested picornavirus obtained by the aforesaid method for producing the picornavirus.

The present disclosure will be further described by way of the following examples. However, it should be understood that the following examples are intended solely for the purpose of illustration and should not be construed as limiting the disclosure in practice.

EXAMPLES

General Experimental Materials:
1. Primers used in the polymerase chain reaction (PCR) experiments, infra, were synthesized by Mission Biotech, Taipei, Taiwan.
2. EV71 strain Tainan/4643/98 viruses (GenBank accession number AF304458) and CVB3 strain viruses were obtained from Chang Gung Memorial Hospital, Linkou, Taiwan.
3. Cell cultures:

Human embryonal rhabdomyosarcoma (RD) cells (ATCC, CCL-136) and 293T cells (ATCC, CCL-3216) used in the following experiments were purchased from ATCC (American Type Culture Collection, Manassas, Va., USA). The cells of the respective type were incubated in a Petri dish containing Dulbecco's modified Eagle medium (DMEM; Gibco, Grand Island, N.Y.) supplemented with 10% fetal bovine serum (FBS; Gibco), 100 units/mL of penicillin, 100 μg/mL of streptomycin and 0.25 μg/mL of amphotericin B, followed by cultivation in an incubator with culture conditions set at 37° C. and 5% $CO_2$. Medium change was performed every two days. Cell passage was performed when the cultured cells reached 90% of confluence.

4. FBP1-related recombinant plasmids:
   (a) Plasmid pFLAG-CMV2-FBP1 carrying, amongst others, a FBP1 coding sequence (SEQ ID NO: 1, GeneBank accession no. KY569017) encoding a wild-type FBP1 protein having an amino acid sequence of SEQ ID NO: 2, was generated as follows. The FBP1 coding sequence was amplified from a plasmid pCMV-tag2B-FBP1 (as described in Huang P. N. et al. (2011), supra) using a primer pair FBP1-F1 and FBP1-R1 as shown in Table 1. The resultant FBP1 coding sequence was then in-frame inserted into the pFLAG-CMV2 vector (Sigma, E7033) at the NotI and EcoRV sites.
   (b) For obtaining five C-terminal and/or N-terminal truncated FBP1 proteins, i.e. $FBP1^{1-371}$ (having an amino acid sequence of SEQ ID NO: 4), $FBP1^{372-644}$, $FBP1^{1-443}$, $FBP1^{185-644}$, and $FBP1^{185-443}$, each of their corresponding coding sequences was amplified from pFLAG-CMV2-FBP1 using the respective primer pairs as shown in Table 1. A respective one of these coding sequences was in-frame inserted between the NotI and EcoRV sites of the pFLAG-CMV2 vector, so as to obtain five recombinant plasmids, i.e., pFLAG-CMV2-$FBP1^{1-371}$, pFLAG-CMV2-$FBP1^{372}$-644, pFLAG-CMV2-$FBP1^{1-443}$, pFLAG-CMV2-$FBP1^{185-644}$ and pFLAG-CMV2-FBP1185-443.

TABLE 1

| (Full or Truncated) FBP1 coding sequences | Primer Pair | The primer's nucleotide sequence (5'→3') | SEQ ID NO. |
|---|---|---|---|
| FBP1 | FBP1-F1 | AAGCTT<u>GCGGCC</u>GCGATGGCAGACTATTCAACA<br>NbtI | 17 |
|  | FBP-R1 | GGTACC<u>GATATC</u>AGTTATTGGCCCTGAGGTGC<br>EcoRV | 18 |
| $FBP1^{1-371}$ | FBP1-F1 | AAGCTT<u>GCGGCC</u>GCGATGGCAGACTATTCAACA<br>NbtI | 17 |
|  | FBP-R2 | GGTACC<u>GATATC</u>AGTTATCCCATGTTCCAGTTGCC<br>EcoRV | 19 |
| $FBP1^{372-644}$ | FBP-F2 | AAGCTT<u>GCGGCC</u>GCGATGCCACCTGGTGGACTACAG<br>NbtI | 20 |
|  | FBP-R1 | GGTACC<u>GATATC</u>AGTTATTGGCCCTGAGGTGC<br>EcoRV | 18 |
| $FBP1^{1-443}$ | FBP1-F1 | AAGCTT<u>GCGGCC</u>GCGATGGCAGACTATTCAACA<br>NbtI | 17 |
|  | FBP-R3 | GGTACC<u>GATATC</u>AGTTATATGAGTTGCCGAGCATA<br>EcoRV | 21 |
| $FBP1^{185-644}$ | FBP-F3 | AAGCTT<u>GCGGCC</u>GCGATGAATGCAGTTCAAGAAATCATG<br>NbtI | 22 |
|  | FBP-R1 | GGTACC<u>GATATC</u>AGTTATTGGCCCTGAGGTGC<br>EcoRV | 17 |
| $FBP1^{185-443}$ | FBP-F3 | AAGCTT<u>GCGGCC</u>GCGATGAATGCAGTTCAAGAAATCATG<br>NbtI | 22 |
|  | FBP-R3 | GGTACC<u>GATATC</u>AGTTATATGAGTTGCCGAGCATA<br>EcoRV | 21 |

Note:
The underlined nucleotides represent the recognition site of a restriction enzyme as indicated below.

(c) Plasmid pBacPAK8-MTEGFP-His-FBP1 carrying, amongst others, a His-FBP1 coding sequence encoding a His-FBP1 fusion protein (i.e., a FBP1 protein fused with His tag at the N-terminus), was previously constructed (Huang P. N. et al. (2011), supra). For the construction of pBacPAK8-MTEGF-P-His-FBP1$^{1-371}$, a His-FBP1$^{1-371}$ coding sequence was amplified by PCR using the following primer pair, followed by insertion into the pBacPAK8-MTEGFP-His vector kindly provided by Dr. Tsu-An Hsu (National Health Research Institute, MiaoLi, Taiwan) at the XbaI and KpnI sites.

Forward primer (with the XbaI recognition site thereof underlined)

```
                                      (SEQ ID NO: 23)
5'-GCTCTAGAATGGCAGACTATTCAACAGTGCCT-3'
```

Reverse primer (with the KpnI recognition site thereof underlined)

```
                                      (SEQ ID NO: 24)
5'-CGGGGTACCTCCCATGTTCCAGTTGCCTTG-3'
```

(d) Plasmid pFLAG-CMV2-FBP1 obtained in above Item (a) was adopted as a template for the construction of various mutant pFLAG-CMV2-FBP1 plasmids, using a site-directed mutagenesis kit (Stratagene) and the primer pairs as shown in Table 2.

(e) Plasmids pFLAG-FBP1-HA and pFLAG-FBP1-G371K-HA respectively carrying, amongst others, a FBP1-HA (human influenza hemagglutinin) coding sequence encoding an FBP1-HA fusion protein (i.e., an FBP1 protein fused with HA at the C-terminus) and a FBP1-G371K-HA coding sequence encoding an FBP1-G371K-HA fusion protein, were generated as follows. The FBP1-HA and FBP1-G371K-HA coding sequences were respectively amplified from pFLAG-CMV2-FBP1 and pFLAG-CMV2-FBP1-G371K obtained in above Items (a) and (d) using the following primer pair. Each of the obtained coding sequences was then in-frame inserted at the NotI and EcoRV sites of the respective pFLAG-CMV2 vector.

Forward primer (with the NotI recognition site thereof underlined)

```
                                      (SEQ ID NO: 17)
5'-AAGCTTGCGGCCGCGATGGCAGACTATTCAACA-3'
```

Reverse primer (with the EcoRV recognition site thereof underlined)

```
                                      (SEQ ID NO: 39)
5'-GGTACCGATATCAGT
TAAGCGTAATCTGGAACATCGTATGGGTAAG
AGCCACCTTGGCCCTGAGGTGC-3'
```

TABLE 2

| Mutant FBP1 coding sequences | Primer pair | The primer's nucleotide sequence (5'→3') | SEQ ID NO. |
|---|---|---|---|
| FBP1-G345-362K | FBP1-MF1 | AGTGTTCAGGCTAAAAATCCTAAAAAACCTAAACCTAAAAAACGAAAAAGAAAAAGAGGTCAAGGC | 25 |
| | FBP1-MR1 | GCCTTGACCTCTTTTTCTTTTTCGTTTTTTAGGTTTAGGTTTTTTAGGATTTTTAGCCTGAACACT | 26 |
| FBP1-G364-380K | FBP1-MF2 | GGAAGAGGTAGAAAACAAAAAAACTGGAACATGAAACCACCTAAAAAAACTACAGGAATTTAAT | 27 |
| | FBP1-MF2 | ATTAAATTCCTGTAGTTTTTTAGGTGGTTTCATGTTCCAGTTTTTTTGTTTTCTACCTCTTCC | 28 |
| FBP1-G364K | FBP1-MF3 | AGAGGTAGAAAACAAGGCAAC | 29 |
| | FBP1-MR3 | GTTGCCTTGTTTTCTACCTCT | 30 |
| FBP1-G366K | FBP1-MF4 | AGAGGTCAAAAAAACTGGAAC | 31 |
| | FBP1-MR4 | GTTCCAGTTTTTTTGACCTCT | 32 |
| FBP1-G371K | FBP1-MF5 | TGGAACATGAAACCACCTGGT | 33 |
| | FBP1-MR5 | ACCAGGTGGTTTCATGTTCCA | 34 |
| FBP1-G374K | FBP1-MF6 | GGACCACCTAAAGGACTACAG | 35 |
| | FBP1-MR6 | CTGTAGTCCTTTAGGTGGTCC | 36 |
| FBP1-G375K | FBP1-MF7 | CCACCTGGTAAACTACAGGAA | 37 |
| | FBP1-MR7 | TTCCTGTAGTTTACCAGGTGG | 38 |

Note:
Each framed region in the nucleotide sequence of an indicted primer was designed to introduce lysine residue(s) at the mutation site(s) as indicated.

in which the framed region in the nucleotide sequence represents the HA coding sequence.

(f) Plasmids pFLAG-CMV2-FBP1, pFLAG-CMV2-FBP1$^{1-371}$ and pFLAG-CMV2-FBP1-G371K obtained in above Items (a), (b) and (d) respectively served as templates for the construction of recombinant plasmids pFLAG-Hr-FBP1$^{WM}$, pFLAG-CMV2-FBP1$^{1-371-WM}$ and pFLAG-Hr-FBP1-G371K$^{WM}$, using a site-directed mutagenesis kit and a primer pair as shown in Table 3. The obtained recombinant plasmids pFLAG-Hr-FBP1$^{WM}$, pFLAG-Hr-FBP1$^{1-371-WM}$ and pFLAG-Hr-FBP1-G371K$^{WM}$ respectively carried a wobble mutant FBP1 (FBP1$^{WM}$) coding sequence, an FBP1$^{1-371-WM}$ coding sequence (SEQ ID NO: 44) and an FBP1-G371K$^{WM}$ coding sequence that are resistant to the targeting of shFBP1 and encode a respective one of FBP1$^{WM}$, FBP1$^{1-371-WM}$ and FBP1-G371K$^{WM}$.

(g) Plasmid pFLAG-Hr-FBP1$^{WM}$ obtained in above Item (f) served as a template for the construction of recombinant plasmid pFLAG-Hr-FBP1$^{1-371-WM-delNLS}$, which contains an FBP1$^{1-371-WM-delNLS}$ coding sequence (SEQ ID NO: 45) encoding FBP1$^{1-371-WM}$ with a deletion of nuclear localization signal (NLS) sequence at a region spanning amino acid residues 63-78 (i.e., FBP1$^{1-371-WM-delNLS}$ having an amino acid sequence of SEQ ID NO: 46). The FBP1$^{1-371-WM-delNLS}$ coding sequence was amplified from pFLAG-Hr-FBP1$^{WM}$ with Nested PCR using two primer pairs (FBP1-F1/FBP1-WMR2 and FBP1-WMF2/FBP1-R1) as shown in Table 3, followed by in-frame insertion between the NotI and EcoRV sites of the pFLAG-CMV2 vector.

5) encoding a wild-type FBP2 protein having an amino acid sequence of SEQ ID NO: 6 (NCBI accession no. NP_003676.2), was generated as follows. The FBP2 optimized coding sequence was optimized from the DNA of FBP2 provided by Douglas L. Black (University of California, Los Angeles) and then amplified by PCR using a primer pair as shown in Table 4. Nucleotides 1 to 890 of FBP2 were optimized using GeneART to decrease GC content without changing the amino acids (Chen L. L. et al. (2013), supra). The obtained coding sequence was subcloned between the EcoRI and EcoRV sites of a pFLAG-CMV2 vector.

(b) Plasmid pFLAG-CMV2-FBP2 obtained in above Item (a) was adopted as a template for the construction of eight mutant recombinant plasmids, including pFLAG-CMV2-FBP2-K109R, pFLAG-CMV2-FBP2-K121R, pFLAG-CMV2-FBP2-K122R, pFLAG-CMV2-FBP2-K251R, pFLAG-CMV2-FBP2-K628R, pFLAG-CMV2-FBP2-K646R, pFLAG-CMV2-FBP2-K654R and pFLAG-CMV2-FBP2-K121,122R, using a site-directed mutagenesis kit and primer pairs as shown in Table 4. Plasmid pFLAG-CMV2-FBP2-K109, 121, 122R was similarly constructed except that the template and the primer pair used were pFLAG-CMV2-FBP2-K121,122R and primers FBP2-F109/FBP2-R109. Also, plasmid pFLAG-CMV2-FBP2-N-ter5K5R was similarly constructed except that the template used was pFLAG-CMV2-FBP2-K109, 121, 122R, and that two primer pairs including primers FBP2-F71/FBP2-R71 and FBP2-F87/FBP2-R87 were applied.

TABLE 3

| Wobble mutant FBP1 coding sequences | Primer pair | The primer's nucleotide sequence (5'→3') | SEQ ID NO. |
|---|---|---|---|
| FBP1$^{WM}$, FBP1-G371K$^{WM}$ and FBP1$^{1-371-WM}$ | FBP1-WMF1<br>FBP1-WMR1 | CCATTCCTAGGTTCGCAGTCGGTATAGTTATAGGA<br>TCCTATAACTATACCGACTGCGAACCTAGGAATGG | 40<br>41 |
| FBP1$^{1-371-WM-delNLS}$ | FBP1-F1 | AAGCTT<u>GCGGCC</u>GCGATGGCAGACTATTCAACA<br>NotI | 17 |
| | FBP1-WMR2 | AGTCATTTTGAGGAGCTCCCCCATAACCATAG | 42 |
| | FBP1-WMF2 | CTATGGTTATGGGGGAGCTCCTCAAAATGACT | 43 |
| | FBP1-R1 | GGTACC<u>GATATC</u>AGTTATCCCATGTTCCAGTTGCC<br>EcoRV | 19 |

Note:
The underlined nucleotides represent the recognition site of a restriction enzyme as indicated below.

5. FBP2-related recombinant plasmids
  (a) Plasmid pFLAG-CMV2-FBP2 carrying, amongst others, an FBP2 optimized coding sequence (SEQ ID NO:

TABLE 4

| (Wild-type or Mutant) FBP2 coding sequence | Primer pair | The primer's nucleotide sequence (5'→3') | SEQ ID NO. |
|---|---|---|---|
| FBP2 (SEQ ID NO: 5, encoding an amino acid sequence of SEQ ID NO: 6) | FBP2-F1 | ACC<u>GAATTC</u>GCCACCATGAGCGACTACAGCAC<br>EcoRI | 47 |
| | FBP2-R1 | GTACC<u>GATATC</u>AGTTGAGCCTGCTGCTGTCCCT<br>EcoRV | 48 |
| FBP2-K109R | FBP2-F109 | GGCGGCCAG AGA CGGCAGCTG | 49 |

TABLE 4-continued

| (Wild-type or Mutant) FBP2 coding sequence | Primer pair | The primer's nucleotide sequence (5'→3') | SEQ ID NO. |
|---|---|---|---|
| (SEQ ID NO: 9, encoding an amino acid sequence of SEQ ID NO: 10) | FBP2-R109 | CAGCTGCCG TCT CTGGCCGCC | 50 |
| FBP2-K121R | FBP2-F121 | CCCGAGAGC AGG AAGCTGGCC | 51 |
| (SEQ ID NO: 11, encoding an amino acid sequence of SEQ ID NO: 12) | FBP2-R121 | GGCCAGCTT CCT GCTCTCGGG | 52 |
| FBP2-K122R | FBP2-F122 | GAGAGCAAG AGG CTGGCCTCC | 53 |
| (SEQ ID NO: 13, encoding an amino acid sequence of SEQ ID NO: 14) | FBP2-R122 | GGAGGCCAG CCT CTTGCTCTC | 54 |
| FBP2-K251R | FBP2-F251 | GTCATCGGA AGG GGCGGCGAG | 55 |
|  | FBP2-R251 | CTCGCCGCC CCT TCCGATGAC | 56 |
| FBP2-K628R | FBP2-F628 | TATTACAAA AGG ATCGGCCAG | 57 |
|  | FBP2-R628 | CTGGCCGAT CTT TTTGTAATA | 58 |
| FBP2-K646R | FBP2-F646 | GACTACACG AGG GCTTGGGAG | 59 |
|  | FBP2-R646 | CTCCCAAGC CCT CGTGTAGTC | 60 |
| FBP2-K654R | FBP2-F654 | TACTACAAG AGG CAAGCGCAA | 61 |
|  | FBP2-R654 | TTGCGCTTG CCT CTTGTAGTA | 62 |
| FBP2-K121, 122R | FBP2-F121/122 | CCCGAGAGC AGGAGG CTGGCCTCC | 63 |
|  | FBP2-R121/122 | GGAGGCCAG CCTCCT GCTCTCGGG | 64 |
| FBP2-K109, 121, 122R | FBP2-F109 | GGCGGCCAG AGA CGGCAGCTG | 49 |
| (SEQ ID NO: 7, encoding an amino acid sequence of SEQ ID NO: 8) | FBP2-R109 | CAGCTGCCG TCT CTGGCCGCC | 50 |
| FBP2-N-ter5K5R (K71, 87, 109, 121, 122R) | FBP2-F71 | TGGCATCAG AGA GGATGCCTT | 65 |
|  | FBP2-R71 | AAGGCATCC TCT CTGATGCCA | 66 |
|  | FBP2-F87 | ATCGCTGCT AGG ATTGGCGGC | 67 |
|  | FBP2-R87 | GCCGCCAAT CCT AGCAGCGAT | 68 |

Note:
Each framed region in the nucleotide sequence of an indicted primer was designed to introduce arginine residue(s) at the mutation site(s) as indicated.

6. 2A protease)(2A$^{pro}$)-related recombinant plasmids
(a) Plasmid pGEX-6P-1-EV71-2A was constructed as follows. EV71 2A protease)(2A$^{pro}$) cDNA was amplified from the cDNA clone of EV71 (SRS Labs, Inc.) using the following primer pair, followed by insertion into pGEX-6P-1 (GE Healthcare) at the EcoRI and NotI sites.

Forward primer (with the EcoRI recognition site thereof underlined)

(SEQ ID NO: 69)
5'-CCG GAATTC GGGAAATTTGGACAGCAG-3'

Reverse primer (with the NotI recognition site thereof underlined)

(SEQ ID NO: 70)
5'-CACGAT GCGGCCGC GCTCCTGCTCCATGGCTTC-3'

(b) Plasmid pGEX-6P-1-EV71-2A then served as a template for the construction of mutant pGEX-6P-1-EV71-2A-C110S, which carries a nucleic acid sequence encoding a mutant viral 2A$^{pro}$ protein having C110S mutation. Such contruction was conducted using a site-directed mutagenesis kit and the primer pair below.

```
Forward primer
                                   (SEQ ID NO: 71)
5'-CCAGGGGATTCCGGTGGCATT-3'

Reverse primer
                                   (SEQ ID NO: 72)
5'-AATGCCACCGGAATCCCCTGG-3'
```

General Experimental Procedures:

Concerning the experimental methods and relevant techniques for DNA cloning as employed in this disclosure, such as DNA cleavage by restriction enzymes, polymerase chain reaction (PCR), DNA ligation with T4 DNA ligase, agarose gel electrophoresis, plasmid transformation, etc., reference may be made to the following textbook widely known in the art: Sambrook J. and Russell D. W. (2001), Molecular Cloning: a Laboratory Manual, 3rd ed., Cold Spring Harbor Laboratory Press, New York. Site-directed mutagenesis PCR was performed substantially according to the the manufacturer's instructions. These techniques can be readily performed by those skilled in the art based on their professional knowledge and experience.

1. Virus Infection:

When the cultured cells reached 90% of confluence, infection by a virus, such as EV71 strain Tainan/4643/98 or CVB3 strain, at a given multiplicity of infection (m.o.i.), was performed in serum-free DMEM. The viruses were allowed to adsorb at 37° C. for 1 hour, after which the infected cells were washed with phosphate-buffered saline (PBS) and incubated at 37° C. in DMEM containing 2% FBS.

2. Expression and Purification of Recombinant Proteins:

The $2A^{pro}$ and $2A^{pro}$-C110S proteins fused to a GST-tag as respectively produced by pGEX-6P-1-EV71-2A and pGEX-6P-1-EV71-2A-C110S in BL21 (DE3) *E. coli* cells (Yeastern Biotech, Taiwan) were purified using a GSTrap FF column (GE Healthcare, Waukesha, Wis.) according to the manufacturer's instructions. The GST-tag of the respective puried fusion protein was removed with PreScission Protease (GE Healthcare), so as to obtain $2A^{pro}$ and $2A^{pro}$-C110S proteins.

Experimental procedures for the expression and purification of recombinant His-tagged FBP1 was reported previously in Huang P. N. et al. (2011), supra.

3. Coupled Transcription/Translation of [$^{35}$S] Methionine-Labeled FBP1:

To produce each of [$^{35}$S] methionine-labeled wild-type or mutant FBP1 proteins, a DNA fragment containing the T7 promoter and the designated coding sequence was amplified using PCR and a respective primer pair shown in Table 5 from the corresponding plasmid obtained in above Items (a) and (d) of the section entitled "4. FBP1-related recombinant plasmids" of the General Experimental Materials, and the designated protein was produced with the TNT-coupled reticulocyte lysate system (Promega, Madison, WI) according to the manufacturer's instructions.

In addition, each of [$^{35}$S] methionine-labeled truncated FBP1 proteins was generally produced as set forth above, except that the template to be applied was pFLAG-CMV2-FBP1 and the respective primer pair shown in Table 5 was used.

TABLE 5

| FBP1 coding sequences | Primer pair | The primer's nucleotide sequence (5'→3') | SEQ ID NO. |
|---|---|---|---|
| FBP1/ mutant FBP1 | FBP1-F4 | GGATCCTAATACGACTCACTATAGGGA ACAGCCACCATGGCAGACTATTCAACAGTGCCT | 73 |
| | FBP1-R4 | CCAGCACCTCAGGGCCAATAAAAAAAAAAAAAAAAAAAAAAAAAAAAAA | 74 |
| FBP1$^{1-371}$ | FBP1-F4 | GGATCCTAATACGACTCACTATAGGGA ACAGCCACCATGGCAGACTATTCAACAGTGCCT | 73 |
| | FBP1-R5 | TTATCCCATGTTCCAGTTGCC | 75 |
| FBP1$^{372-644}$ | FBP1-F5 | GGATCCTAATACGACTCACTATAGGGA ACAGCCACCATGCCACCTGGTGGACTACAGGAA | 76 |
| | FBP1-R4 | CCAGCACCTCAGGGCCAATAAAAAAAAAAAAAAAAAAAAAAAAAAAAAA | 74 |
| FBP1$^{1-443}$ | FBP1-F4 | GGATCCTAATACGACTCACTATAGGGA ACAGCCACCATGGCAGACTATTCAACAGTGCCT | 73 |
| | FBP1-R6 | TTATATGAGTTGCCGAGCATA | 77 |
| FBP1$^{185-644}$ | FBP1-F6 | GGATCCTAATACGACTCACTATAGGGA ACAGCCACCATGAATGCAGTTCAAGAAATCATG | 78 |
| | FBP1-R4 | CCAGCACCTCAGGGCCAATAAAAAAAAAAAAAAAAAAAAAAAAAAAAAA | 74 |

TABLE 5-continued

| FBP1 coding sequences | Primer pair | The primer's nucleotide sequence (5'→3') | SEQ ID NO. |
|---|---|---|---|
| FBP1[185-443] | FBP1-F6 | GGATCC`TAATACGACTCACTATAGGG`A ACAGCCACCATGAATGCAGTTCAAGAAA TCATG | 78 |
|  | FBP1-R6 | TTATATGAGTTGCCGAGCATA | 77 |

Note:
The T7 promoter sequence and the start codon are framed and boldfaced, respectively.

4. Immunoblot Analysis:

Protein samples were resolved in sodium dodecyl sulfate-polyacrylamide (SDS-PAGE) gels, and the separated proteins were subsequently transferred to polyvinylidene difluoride (PVDF) membranes (GE Healthcare). The blotted PVDF membranes thus obtained were blocked with tris-buffered saline (TBS) and 0.1% (vol/vol) TWEEN 20 (polyethylene glycol sorbitan monolaurate) containing 5% non-fat dry milk, followed by washing with TBST 3 times, each time for 15 min, and then probing with the indicated primary antibodies. For staining with secondary antibodies, the probed membranes were washed with TBST 3 times, each time for 15 min, and were then incubated with an HRP-conjugated anti-mouse antibody or an HRP-conjugated anti-rabbit antibody for 60 minutes at room temperature. HRP was detected using the Western Lightning Chemiluminescence Kit (PerkinElmer Life Sciences, Boston, Mass.).

5. Viral Plaque Assay:

6×10$^5$ RD cells were seeded into each well of a 6-well plate and incubated for 24 h, followed by addition of 500 μL of virus diluent prepared in serum-free DMEM in duplicate to each well. The viruses were allowed to adsorb at 37° C. for 1 hour, after which the infected cells were washed with PBS. 2 mL of an agarose overlay medium (0.3% agarose in DMEM containing 2% FBS) was added to each well and the plates were kept at room temperature until the agarose overlay medium turned solid. The plates were moved to a 37° C. incubator for 2 to 4 days of incubation, and then the cells were fixed with a 3.6% formaldehyde solution at room temperature for 2 hours. The agarose overlay was removed, and then the fixed cells in each well were stained with 0.5% crystal violet for 2 min. After rinsing the stained cells with water, the viral plaques in each well were counted. The viral titer was determined by substituting the value of the viral plaques counted into the following formula (1):

$$A=B/(C\times 0.5) \quad (1)$$

wherein: A=viral titer (plaque forming units (pfu)/mL)
B=the viral plaques counted
C=the dilution factor of the virus Example 1

Cleavage of FBP1 During EV71 Infection

To examine FBP1 expression and to analyze patterns of cleaved FBP1 in EV71-infected RD cell lysates, the following experiments were conducted.

Experimental Procedures:

RD cells were infected with EV71 strain Tainan/4643/98 at a m.o.i. of 40 according to the procedures as described in the preceding section, entitled "1. Virus infection," of the General Experimental Procedures. Mock-infected cells served as a control group.

At 2, 3, 4, 5, 6, 8 and 10 hours post-infection (h.p.i.), the infected cells were washed with PBS and lysed with IGEPAL CA630 (octylphenoxy poly(ethyleneoxy) ethanol) lysis buffer (150 mM NaCl, 1% IGEPAL CA630 (octylphenoxy poly(ethyleneoxy)ethanol), 50 mM Tris-base [pH 8.0]) for 30 minutes on ice. The resultant cell lysates were centrifuged at 10,000× g for 10 minutes at 4° C., and the supernatants were collected to serve as total protein samples.

Total protein samples in equal amount (determined by Bradford assay) at each designated time point of post-infection were subjected to immunoblot analysis according to the procedures as described in the preceding section, entitled "4. Immunoblot analysis," of the General Experimental Procedures. For the purpose of comparison, the total protein sample from the mock-infected cells was subjected to the same analysis.

For analyzing patterns of cleaved FBP1 protein in EV71-infected RD cell lysates, the total protein samples obtained from the mock-infected and EV71-infected cell lysates at each designated time point of post-infection (i.e. 4, 6, 8 and 10 h.p.i.) were also subjected to immunoblot analysis using two specific FBP1 antibodies generated from the applicants' lab, i.e. Ab-N antibody and Ab-C antibody that respectively recognize the N-terminal region (amino acid positions 61-180) and C-terminal region (amino acid positions 293-644) of FBP1. In addition, viral 3D$^{pol}$ protein was used as an indicator for virus infection, and actin was used as a loading control. The primary and secondary antibodies used for detecting the respective protein in this example are shown in Table 6 below.

TABLE 6

| Proteins | Primary antibody | Secondary antibody |
|---|---|---|
| FBP1 | Mouse monoclonal anti-FBP1 antibody (Cat. No. 611286, BD Biosciences, Franklin Lakes, NJ) | Amersham ECL Mouse IgG, HRP-linked whole Ab (from sheep) (Cat. No. NA931, GE Healthcare) |
| N-terminal region of FBP1 | Mouse monoclonal anti-FBP1 antibody (Cat. No. 611286, BD Biosciences, Franklin Lakes, NJ) | Amersham ECL Mouse IgG, HRP-linked whole Ab (from sheep) |
| C-terminal region of FBP1 | Rabbit polyclonal anti-FBP1 antibody (Cat. No. GTX115154, GeneTex, San Antonio, TX) | Amersham ECL Rabbit IgG, HRP-linked whole Ab (from donkey) (Cat. No. NA934, GE Healthcare) |
| 3D$^{pol}$ | Mouse anti-3D$^{pol}$ monoclonal antibody (generated by the applicants) | Amersham ECL Mouse IgG, HRP-linked whole Ab (from sheep) |

TABLE 6-continued

| Proteins | Primary antibody | Secondary antibody |
|---|---|---|
| Actin | Mouse monoclonal anti-actin antibody (Cat. No. MAB1501 Millipore, Billerica, MA) | Amersham ECL Mouse IgG, HRP-linked whole Ab (from sheep) |

Figure 2:
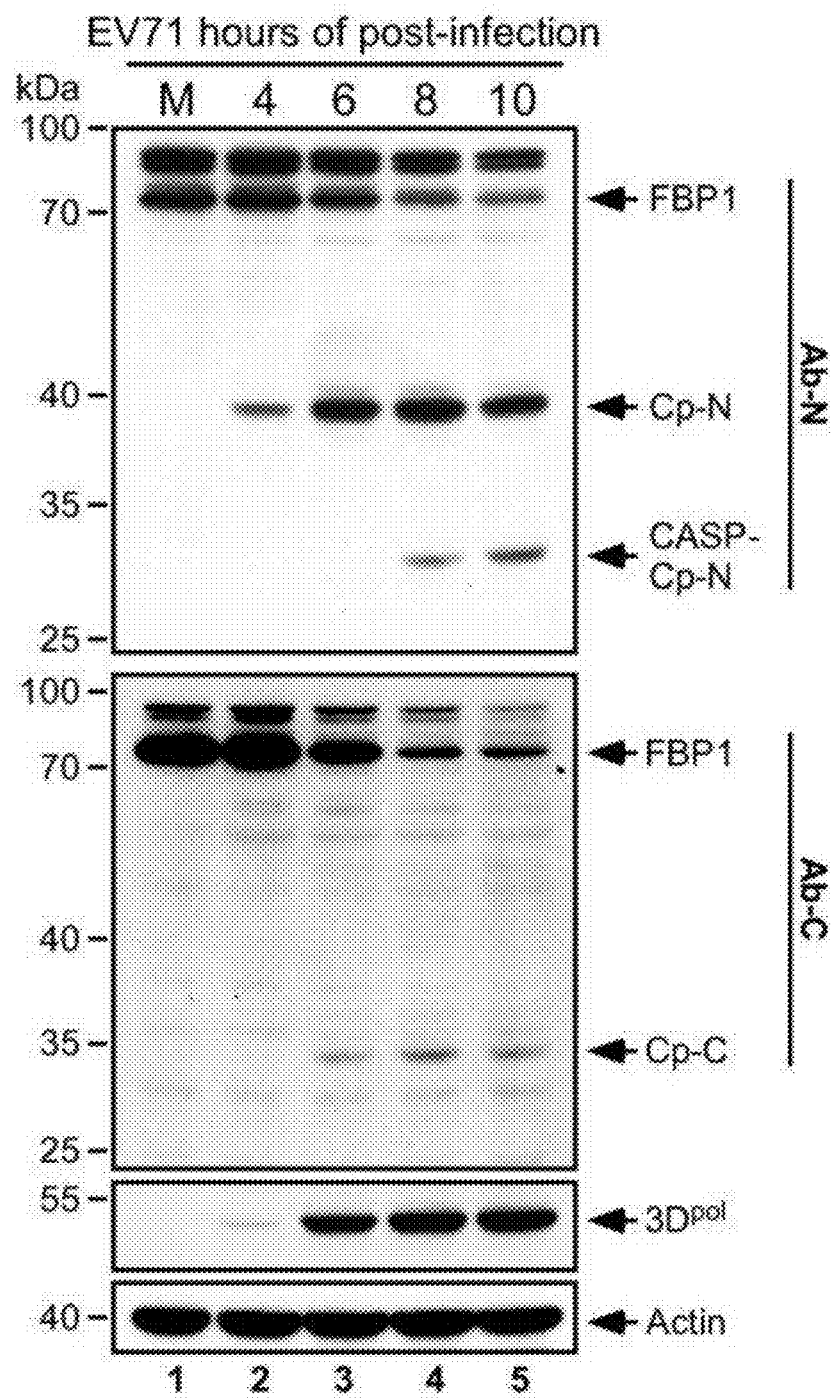
FIG. 2 shows the expression level of FBP1 protein and its cleavage products (Cp-N and Cp-C) in mock-infected or EV71-infected RD cells at 4, 6, 8 and 10 h.p.i. detected by Western blotting using two antibodies, Ab-N and Ab-C, that respectively recognize the N-terminal epitope (amino acid positions 61-80) and C-terminal epitope (amino acid positions 293-644) of FBP1, in which viral $3D^{pol}$ protein was used as an indicator for virus infection, actin served as a loading control, Cp-N and Cp-C respectively represent cleavage products including the N-terminal and C-terminal regions of FBP1, and CASP-Cp-N represents a caspase-induced cleavage product of Cp-N.

Results:

FIGS. 1 and 2 each illustrate immunoblot results showing expression of FBP1 in mock-infected cells and in EV71-infected cells at various designated time points of post-infection.

As shown in FIG. 1, decreased FBP1 expression was evident at 4 h.p.i., and the FBP1 level was significantly reduced at 8 and 10 h.p.i. In addition, a 38-kDa protein band, likely a cleavage product (Cp) of FBP1, appeared at 4 h.p.i. and reachedamaximal level at 6 h.p.i., and another potential 30-kDa Cp of FBP1 appeared at 8 and 10 h.p.i., demonstrating that EV71 infection destabilizes FBP1.

As shown in FIG. 2, FBP1 protein (72 kDa) could be cleaved by $2A^{pro}$ into two fragments, i.e. a 38-kDa (Cp-N) FBP1 cleavage product appearing at 4 h.p.i. and a 33-kDa (Cp-C) FBP1 cleavage product appearing at 6 h.p.i., which were respectively recognized by the Ab-N and Ab-C antibodies. In addition, a caspase-induced cleavage product from Cp-N (represented by CASP-Cp-N) was observed at 8 h.p.i.

Moreover, to further determine the subcellular localization of FBP1 in EV-71-infected cells, nuclear and cytoplasmic protein fractions were isolated from the total protein sample of the infected cells, and then subjected to immunoblot analysis. The results indicated that FBP1 remained primarily in the nucleus during mock infection, but appeared in the cytoplasm with an increasing level over 2 to 6 h.p.i. In contrast, the cleavage products of FBP1 were mostly present in the cytoplasm, and their expression levels increased throughout the course of infection (data not shown).

Taken together, these results demonstrate that the FBP1 protein is likely to be subjected to proteolytic cleavage during the middle stage of EV71 infection.

Example 2

Cleavage of FBP1 by EV71 Viral Proteinase 2A in Vitro

To determine whether FBP1 cleavage was caused by viral factors, [$^{35}$S] methionine-labeled FBP1 generated according to the procedures as described in the section, entitled "3. Coupled transcription/translation of [$^{35}$S] methionine-labeled FBP1," of the General Experimental Procedures was used in the following experiment.

Experimental Procedures:

A. In Vitro Proteinase Cleavage Assay with [$^{35}$S] Methionine-Labeled FBP1:

5 µL of the [$^{35}$S] methionine-labeled FBP1 protein was incubated with various doses (0, 0.5, 1, 2, 5 and 10 µg) of EV71 viral wild-type 2A proteinase ($2A^{pro}$) or incubated with 10 µg of a mutant 2A proteinase ($2A^{pro}$-C110S) in a cleavage buffer (50 mM Tris-HCl, 50 mM NaCl, 5 mM DTT and 1 mM EDTA; pH 7.5) with a total volume of 15 µL at 37° C. for 4 hours. The reaction products were analyzed by SDS-PAGE. After the electrophoresis, gel was removed from the electrophoresis apparatus and dried by Model 583 gel dryers (Bio-Rad) for 4 hours, and then the dried gel was loaded into an X-ray cassette with an X-ray film (Amersham Hyperfilm MP) in a darkroom for overnight exposure. Following the exposure, and the X-ray film was removed from the cassette for developing.

The applicants further examined the cleavage kinetics of FBP1 by incubating 5 µg of $2A^{pro}$ with [$^{35}$S] methionine-labeled FBP1, and then assayed the cleavage result at various time points (i.e., 15 min, 30 min, 1 hour, 2 hours and 4 hours). [$^{35}$S] methionine-labeled FBP1 incubated with 5 µg of $2A^{C110S}$ and without $2A^{pro}$, and [$^{35}$S] methionine-labeled FBP1 incubated without 5 µg of $2A^{C110S}$ and without $2A^{pro}$, were used as negative control groups.

Figure 3:
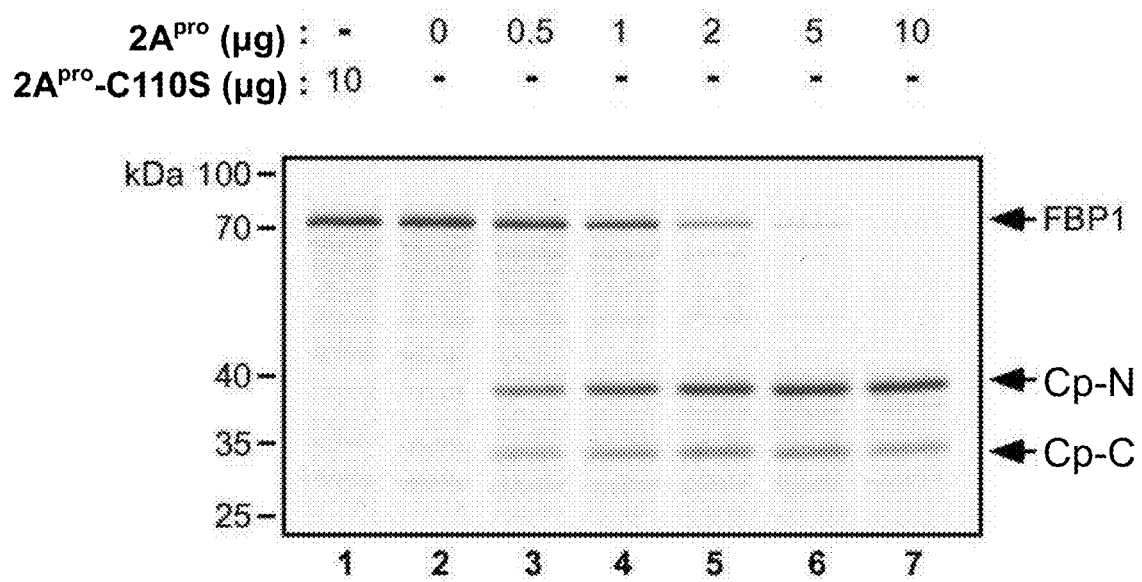
FIG. 3 shows the cleavage pattern of [$^{35}$S] methionine-labeled FBP1 induced by various doses of purified recombinant EV71 viral protease wild-type $2A^{pro}$ or the catalytic defective mutant $2A^{pro}$ ($2A^{pro}$-C110S) for 4 hours, in which Cp-N and Cp-C respectively represent cleavage products including the N-terminal and C-terminal regions of FBP1.

Results:

FIG. 3 shows the cleavage patterns of FBP1 by various doses of EV71 viral $2A^{pro}$. As shown in FIG. 3, FBP1 was cleaved by $2A^{pro}$ in a dose-dependent manner that resulted in two major Cps, a 38-kDa Cp designated as Cp-N, and a 33-kDa Cp designated as Cp-C.

In addition, it was found that Cp-N and Cp-C were detected after 15 minutes of incubation with $2A^{pro}$, and the levels of Cp-N and Cp-C increased over the 4 hours of incubation as observed (data not shown). These results provide evidence that the EV71 viral $2A^{pro}$ is capable of cleaving FBP1.

Example 3

Mapping of the EV71 $2A^{pro}$ Cleavage Site in FBP1

Previous studies on picornaviruses have revealed that $2A^{pro}$ preferentially cuts at glycine residues (Blom N. et al. (1996), *Protein Sci.*, 5:2203-2216; Hellen C. U. et al. (1992), *J Virol.*, 66:3330-3338), and the result in FIG. 2 indicated that FBP1 was cleaved into two fragments, the 38 kDa N-terminal cleavage product and the 33 kDa C-terminal cleavage product. Based on this observation, the applicants predicted that $2A^{pro}$ likely cuts at a glycine residue located among amino acid residues 345-380 of FBP1, as shown in Table 7 below. Therefore, to pinpoint the $2A^{pro}$ primary cleavage site in FBP1 and to further confirm that the cleavage occurs during EV71 infection, the following experiments were conducted.

Experimental Procedures:

A. In Vitro Proteinase Cleavage Assay with [$^{35}$S] Methionine-Labeled Wild-Type FBP1 and Mutant FBP1 Proteins:

[$^{35}$S] methionine-labeled wild-type FBP1 protein and seven mutant FBP1 proteins labeled with [$^{35}$S] methionine as shown in Table 7 were generated according to the procedures as described in the section, entitled "3. Coupled transcription/translation of [$^{35}$S] methionine-labeled FBP1," of the General Experimental Procedures.

TABLE 7

| FBP1 protein | Mutation sites among amino acid residues 345-380 of the respective mutant FBP1 protein |
|---|---|
| Wild-type FBP1 | SVQAGNPGGPGPGGRGRGRGQGNWNMGPPGGLQEFN |
| FBP1-G345-362K | SVQAKNPKKPKPKKRKRKRGQGNWNMGPPGGLQEFN |
| FBP1-G364-380K | SVQAGNPGGPGPGGRGRGRKQKNWNMKPPKKLQEFN |

TABLE 7-continued

| FBP1 protein | Mutation sites among amino acid residues 345-380 of the respective mutant FBP1 protein |
|---|---|
| FBP1-G364K | SVQAGNPGGPGPGGRGRGRK̲QGNWNMGPPGGLQEFN |
| FBP1-G366K | SVQAGNPGGPGPGGRGRGRGQ̲K̲NWNMGPPGGLQEFN |
| FBP1-G371K | SVQAGNPGGPGPGGRGRGRGQGNWNMK̲PPGGLQEFN |
| FBP1-G374K | SVQAGNPGGPGPGGRGRGRGQGNWNMGPPK̲GLQEFN |
| FBP1-G375K | SVQAGNPGGPGPGGRGRGRGQGNWNMGPPGK̲LQEFN |

Note:
The mutation sites are underlined; and the location of the predicted 2A$^{pro}$ cleavage sites are boldfaced.

These obtained [$^{35}$S] methionine-labeled proteins were subjected to in vitro proteinase cleavage assay using 10 μg of 2A$^{pro}$ at 37° C. for 4 hours according to the procedures as described in Example 2.

Figure 4:
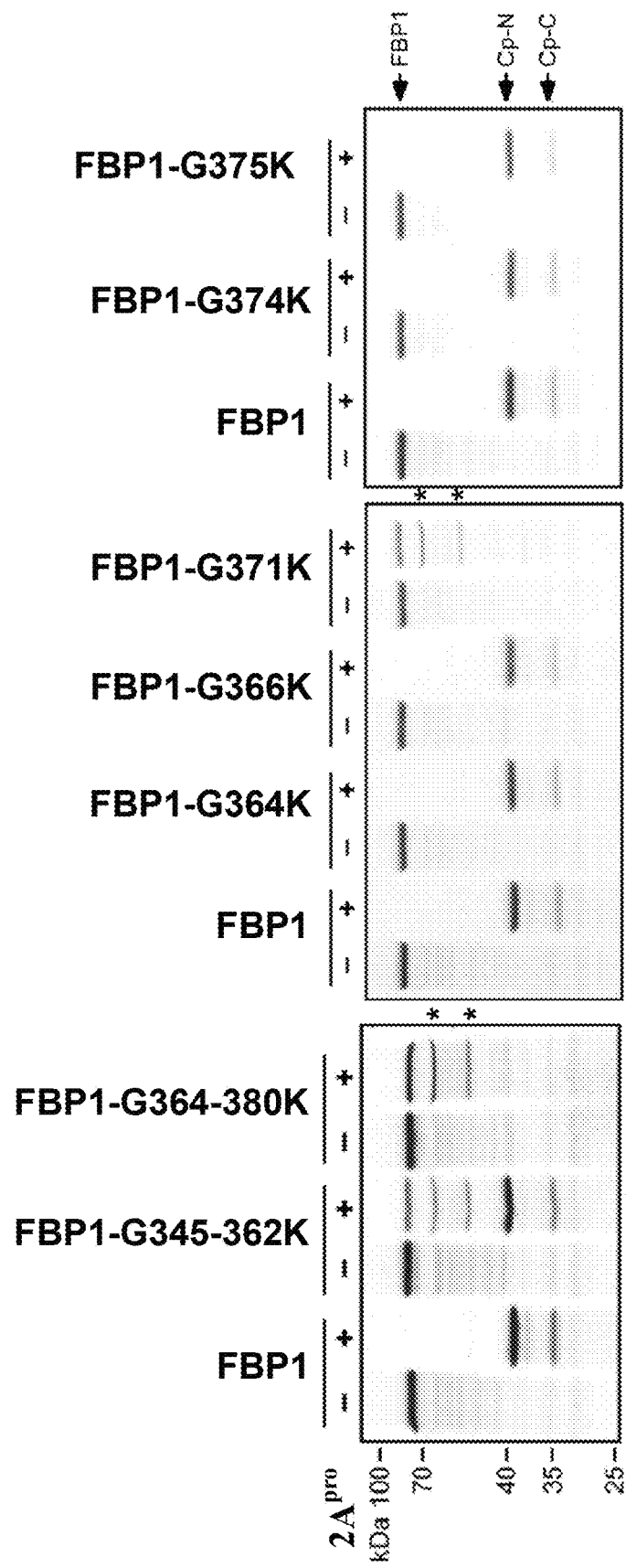
FIG. 4 shows the cleavage patterns of [$^{35}$S] methionine-labeled wild-type FBP1 and seven mutant FBP1 proteins labeled with [$^{35}$S] methionine (FBP1-G345-362K, FBP1-G364-380K, FBP1-G364K, FBP1-G366K, FBP1-G371K, FBP1-G374K and FBP1-G375K) induced by EV71 $2A^{pro}$ for 4 hours, in which non-specific cleavage products are indicated with an asterisk, and Cp-N and Cp-C represent cleavage products of FBP1 respectively including the N-terminal and C-terminal regions of FBP1.

Results:

It can be seen from FIG. 4 that in vitro 2A$^{pro}$ cleavage occurs on mutant FBP1-G345-362K with all the glycine residues mutated to lysine residues in the region spanning amino acid residues 345 to 362 but not on mutant FBP1-G364-380K with all the glycine residues mutated to lysine residues in the region spanning amino acid residues 364 and 380, indicating that the proteinase cleavage site is located within the region spanning amino acid residues 364 and 380. In addition, in comparison with FBP1-G364K, FBP1-G366K, FBP1-G374K and FBP1-G375K, FBP1-G371K could not be cleaved by 2A$^{pro}$, as shown by the absence of Cp-N and Cp-C cleavage products. These results indicate that Gly-371 residue of FBP1 is likely the primary cleavage site for EV71 viral proteinase 2A.

It should be noted that regarding FBP1-G345-362K, FBP1-G364-380K, and FBP1-G371K, there are two additional non-specific cleavage products with a higher molecular weight (indicated by asterisks) as compared to Cp-N and Cp-C fragments. These additional cleavage products were unlikely to represent the cleavage products or cleavage intermediates of 2A$^{pro}$, since they were not observed in the 2A$^{pro}$ cleavage profile of FBP1, as shown in FIG. 3. The applicants speculated that these non-specific cleavage products might have resulted from the introduction of glycine-to-lysine mutation, which may cause: either (i) the blockage of the primary cleavage site that forces 2A$^{pro}$ to cleave at alternative locations of FBP1, or (ii) conformational changes in FBP1 that lead to the exposure of alternative non-favored cleavage sites to 2A$^{pro}$.

Figure 5:
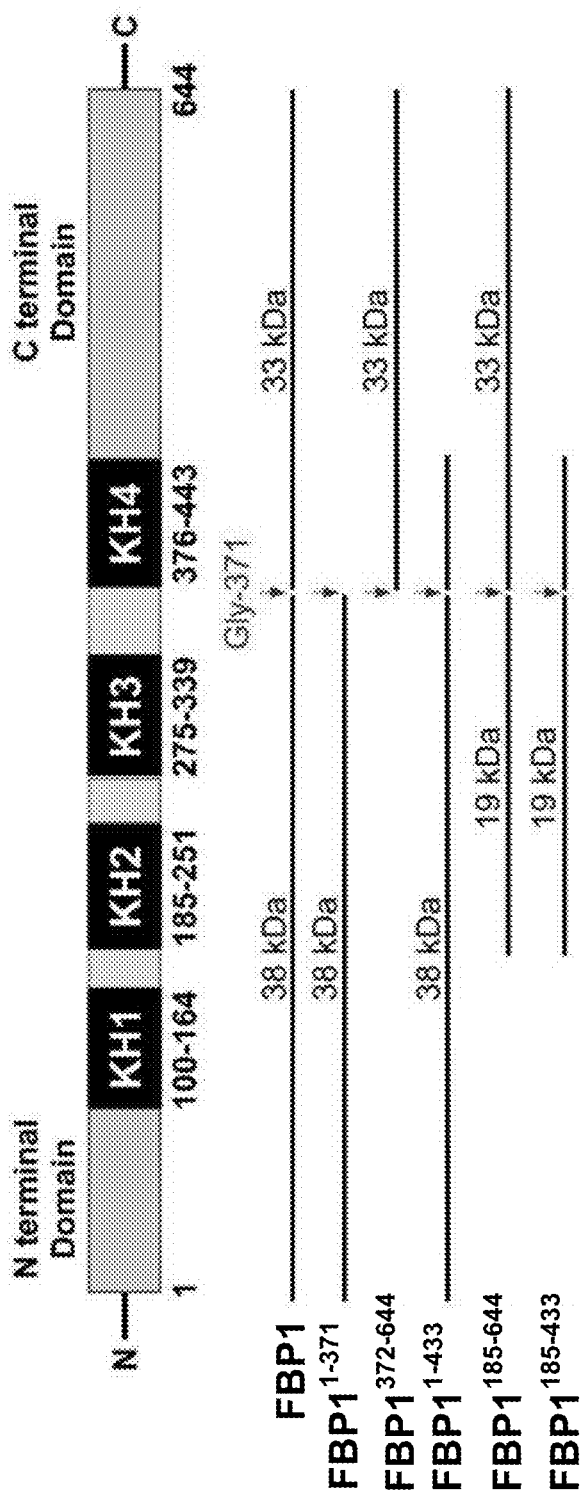
FIG. 5 is a schematic diagram showing predicted molecular weights of the cleavage products of wild-type FBP1 and five truncated FBP1 protein ($FBP1^{1-371}$, $FBP1^{372-644}$, $FBP1^{1-443}$, $FBP1^{185-644}$, and $FBP1^{185-443}$) at the proposed primary cleavage site at Gly-371 (indicated by an arrow), in which KH1 to KH4 represent the four K-homology (KH) domains of FBP1 for binding to DNA.

B. In Vitro Proteinase Cleavage Assay with [35S] Methionine-Labeled Wild-Type FBP1 and Truncated FBP1 Proteins:

In order to confirm whether Gly-371 is the only cleavage site of 2A$^{pro}$, [$^{35}$S] methionine-labeled wild-type FBP1 protein and five truncated FBP1 proteins labelled with [$^{35}$S] methionine (i.e., FBP1$^{1-371}$, FBP1$^{372-644}$, FBP1$^{1-443}$, FBP1$^{185}$-644 and FBP1$^{185}$-443) were produced according to the procedures as described in the section, entiled "3. Coupled transcription/translation of [$^{35}$S] methionine-labeled FBP1", of the General Experimental Procedures, followed by conducting in vitro proteinase cleavage assay as described above in section A of this example. FIG. 5 illustrates a schematic representation of wild-type FBP1 protein and the five truncated FBP1 proteins, together with the proposed primary cleavage site at Gly-371 (indicated by an arrow) and the molecular weights of the cleavage products for wild-type FBP1 protein and each truncated FBP1 protein.

Figure 6:
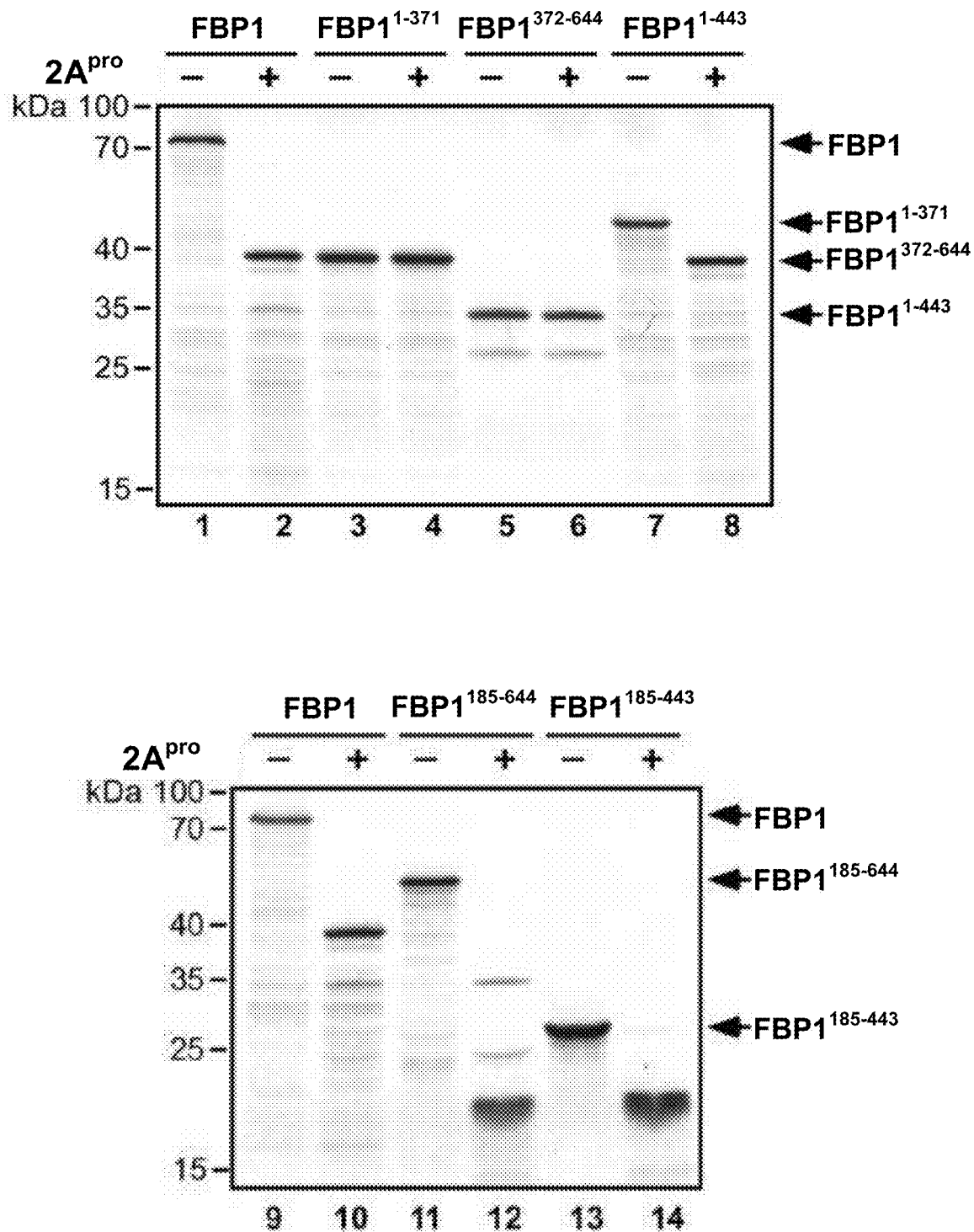
FIG. 6 illustrates the cleavage patterns of [35S] methionine-labeled wild-type FBP1 and five truncated FBP1 protein labeled with [$^{35}$S] methionine shown in FIG. 5 as induced by by EV71 $2A^{pro}$.

Results:

As shown in FIG. 6, both truncated FBP1$^{1-371}$ and FBP1$^{372-644}$ proteins were not cleaved by 2A$^{pro}$, and the molecular weights thereof were respectively 38 kDa and 33 kDa, which were consistent with those of Cp-N and Cp-C. In contrast, the remaining three FBP1 truncated proteins FBP1$^{1-443}$, FBP1$^{185-644}$ and FBP1$^{185-443}$ containing the Gly-371 cleavage site were cleaved by 2A$^{pro}$. In particular, a 38-kDa cleavage product was yielded from FBP1$^{1-443}$ (see lane 8), whereas both truncated FBP1$^{185-644}$ and FBP1$^{185-443}$ generated a similar 19-kDa cleavage product (see lanes 12 and 14), and FBP1$^{185-644}$ also yielded a 33-kDa product (see lane 12). Collectively, the cleavage patterns of wild-type and truncated FBP1 proteins indicate that Gly-371 residue of FBP1 might be the sole cleavage site of 2A$^{pro}$.

C. The Cleavage Profiles of Wild-Type FBP1 or Mutant FBP1-G371K in EV71-Infected RD Cells:

To further confirm that the cleavage of FBP1 occurs in vivo during EV71 infection, expression of FLAG-HA dual-tagged wild-type FBP1 and mutant FBP1-G371K (resistant to 2A$^{pro}$ cleavage) in RD cells was carried out, followed by EV71 infection.

To be specific, RD cells were transfected with pFLAG-FBP1-HA or pFLAG-FBP1-G371K-HA, and were then infected with EV71 according to the procedures as described in the preceding section, entitled "1. Virus infection," of the General Experimental Procedures.

At 4, 6, 8 and 10 h.p.i., the cell lysates from the mock-infected and EV71-infected cells were processed according to the procedures as described in Example 1. The total protein samples thus obtained were subjected to immunoblotting analysis according to the procedures as described in the preceding section, entitled "4. Immunoblot analysis," of the General Experimental Procedures. The primary and secondary antibodies used for detecting the respective protein in this example are shown in Table 8 below.

TABLE 8

| Proteins | Primary antibody | Secondary antibody |
|---|---|---|
| FLAG | Mouse anti-FLAG M2 monoclonal antibody (Cat. No. F3165, Sigma, St Louis, MO) | Amersham ECL Mouse IgG, HRP-linked whole Ab (from sheep) |
| HA | Mouse anti-HA monoclonal antibody (Cat. No. H9658, Sigma, St Louis, MO) | Amersham ECL Mouse IgG, HRP-linked whole Ab (from sheep) |
| EV71 3D$^{pol}$ | Mouse anti-3D$^{pol}$ monoclonal antibody (generated by the applicants) | Amersham ECL Mouse IgG, HRP-linked whole Ab (from sheep) |
| Actin | Mouse anti-actin antibody (Cat. No. MAB1501, Millipore, Billerica, MA) | Amersham ECL Mouse IgG, HRP-linked whole Ab (from sheep) |

Figure 7:
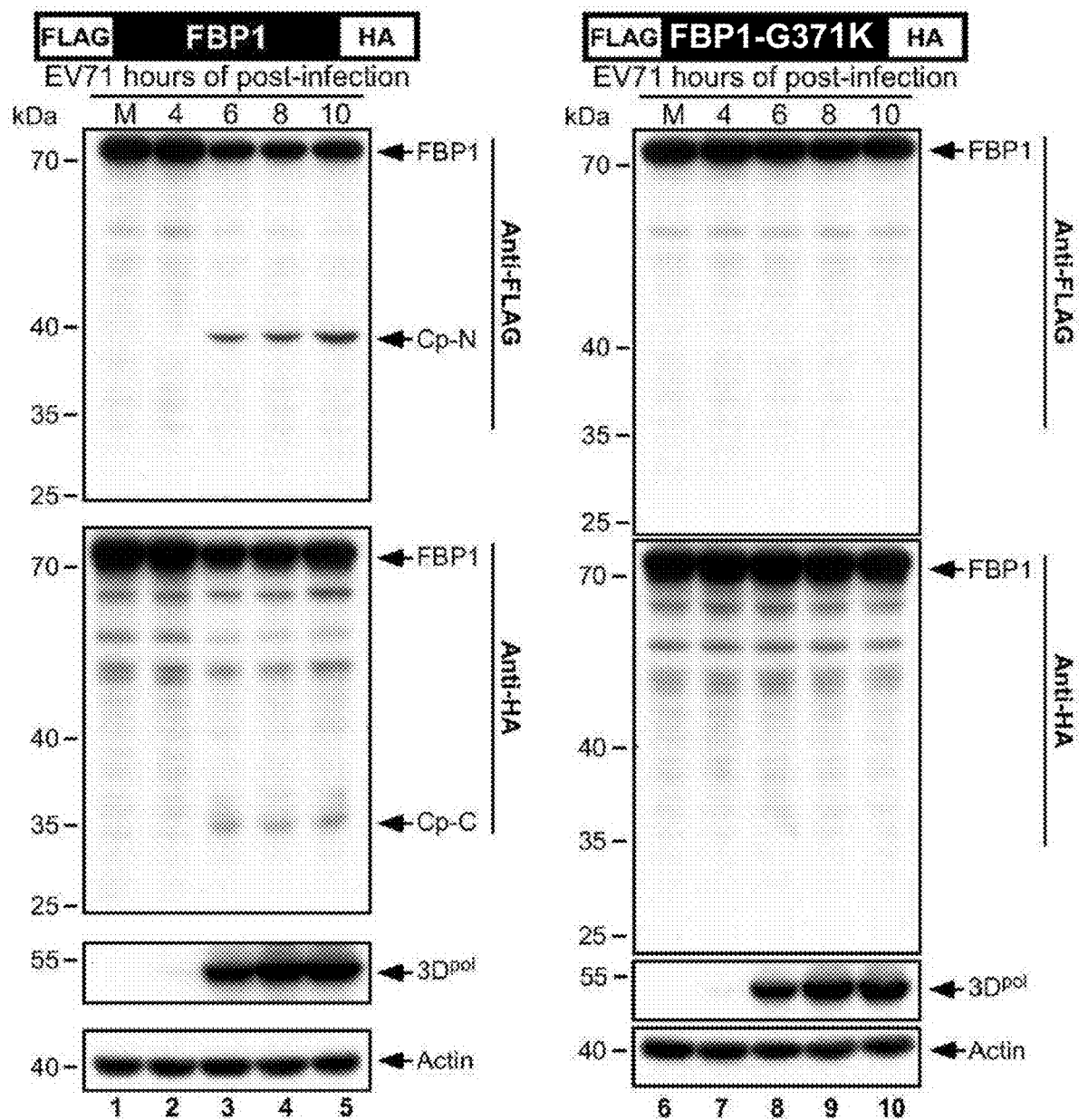
FIG. 7 illustrates the immunoblotting results showing the expressions of FBP1 protein and its cleavage products in RD cells transfected with a plasmid expressing FLAG-HA dual-tagged wild-type FBP1 protein or mutant FBP1-G371K protein, which is resistant to $2A^{pro}$ cleavage, after infection with EV71 for 4, 6, 8 and 10 hours, in which Cp-N and Cp-C represent cleavage products of FBP1 respectively containing the FLAG-tagged N-terminal region and HA-tagged C-terminal region of FBP1, viral $3D^{pol}$ protein was used as an indicator for virus infection, actin served as a loading control.

Results:

FIG. 7 illustrates the immunoblotting results showing the expression of FBP1 protein and its cleavage products in the EV71-infected RD cells overexpressing FLAG-HA dual-tagged wild-type FBP1 protein or mutant FBP1-G371K protein. As shown in FIG. 7, during the course of infection, FLAG-FBP1-HA was cleaved, and Cp-N and Cp-C cleavage products were respectively detected by anti-FLAG and anti-HA antibodies. On the contrary, FLAG-FBP1-G371K-HA mutant was resistant to 2A$^{pro}$ cleavage in vivo. The results confirm that FBP1 is cleaved at Gly-371 by viral 2A$^{pro}$ during the course of EV71 infection.

Example 4

Association of FBP1, FBP1$^{1-371}$ and EV71 5'UTR RNA

Figure 8:
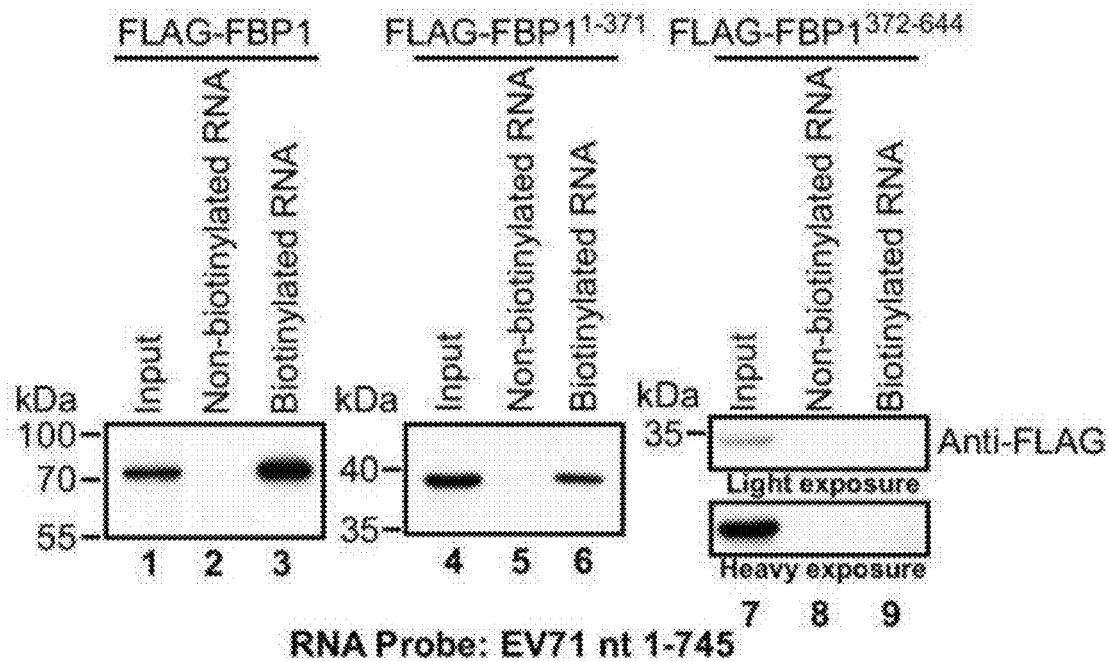
FIG. 8 illustrates the result of pull-down assay showing an association between an RNA probe (i.e., biotinylated or nonbiotinylated EV71 5' UTR (EV71 nucleotide positions 1-745), or biotinylated or nonbiotinylated EV71 5' UTR linker region (EV71 nucleotide positions 636-745)) and the cell lysate containing FLAG-tagged wild-type FBP1 or truncated FBP1 protein ($FBP1^{1-371}$ or $FBP1^{372-644}$)
Figure 8:
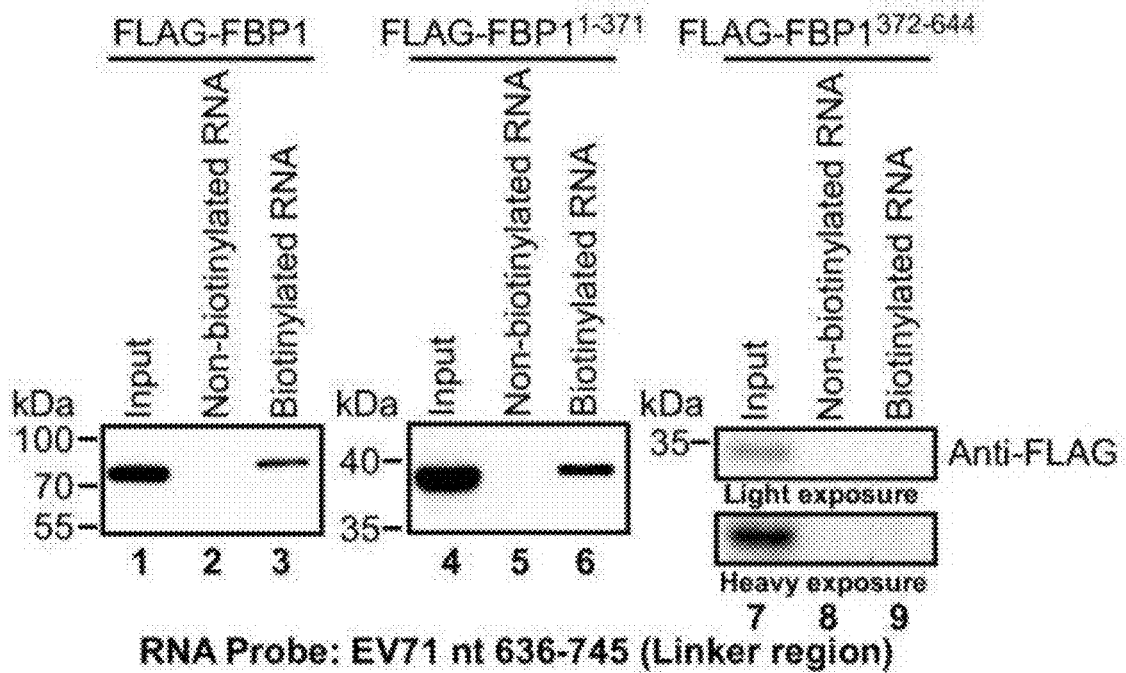
Figure 9:
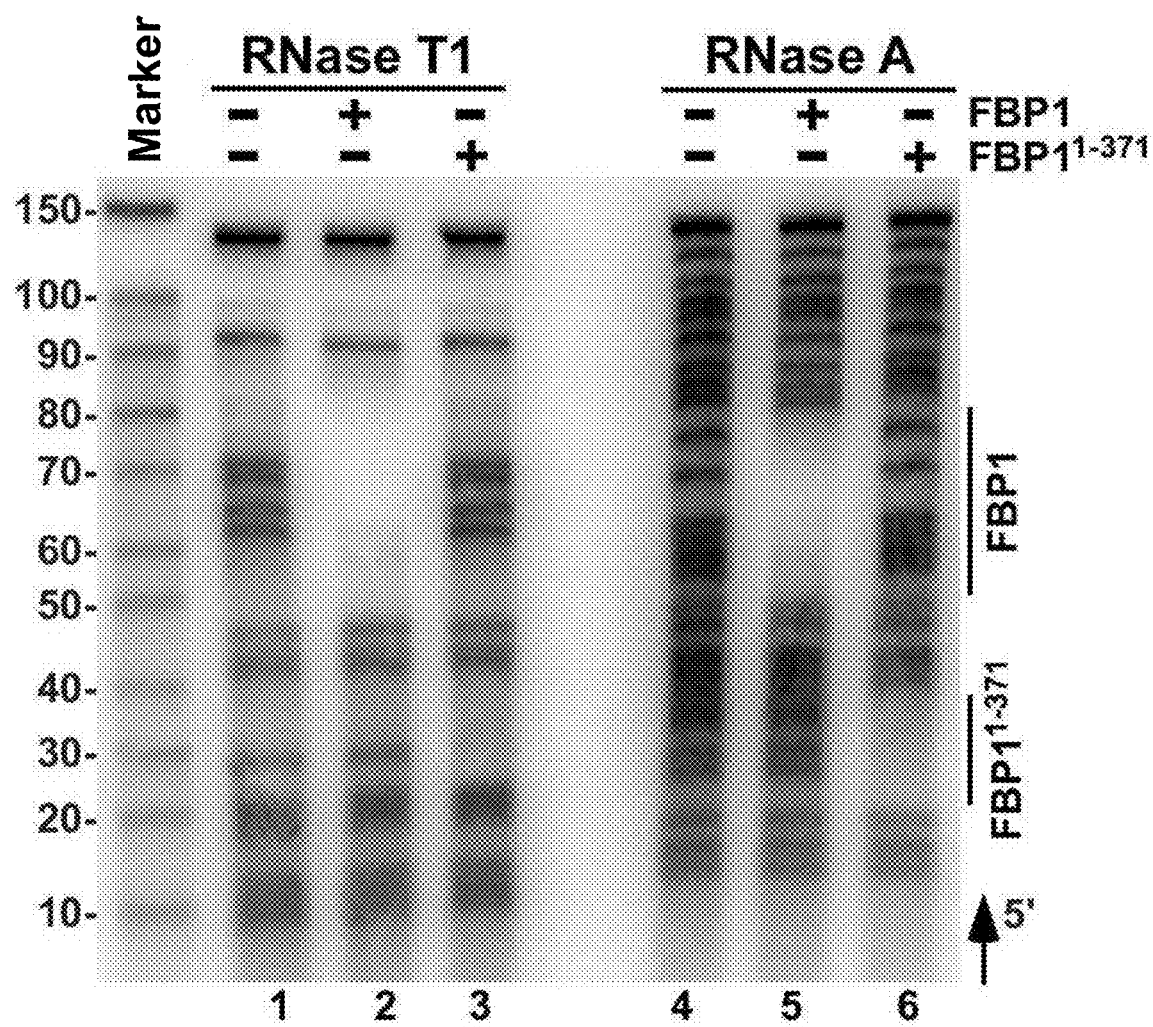
FIG. 9 illustrates the result of RNA footprinting assay showing a mapping association of wild-type FBP1 and truncated $FBP1^{1-371}$ protein with the EV71 5' UTR linker region RNA probe at the nucleotide sequence level as obtained using RNase T1 and RNase A.

To address the roles of cleaved FBP1 proteins in EV71 IRES activity, the following experiments were conducted.
Experimental Materials:
Plasmids pGL3-EV71 5'UTR-FLuc and pCRII-TOPO-EV71 5'UTR were constructed according to the methods described in Huang P. N. et al. (2011), supra and Lin J. Y. et al. (2009), supra.
A DNA fragment of T7-EV71 5'UTR containing T7 promoter and the EV71 5'UTR sequence (nucleotide positions 1-745 of EV71) was excised from recombinant plasmid pCRII-TOPO-EV71 5'UTR using a EcoRI restriction enzyme. In addition, a DNA fragment of T7-EV71 5'UTR linker region containing the T7 promoter and the EV71 5'UTR linker region sequence (nucleotide positions 636-745 of EV71) was amplified from pCRII-TOPO-EV71 5'UTR using a forward primer 5'-TAATACGACTCAC-TATAGGGCCATCCGGTGTGCAACAGGGCAAT-3' (SEQ ID No: 79) and a reverse primer 5'-GTTTGAT-TGTGTTGAGGGTCA-3' (SEQ ID NO: 80).
Each DNA fragment was transcribed into a respective RNA transcript (i.e., a respective one of EV71 5' UTR and EV71 5' UTR linker region RNA probes) using a MEGA-script T7 kit (ThermoFisher Scientific, San Jose, Calif.), according to the protocol recommended by the manufacturer. In addition, biotinylated RNA transcripts, i.e. biotinylated EV71 5'UTR and EV71 5'UTR linker region RNA probes, were synthesized by adding 1.25 μL of 10 mM biotin-16-UTP (Roche, Mannheim, Germany) in the transcription reaction. These RNA transcripts were purified using an RNeasy Mini kit (Qiagen, Chatsworth, Calif.).
Experimental Procedures:
A. Pull Down Assay for Biotinylated EV71 5' UTR RNA Probe with FLAG-Fused FBP1 Protein
RD cells were transfected with a respective one of pFLAG-CMV2-FBP1, pFLAG-CMV2-FBP 1$^{1-371}$ and pFLAG-CMV2-FBP1$^{372-644}$. At 48 hours post-transfection, the transfected cells were washed with PBS and lysed with a lysis buffer (containing 10 mM Tris-HCl (pH 7.4), 1 mM MgCl$_2$, 1 mM EGTA, 0.5% 3-[(3-cholamidopropyl)-dimethylammonio]-1-propanesulfonate (CHAPS), 10% glycerol, 0.1 mM phenyl-methylsulfonyl fluoride (PMSF) and 5 mM β-mercaptoethanol) for 30 minutes on ice. Afterwards, the resultant cell lysate was centrifuged at 10,000× g for 10 min at 4° C., and the supernatant thus formed was collected (to serve as an RD cell extract) and stored at −80° C. for further analysis.
The obtained RD cell extract (200 μg) was mixed with 12.5 pmol of a respective one of the following: biotinylated EV71 5'UTR RNA probe, non-biotinylated EV71 5'UTR RNA probe, biotinylated EV71 5' UTR linker region RNA probe and non-biotinylated EV71 5' UTR linker region RNA probe, followed by adding an RNA mobility buffer (5 mM HEPES (pH 7.1), 40 mM KCl, 0.1 mM EDTA, 2 mMMgCl$_2$, 2 mM dithiothreitol (DTT), 1 U RNasin, and 0.25 mg/mL heparin) until a final volume of 100 μL was reached. The resultant mixture was incubated at 30° C. for 15 minutes, and then added with 400 μL of streptavidin MagneSphere Paramagnetic Particles (Promega), followed by incubation for 10 minutes at room temperature, so as to pull down the biotinylated RNA-protein complex. The obtained pulled-down complex was washed 5 times with a heparin-free RNA mobility buffer, and then 25 μL of a 2× SDS sample buffer was added to the washed complex, followed by conducting incubation at 95° C. for 10 minutes to dissociate the proteins from the complex. The eluted protein sample was subjected to immunoblotting analysis with an anti-FLAG antibody as shown in Table 8.
B. Enzymatic RNA Footprinting Assay of Wild-Type FBP1 and FBP1$^{1-371}$ Bound to EV71 5' UTR Linker Region RNA
EV71 5' UTR linker region RNA probe synthesized in this example was labeled at the 5' end using T4 polynucleotide kinase and [γ-$^{32}$P] ATP.
The obtained $^{32}$P-labeled EV71 5' UTR linker region RNA probe was treated with 2 μg of wild-type FBP1 or 1.14 μg of FBP1$^{1-371}$ in a binding buffer containing 1 μL of 0.02 μg/μL RNAse A (a pyrimidine nucleotide-specific endonuclease, Ambion AM2274, Thermo Fisher Scientific) or 0.02 U/mL RNAse T1 (a ribonucleotide that specifically degrades single-stranded RNA at G residues, Ambion AM2283, Thermo Fisher Scientific) at 4° C. for 10 minutes, so as to degrade the RNA sequence without the protection of a bound protein. The RNA probe without incubation of an FBP1 protein served as a control group.
Reactions were terminated with 10 μL of an inactivation buffer (Ambion, Austin, Tex.), and the cleavage products were separated in 12% acrylamide/7M urea gels, after which the gels were dried and scanned with a phosphorimager (GE Typhoon Trio Imager Scanner). RNA nucleotide positions were determined through comparison with the Decade marker (Ambion), so as to identify the sequence protected by the wild-type FBP1 and FBP1$^{1-371}$.
Results:
A. Pull Down Assay
FIG. 8 illustrates immunoblot results showing association between FLAG-tagged FBP1, FBP1$^{1-371}$ and FBP1$^{372-644}$ with biotin-labeled or unlabeled EV71 5' UTR RNA probe and EV71 5' UTR linker region RNA probe. As shown in FIG. 8, both FLAG-FBP1 and FLAG-FBP1$^{1-371}$ incubated with biotinylated EV71 5' UTR RNA probe or EV71 5' UTR linker region RNA probe were pulled down by the streptavidin beads, and a parallel experiment showed that these proteins were not pulled down by the beads when non-biotinylated EV71 5' UTR RNA was used. In contrast, FLAG-FBP1$^{372-644}$ was not bound to EV71 5' UTR RNA probe or 5' UTR linker region RNA probe. These results indicate that both FLAG-FBP1 and FLAG-FBP1$^{1-371}$ can bind to the EV71 5' UTR, particularly the linker region thereof.
B. Enzymatic Footprinting Assay
FIG. 9 illustrates the result of the RNA footprinting assay (using RNase T1 and RNase A) showing a mapping association of wild-type FBP1 and mutant FBP1$^{1-371}$ protein with the EV71 5' UTR linker region RNA probe at the nucleotide sequence level. The vertical lines labeling the right side of the gel indicate nucleotides that were protected from RNase T1 and RNase A digestion in the presence of wild-type FBP1 and FBP1$^{1-371}$. As shown in FIG. 9, wild-type FBP1 was able to protect the EV71 5' UTR linker region RNA at nucleotide positions 686-714 (see lanes 2 and 5), while nucleotide positions 656-674 of the same linker region RNA was protected by FBP1$^{1-317}$ (see lanes 3 and 6).
Taken together, these results clearly demonstrate that wild-type FBP1 and FBP1$^{1-371}$ can bind to distinct sequences of the EV71 5'UTR linker region RNA.

Example 5

Evaluation for Role of FBP1$^{1-371}$ as an Additive ITAF to Enhance Viral IRES Activity To investigate whether FBP1$^{1-371}$ exhibits a comparable effect on in vitro EV71 IRES activity as wild-type FBP1, shFBP1-RD stable cells with sustained knockdown of endogeneous fbp1 gene expression were prepared and used in this example.

Experimental Materials:

Short hairpin RNA (shRNA) targeting nucleotide positions 847 to 871 of human FBP1 mRNA (shFBP1, 5'-CCAAGATTTGCTGTTGGCATTGTAA-3', SEQ ID No: 81) and the scramble control (shNC, 5'-AATTGCGCCCGCTTACCCAGTT-3' SEQ ID No: 82) were respectively inserted into lentivirus vectors pLKO_TRC005 (obtained from Taiwan National RNAi Core Facility, Academia Sinica) according to the instructions of the Taiwan National RNAi Core Facility, Academia Sinica, so as to construct two pLKO_TRC005-shRNA vectors, i.e. pLKO_TRC005-shFBP1 and pLKO_TRC005-shNC.

For lentivirus preparation, 293T cells were co-transfected with pLKO_TRC005-shFBP1 or pLKO_TRC005-shNC, and the helper plasmids pMD.G and pCMVAR8.91, using X-tremeGENE transfection reagent (Roche) and then cultured at 37° C. for 36 hr. The obtained cell culture was centrifugated under 300× g. The resultant supernatant containing viral particles was harvested.

RD cells were transduced with the obtained viral particles for 24 hours, and then subjected to selection with puromycin (5 µg/mL), so as to prepare shFBP1-RD stable cells with sustained knockdown of endogeneous fbp1 gene expression and shNC-RD stable cells.

Experimental Procedures:

The plasmid pGL3-EV71 5' UTR-FLuc was constructed according to the method described in Huang P. N. et al. (2011), supra and linearized using XhoI or XbaI restriction enzymes, so as to generate EV71 5' UTR-FLuc reporter RNA.

shFBP1-RD stable cells were grown in DMEM supplemented with 10% FBS, 100 units/mL of penicillin, 100 µg/mL of streptomycin and 0.25 µg/mL of amphotericin B, followed by cultivation in an incubator with culture conditions set at 37° C. and 5% CO$_2$. When reaching 90% of confluence, the cultured cells were washed and scraped with PBS, and then subjected to centrifugation at 300× g for 10 minutes at 4° C. After discarding the supernatant, the cell pellet thus obtained was resuspended in 1.5× pellet volume of a hypotonic lysis buffer (10 mM HEPES-KOH, pH 7.6, 10 mM KOAc, 0.5 mM Mg (OAc)$_2$, 2 mM DTT, and 1× protease inhibitor cocktail [Roche]), was placed on ice for 30 minutes, and was then homogenized with a 27-gauge ½-inch needle. The thus formed cell extract was centrifuged at 10,000× g for 20 minutes at 4° C., and the supernatant (serving as an shFBP1-RD extract) was recovered and used in the following in vitro IRES-driven translation assay to determine the impact of wild-type FBP1 and FBP1$^{1-371}$ on EV71 IRES-driven translation in vitro.

To be specific, a designated concentration (i.e., 0, 25, 50, 100 or 200 nM) of recombinant wild-type FBP1 or FBP1$^{1-371}$ obtained as described in Huang P. N. et al. (2011), supra was mixed with the following components to reach a final volume of 25 µL: 60% volume of the shFBP1-RD extract obtained above, 0.25 µg of EV71 5' UTR-Fluc RNA, 10 mM creatine phosphate, 50 µg/mL creatine phosphokinase, 79 mM KOAc, 0.5 mM Mg (OAc)$_2$, 2 mM DTT, 0.02 mM hemin, 0.5 mM spermidine, 20 mM HEPES-KOH (pH 7.6), 20 µM amino acid mixture (Promega), 0.4 mM ATP (Promega), and an RNase inhibitor. The mixture was incubated at 30° C. for 90 minutes, and firefly luciferase activity regarding each designated concentration of wild-type FBP1 or FBP1$^{1-371}$ was measured using luciferase assay system (Promega) and a luminometer (Promega). A mixture without recombinant wild-type FBP1 or FBP1$^{1-371}$ added was used as a buffer control and subjected to the same analysis, and the measured firefly luciferase activity was set as 100%.

The additive effect of wild-type FBP1 and FBP1$^{1-371}$ on EV71 IRES-driven translation in vitro was also generally examined using the same procedure as mentioned above, except that a designated concentration of recombinant wild-type FBP1 (50, 100 or 200 nM), FBP1$^{1-371}$ (50, 100 or 200 nM) or a combination of wild-type FBP1 and FBP1$^{1-371}$ (each at 25, 50 or 100 nM) was respectively used.

Figure 10:
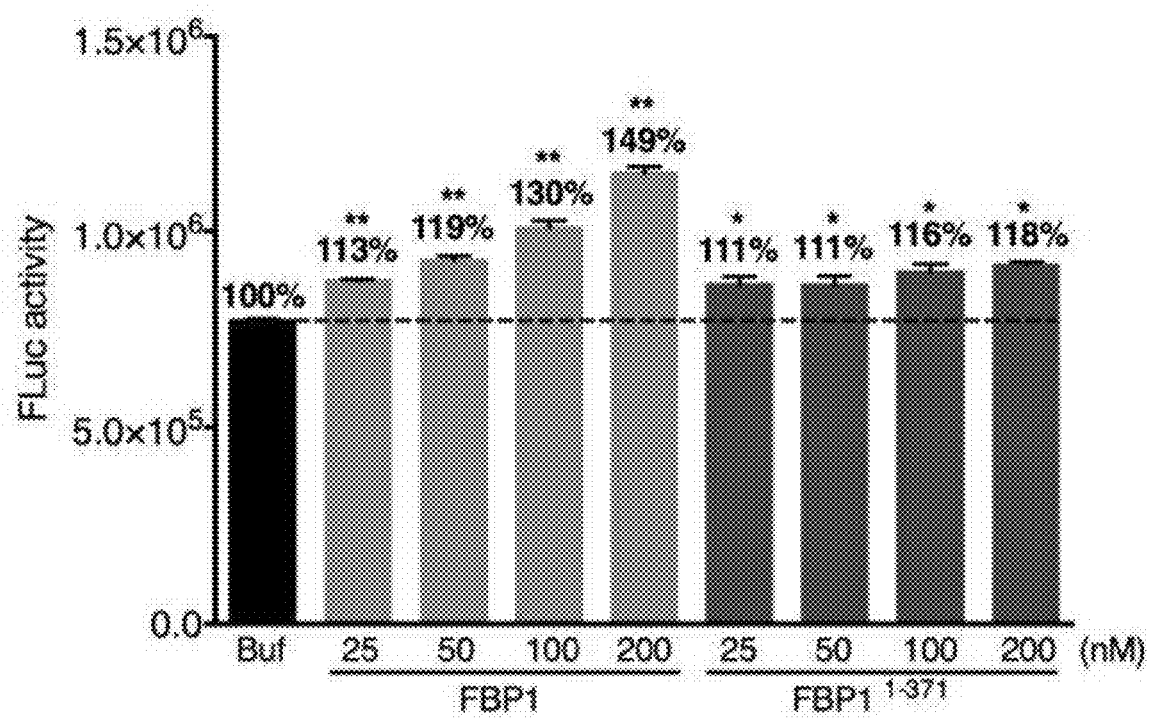
FIG. 10 illustrates the impact of various concentrations of wild-type FBP1 and truncated $FBP1^{1-371}$ on EV71 IRES-driven translation activity in vitro, in which the symbols "*" and "**" respectively represent p<0.05 and p<0.01 as compared to the buffer control.

Results:

FIG. 10 shows the the impact of various concentrations of wild-type FBP1 and FBP1$^{1-371}$ on EV71 IRES-driven translation activity in vitro. As shown in FIG. 10, adding recombinant wild-type FBP1 to an shFBP1-RD cell extract increased translation from an EV71 IRES reporter in a dose-dependent manner over the buffer control. In addition, IRES activity also increased due to the addition of recombinant FBP1$^{1-371}$.

Figure 11:
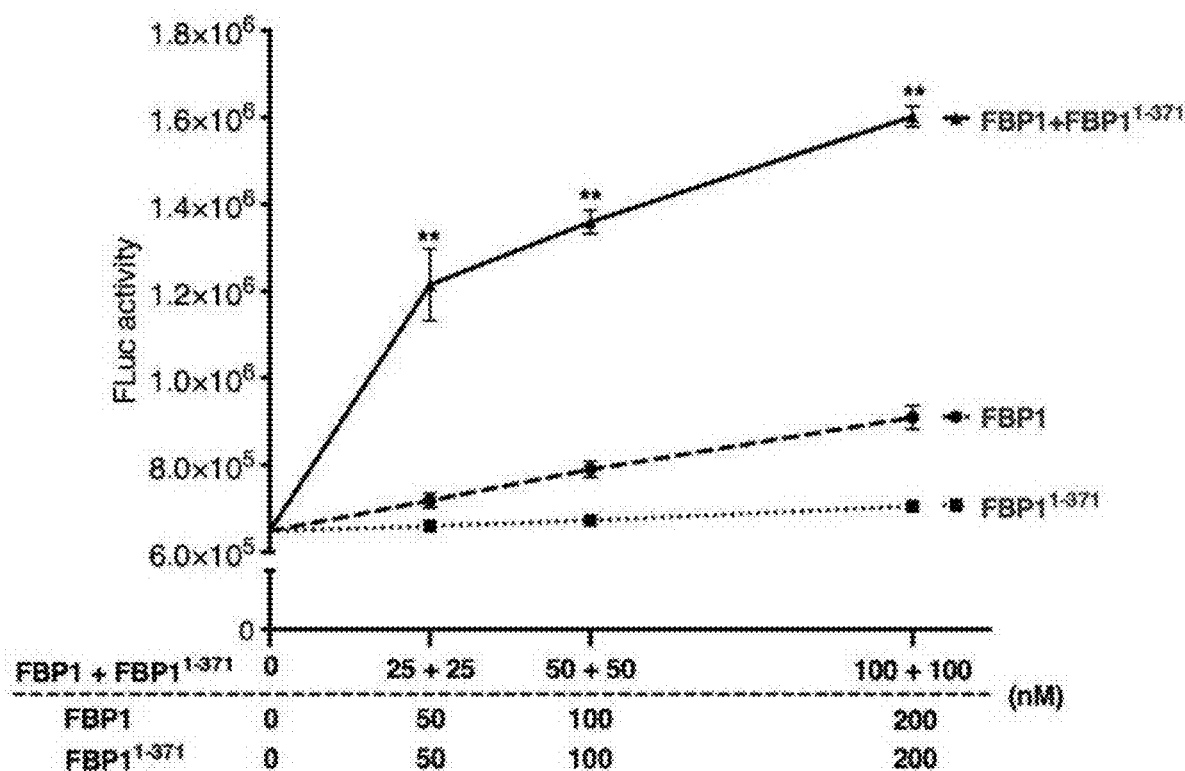
FIG. 11 illustrates the additive effect of wild-type FBP1 and truncated $FBP1^{1-371}$ on EV71 IRES-driven translation activity in vitro, in which the symbol "**" represents p<0.01 as compared to FBP1.

FIG. 11 illustrates the additive effect of wild-type FBP1 and FBP1$^{1-371}$ on EV71 IRES-driven translation activity in vitro. As shown in FIG. 11, when both wild-type FBP1 and FBP1$^{1-371}$ were added to an shFBP1-RD cell extract, EV71 IRES-driven translation was activated in a dose-dependent fashion, but more importantly, IRES activity was significantly increased at a level that was substantially higher than that seen in the reaction with wild-type FBP1 alone or FBP1$^{1-371}$ alone. These results demonstrate that in the presence of wild-type FBP1, FBP1$^{1-371}$ can act as an additive component to enhance EV71 IRES activity.

Example 6

Evaluation for Ability of FBP1$^{1-371}$ to Increase Viral Yield of Picornavirus To address whether the truncated FBP1 assists in affecting picornavirus (such as EV71 and CVB3) yielded in infected cells, four recombinant plasmids, including pFLAG-Hr-FBP1$^{WM}$ (expressing shRNA-resistant FLAG-FBP1$^{WM}$), pFLAG-Hr-FBP1-G371K$^{WM}$ (expressing shRNA-resistant and 2A$^{pro}$ cleavage-resistant FLAG-FBP1-G371K$^{WM}$), pFLAG-Hr-FBP1$^{1-371-WM}$ (expressing shRNA-resistant FBP1$^{1-371-WM}$) and pFLAG-Hr-FBP1$^{1-371-WM-delNLS}$ (expressing shRNA-resistant FBP1$^{1-371-WM-delNLS}$ with a deletion of nuclear localization signal (NLS) sequence from FBP1$^{1-371-WM}$), were used in the following experiment.

Experimental Procedures:

shFBP1-RD cells obtained in Example 5 were transiently transfected with pFLAG-CMV2 to serve as a vector control, or with the recombinant plasmid pFLAG-Hr-FBP1$^{WM}$ or pFLAG-Hr-FBP1-G371K$^{WM}$ to rescue FBP1 protein expression. At 48 hours post-transfection, the shFBP1-RD cells transfected with the respective plasmid as mentioned above and shNC-RD cells as obtained in Example 5 (as positive control) were infected with EV71 at a m.o.i. of 40 according to the procedures as described in the preceding section, entitled "1. Virus infection," of the General Experimental Procedures. EV71 viral titers during the course of infection, i.e. at 3, 6, 9 and 12 hours, were measured by plaque assays. In comparison, shNC-RD cells were subjected to the same analysis.

On the other hand, shFBP1-RD cells were co-transfected with: (1) pFLAG-Hr-FBP1-G371K$^{WM}$ and pFLAG-Hr-FBP1$^{1\text{-}371\text{-}WM}$, or (2) pFLAG-Hr-FBP1-G371K$^{WM}$ and pFLAG-Hr-FBP1$^{1\text{-}371\text{-}WM\text{-}delNLS}$. At 48 hours post-transfection, these two types of transfected cells, alone with the previously obtained shFBP1-RD cells transfected with pFLAG-CMV2 vector or pFLAG-Hr-FBP1-G371K$^{WM}$, were infected with EV71 or CBV3 at a m.o.i. of 40 according to the procedures as described in the preceding section, entitled "1. Virus infection," of the General Experimental Procedures. The EV71 and CBV3 viruses thus produced were harvested at 9 hours post-infection for determination of virus titers according to the procedures as described in the preceding section, entitled "5. Viral plaque assay," of the General Experimental Procedures. The viral titers in shFBP1-RD cells transfected with pFLAG-CMV2 vector was set as 100%.

Statistical significance of the experimental data was analyzed by performing one-way ANOVA using Prism 6 software (GraphPad Software, San Diego, Calif.), where p<0.05 was considered to be statistically significant.

Figure 12:
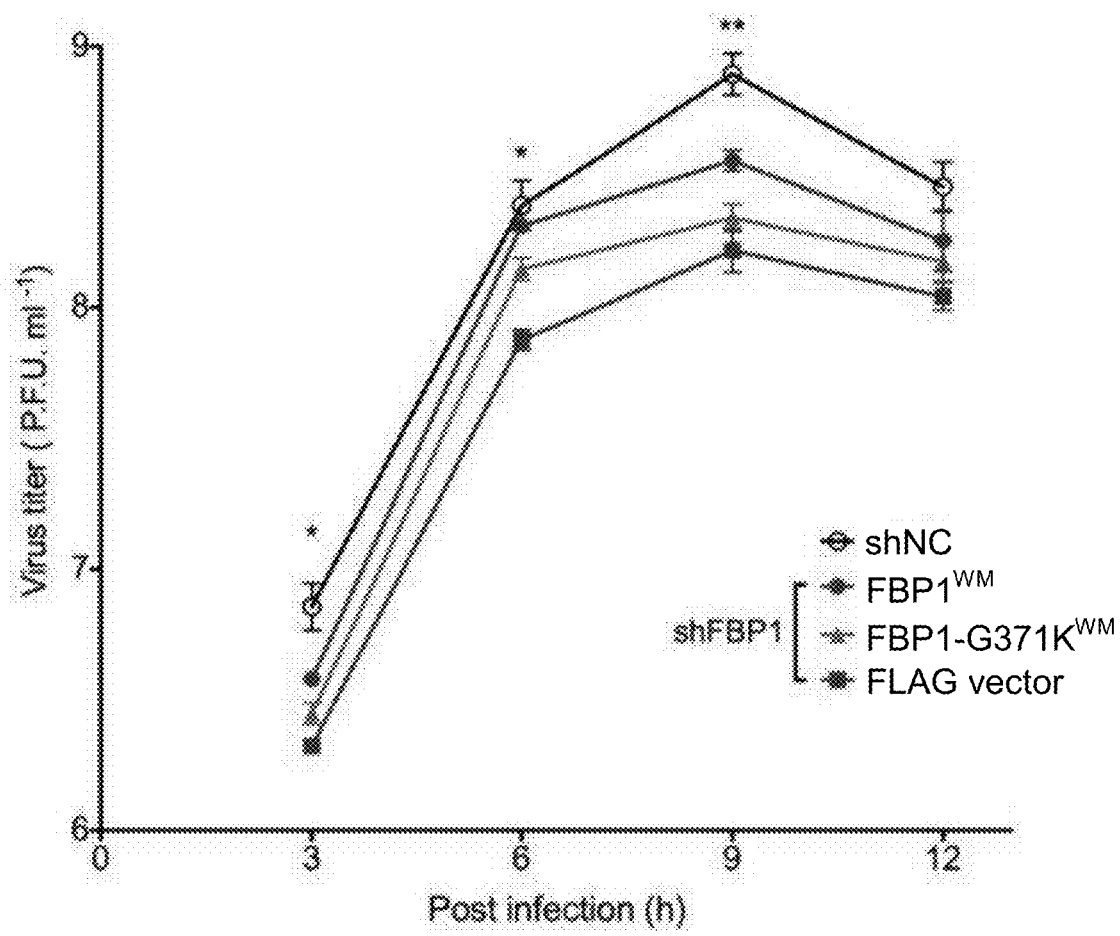
FIG. 12 shows the viral titers titrated by plaque assays in shNC-RD stable cells or in shFBP1-RD stable cells transfected with a vector control or plasmids expressing FLAG-tagged wobble mutant FBP1 ($FBP1^{WM}$) or $FBP1$-$G371K^{WM}$ after infection with EV71 at a m.o.i. of 40 for different time periods, in which the symbols "*" and "**" respectively represent p<0.05 and p<0.01.

Results:

FIG. 12 illustrates a line chart of the virus titers in EV71-infected shNC cells and shFBP1-RD cells expressing the FLAG-tag vector control, FBP1$^{WM}$ or FBP1-G371K$^{WM}$ measured as the number of plaque forming units per sample unit volume (pfu/mL), at 3, 6, 9, and 12 hours post-infection. As shown in FIG. 12, the expression of FBP1$^{WM}$ can partially restore viral titers at 6 and 9 hours post-infection as compared with shNC cells (with FBP1 expression) and shFBP1 cells transfected with the FLAG-tag vector control (without FBP1 expression). The expression of FBP1-G371K$^{WM}$ can also rescue viral titers at 6 and 9 hours post-infection, but to a lesser extent compared to FBP1$^{WM}$, indicating the additive effect of FBP1$^{1\text{-}371}$ in virus growth.

Figure 13:
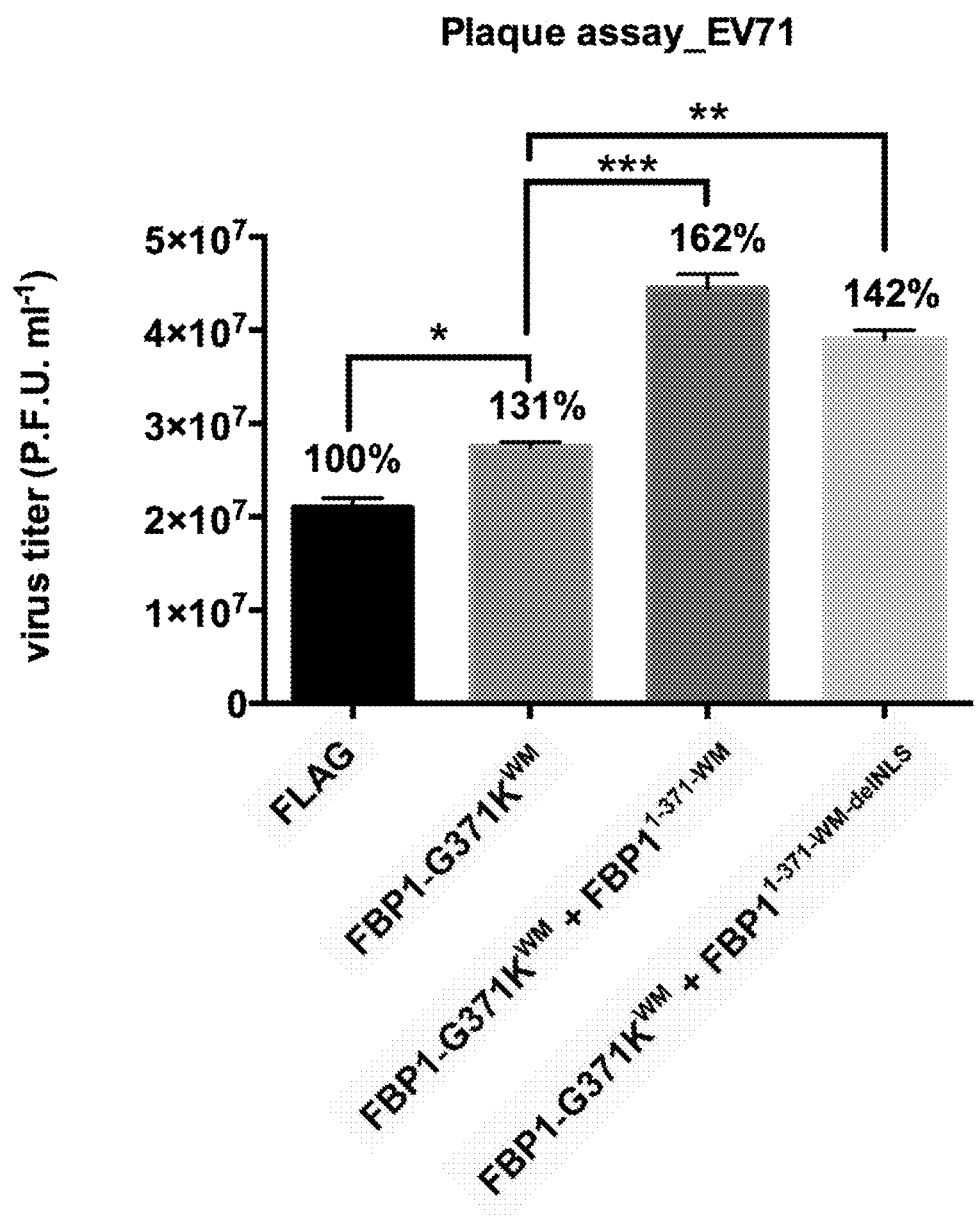
FIG. 13 shows the viral titers titrated by plaque assays in shFBP1-RD stable cells transfected with recombinant plasmids expressing different mutant FBP1 proteins after infection with EV71 at a m.o.i. of 40 for 9 hours, in which the symbols "*", "" and "*" respectively represent p<0.05, p<0.01 and p<0.001.
Figure 14:
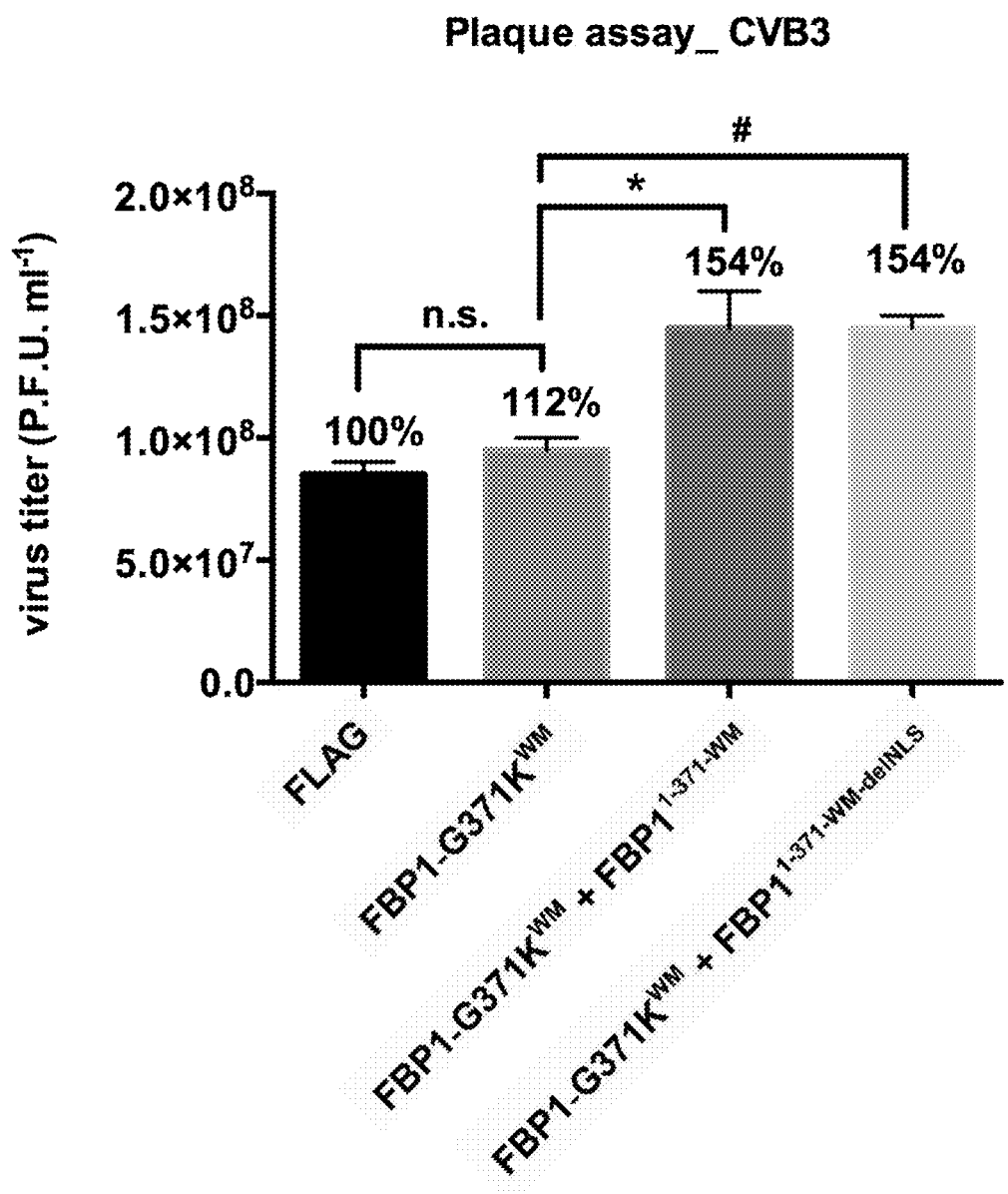
FIG. 14 shows the viral titers titrated by plaque assays in shFBP1-RD stable cells transfected with recombinant plasmids expressing different mutant FBP1 proteins after infection with CVB3 at a m.o.i. of 40 for 9 hours, in which symbols and "#" represent p<0.05, and the abbreviation "n.s." indicates non-significance.

FIGS. 13 and 14 respectively shows the virus titers (pfu/mL) of EV71 and CVB3 in infected shFBP1-RD cells overexpressing FLAG, FBP1-G371K$^{WM}$, FBP1-G371K$^{WM}$ along with FBP1$^{1\text{-}371\text{-}WM}$, and FBP1-G371K$^{WM}$ along with FBP1$^{1\text{-}371\text{-}WM\text{-}delNLS}$ at 6 hours post-infection. As demonstrated in FIG. 13, the expression of FBP1-G371K$^{WM}$ significantly increased EV71 viral yield as compared to the FLAG-tagged vector control. The coexpression of FBP1-G371K$^{WM}$ with FBP1$^{1\text{-}371\text{-}WM}$ or FB1$^{1\text{-}371\text{-}WM\text{-}delNLS}$ shows even higher increment in EV71 viral yield as compared to the FLAG control or FBP1-G371K$^{WM}$. Similarly, it is shown in FIG. 14 that, the coexpression of FBP1-G371K$^{WM}$ with FBP1$^{1\text{-}371\text{-}WM}$ or FBP1-G371K$^{WM}$ with FBP1$^{1\text{-}371\text{-}WM\text{-}delNLS}$ shows significant increase in the CVB3 viral yield in shFBP1-RD infected cells compared to the expression of FBP1-G371K$^{WM}$ or the FLAG-tagged vector control alone. These results indicate that the truncated FBP1, such as FBP1$^{1\text{-}371}$ and FBP1$^{1\text{-}371\text{-}delNLS}$ may play a key role in EV71 virus growth and yield.

Example 7

Evaluation for Roles of K109, K121, K122 as Potential Ubiquitination Sites in Fbp2

Figure 15:
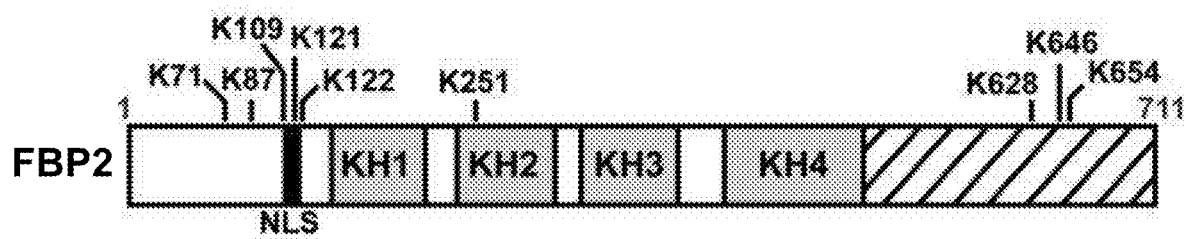
FIG. 15 is a schematic diagram of predicted ubiquitination sites in FBP2.

The applicants found that the ubiquitination of FBP2 is promoted by the KLHL12-based CUL3 ubiquitin E3 ligase complex (data not shown). In order to identify the main ubiquitination sites on FBP2 from those predicted via proteomics analysis (see FIG. 15), eight mutant FBP2 recombinant plasmids, including pFLAG-CMV2-FBP2-K109R, pFLAG-CMV2-FBP2-K251R, pFLAG-CMV2-FBP2-K628R, pFLAG-CMV2-FBP2-K646R, pFLAG-CMV2-FBP2-K654R, pFLAG-CMV2-FLAG-FBP2-K121,122R, pFLAG-CMV2-FBP2-N-ter-5K5R, and pFLAG-CMV2-FLAG-FBP2-K109, 121, 122R, along with the wild-type FBP2 recombinant plasmid pFLAG-CMV2-FBP2 were subjected to the following experiments.

Experimental Procedures:

A respective one of these wild-type FBP2 and mutant FBP2 recombinant plasmids was co-transfected with a plasmid pcDNA3-HA-Ub, which expressed HA tagged-ubiquitin (HA-Ub) and was provided by Dr. Rei-Lin Kuo (Chang Gung University, Taiwan) and Dr. Chen Zhao (University of Texas at Austin, USA), into 293T cells, using X-tremeGENE transfection reagent (Roche) according to the manufacturer's instructions. 293T cells transfected with pcDNA3-HA-Ub only served as a control group.

The transfected cells were treated with 20 μM MG132 (Sigma), followed by incubation for 4 hours. The cell culture was harvested and lysed with a lysis buffer containing 5 mM of N-ethylmaleimide (Sigma). The resultant cell lysate was immunoprecipitated with anti-FLAG M2 affinity gel. The immunoprecipitated product was subjected to immunoblotting according to the procedures as described in the preceding section, entitled "4. Immunoblot analysis," of the General Experimental Procedures, so as to detect the ubiquitinated FBP2 protein. In addition, actin was used as a loading control. The primary and secondary antibodies used for detecting the respective protein in this example are shown in Table 9 below.

TABLE 9

| Proteins | Primary antibody | Secondary antibody |
|---|---|---|
| FLAG-tagged FBP2 | Mouse anti-FLAG M2 monoclonal antibody | Amersham ECL Mouse IgG, HRP-linked whole Ab (from sheep) |
| HA-tagged protein (i.e., ubiquitinated FBP2 protein) | Mouse anti-HA monoclonal antibody | Amersham ECL Mouse IgG, HRP-linked whole Ab (from sheep) |
| Actin | Mouse anti-actin monoclonal antibody | Amersham ECL Mouse IgG, HRP-linked whole Ab (from sheep) |

In addition, the immunoblotting results (i.e. ubiquitination levels) of wild-type FBP2 and FBP2-K109, 121, 122R, FBP2-K121,122R and FBP2-K109R were each normalized by that of wild-type FBP2, so as to determine the fold-changes in ubiquitin modification.

Figure 16:
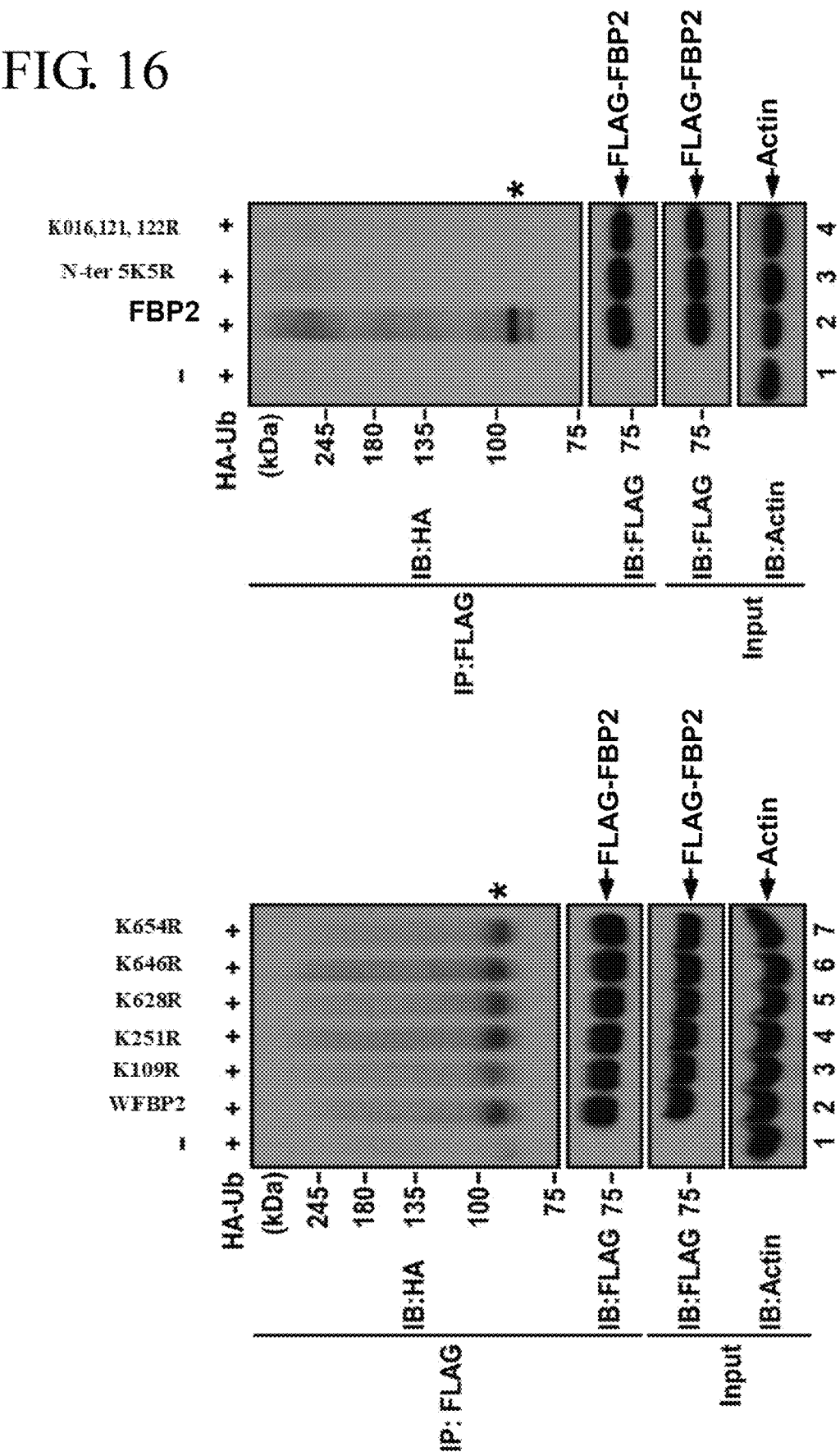
FIG. 16 shows the ubiquitination patterns of wild-type FBP2 and seven FBP2 mutants represented by K109R, K251R, K628R, K646R, K654R, N-ter 5K5R and K109, 121, 122R in 293T cells co-transfected with a plasmid expressing HA-tagged ubiquitin (HA-Ub), in which the asterisk (*) represents the major modification (ubiquitination) of FBP2.

Results:

As shown in the left panel of FIG. 16, the ubiquitination level of FBP2-K109R was decreased in comparison to wild-type FBP2 (see lanes 2 and 3), however, this result was not seen for FBP2-K251R, FBP2-K628R, FBP2-K646R, or FBP2-K654R (see lanes 4-7).

Figure 17:
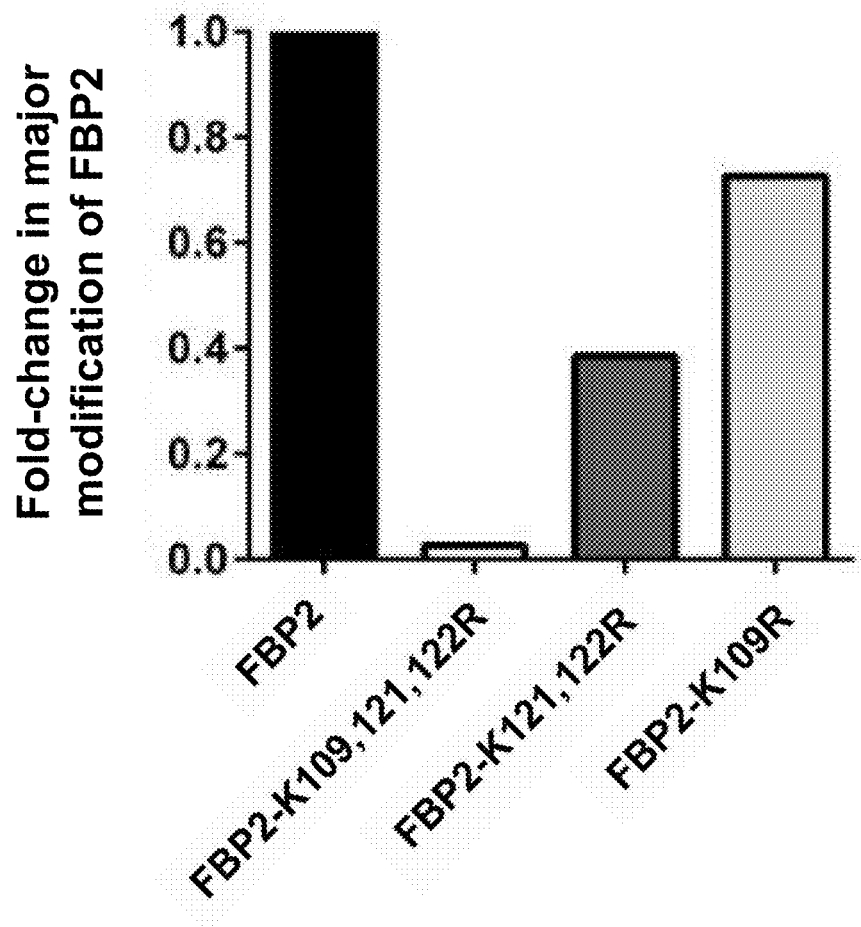
FIG. 17 shows the fold-changes in the major modification (ubiquitination) of wild-type FBP2 and three FBP2 mutants represented by K109, 121, 122R, K121,122R and K109R compared to that of wild-type FBP2 protein.

In addition, it can be seen from the right panel of FIG. 16, as well as FIG. 17, that the ubiquitination levels of FBP2-K121,122R (with two lysine residues at amino acid positions 121 and 122 replaced with arginine), FBP2-N-ter-5K5R (with five lysine residues at amino acid positions 71, 87, 109, 121 and 122 replaced with arginine), and FBP2-K109, 121, 122R (with three lysine residues at amino acid positions 109, 121 and 122 replaced with arginine) were all decreased in comparison to wild-type FBP2. Furthermore, FBP2-K121,122R had a lower ubiquitination level as compared to FBP2-K109R, but the ubiquitination level of FBP2-

K109, 121, 122R remained lower than that of FBP2-K121, 122R. This result indicates that the ubiquitination level of mutant FBP2 decreases when the number of mutation sites at amino acid positions 109, 121 and 122 of FBP2 increases.

Therefore, the applicants contemplate that Lys109, Lys121 and Lys122 are the likely sites for KLHL12-mediated ubiquitination in FBP2.

Example 8

Assessment for Importance of Ubiquitination on FBP2 Downregulation of IRES-Driven Translation To assess the impact of ubiquitinated FBP2 on EV71 5' UTR RNA-driven translation and to investigate how FBP2 ubiquitination affects the viral protein synthesis, shFBP2-RD stable cells with sustained knockdown of endogeneous fbp2 gene expression were prepared and used in this example.

Experimental Materials:

shFBP2-RD stable cells with sustained knockdown of endogeneous fbp2 gene expression were prepared by the procedures similar to that of shFBP1-RD stable cells as described in Example 5, except that the short hairpin RNA (shRNA) used was shFBP2 targeting nucleotide positions 813 to 837 of human FBP2 mRNA (5'-CACATTCGTAT-TCTGAGATCCGTCC-3', SEQ ID No: 83). In comparision, the pLKO.1-shLacZ control plasmid TRCN0000072224 (provided by Taiwan National RNAi Core Facility, Academia Sinica) was used to prepare shLacZ-RD stable cells without knockdown of endogenous fbp2 gene expression.

Experimental Procedures:

shFBP2-RD stable cells were grown in DMEM supplemented with 10% FBS, 100 units/mL of penicillin, 100 μg/mL of streptomycin and 0.25 μg/mL of amphotericin B, followed by cultivation in an incubator with culture conditions set at 37° C. and 5% $CO_2$. When reaching 90% of confluence, the cultured cells were washed and scraped with PBS, and were then subjected to centrifugation at 300× g for 10 minutes at 4° C. After discarding the supernatant, the cell pellet thus obtained was resuspended in 1.5× pellet volume of a hypotonic lysis buffer (10 mM HEPES-KOH, pH 7.6, 10 mM KOAc, 0.5 mM $Mg(OAc)_2$, 2 mM DTT, and 1× protease inhibitor cocktail [Roche]), was placed on ice for 30 minutes, and was then homogenized with a 27-gauge ½-inch needle. The thus formed cell extract was centrifuged at 10,000× g for 20 minutes at 4° C., and the resultant supernatant (serving as an shFBP1-RD cell translation extract) was recovered and used in the following in vitro IRES-driven translation assay.

293T cells were co-transfected with (1) the recombinant plamids pFLAG-CMV2-FBP2 and pcDNA3-HA-Ub or (2) pFLAG-CMV2-FBP2-K109, 121, 122R and pcDNA3-HA-Ub, using the X-tremeGENE transfection reagent. At 48 hours post-transfection, the transfected cells were harvested using a lysis buffer (50 mM Tris-HCl, pH 7.4, with 150 mM NaCl, 1 mM EDTA, and 1% Triton-X-100) and placed on ice for 30 min. The resultant cell lysate was centrifuged at 12,000× g for 10 min, and the obtained supernatant was incubated with anti-FLAG M2 affinity gel (Sigma) at 4° C. for 16 hours. After washing five times with a wash buffer (50 mM Tris-HCl, pH 7.4, with 150 mM NaCl), the immunoprecipitated complex thus obtained was eluted with 3× FLAG peptides, so as to obtain an eluted product containing a FLAG-tagged ubiquitinated FBP2 protein.

For in vitro IRES-driven translation assay, the obtained eluted FLAG-tagged FBP2 protein (250 ng) was mixed with the following conponents to reach a final volume of 25 μL: 15 μL of the shFBP2-RD cell translation extract obtained above, 0.25 μg of EV71 5' UTR-FLuc reporter RNA as prepared in Example 5, a translation mixture (10 mM creatine phosphate, 50 μg/mL creatine phosphokinase, 79 mM KOAc, 0.5 mM Mg $(OAc)_2$, 2 mM DTT, 0.02 mM hemin, 0.5 mM spermidine), 20 mM HEPES-KOH (pH 7.6), 20 μM amino acid mixture (Promega), 0.4 mM ATP (Promega) and an RNase inhibitor. The mixture thus formed was incubated at 30° C. for 90 min and then measured for firefly luciferase activity using the luciferase assay system (Promega).

The aforesaid experiments were conducted in triplicate, and the results were subjected to statistical analysis using Student's two-tailed unpaired t-test using Prism 6 software (GraphPad Software, San Diego, Calif.) where $p<0.05$ was considered to be statistically significant.

Figure 18:
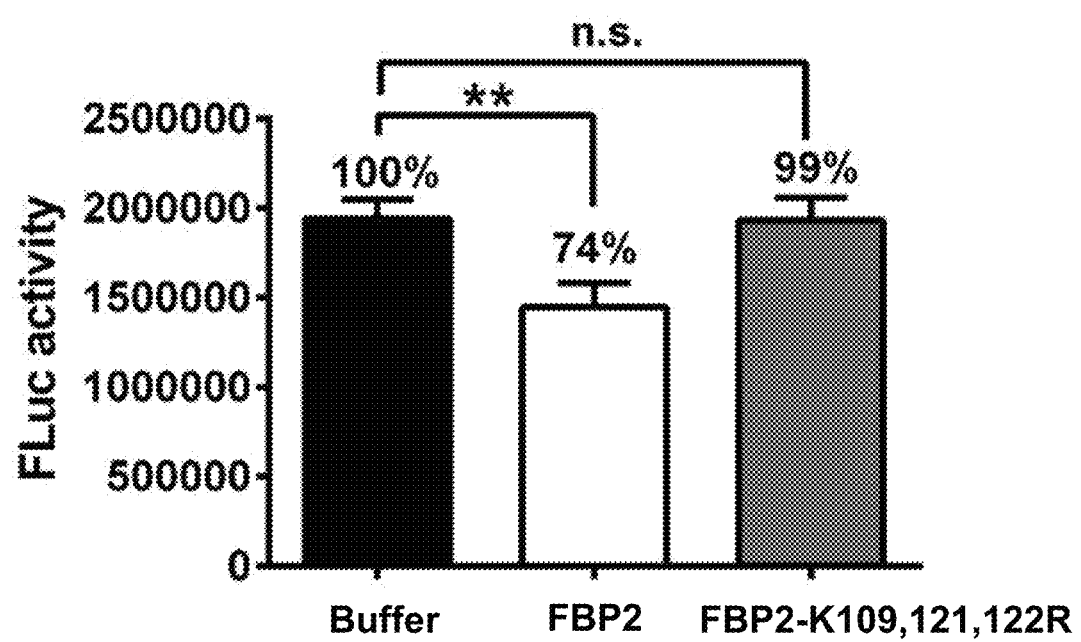
FIG. 18 shows the impact of various concentrations of wild-type FBP2 and FBP2-K109, 121, 122R on EV71 IRES-driven translation activity in vitro, in which the abbreviation "n.s." indicates non-significance, and the symbol "**" represents p<0.01.

Results:

FIG. 18 is a bar chart showing the luciferase activity of the buffer control, ubiquitinated wild-type FBP2, and FBP2-K109, 121, 122R with reduced ubiquitination. As shown in FIG. 18, as compared to the buffer control, the IRES-driven translation by the ubiquitinated wild-type FBP2 was significantly decreased, whereas no significant difference was observed in FBP2-K109, 121, 122R with reduced ubiquitination. The result indicates that the ubiquitination of FBP2 is essential for its downregulatory effect on EV71 IRES-driven translation. In other words, the mutant FBP2 proteins having at least one of the lysine residues K109, K121 and K122 that are mutated to arginine could be effective in enhancing viral IRES-driven translation activity.

Example 9

Evaluation for Influence of Ubiquitination Status on the Capability of FBP2 to Compete Against FBP1

It was noted in Example 8 that both wild-type FBP2 and the reduced ubiquitination variant (i.e. FBP2-K109, 121, 122R) can associate with the EV71 5'UTR RNA. To further confirm whether the competitive capability of FBP2 against other positive ITAFs (such as FBP1) is affected by ubiquitination, the following experiments were conducted.

Experimental Procedures:

RD cells were transfected with the recombinant plasmid pFLAG-CMV2-FBP2 or pFLAG-CMV2-FBP2-K109, 121, 122R using the X-tremeGENE transfection reagent (Roche). At 48 hours post-transfection, the transfected cells were washed with PBS and lysed with a lysis buffer (containing 10 mM Tris-HCl (pH 7.4), 1 mM $MgCl_2$, 1 mM EGTA, 0.5% CHAPS, 10% glycerol, 0.1 mM PMSF and 5 mM β-mercaptoethanol) for 30 minutes on ice. Afterwards, the resultant cell lysate was centrifuged at 10,000× g for 10 min at 4° C., and the supernatant thus formed was collected (serving as an RD cell extract) and stored at −80° C. for further analysis.

The obtained RD cell extract (200 μg) was mixed with the following components to reach a final volume of 100 μL: 12.5 pM of the biotinylated EV71 5'UTR RNA probe as obtained in Example 4, different concentrations (0, 0.5, 1 and 2 μM) of recombinant His-tagged wild-type FBP1, and an RNA mobility shift buffer (5 mM HEPES (pH 7.1), 40 mM KCl, 0.1 mM EDTA, 2 mM $MgCl_2$, 2 mM DTT and 0.25 mg/mL heparin). After incubation at 30° C. for 15 min, the thus formed mixture containing protein-biotinylated RNA complexes was added to 400 μL of Streptavidin Magne-Sphere Paramagnetic Particles (Promega) for capturing at room temperature for 10 min. The captured product thus obtained was washed five times with a heparin-free RNA mobility shift buffer, after which 30 μL of a 2× sample buffer was added, followed by incubation for 10 min at room temperature to dissociate the protein-biotinylated RNA complexes. The thus formed sample containing the eluted protein was incubated at 95° C. for 5 min and then subjected to immunoblotting according to the procedures as described in the preceding section, entitled "4. Immunoblot analysis," of the General Experimental Procedures. The primary and secondary antibodies used for detecting the respective protein in this example are shown in Table 10 below.

TABLE 10

| Proteins | Primary antibody | Secondary antibody |
| --- | --- | --- |
| FLAG-tagged FBP2 | Mouse anti-FLAG M2 monoclonal antibody (Cat. No. F3165, Sigma-Aldrich, St Louis, MO) | Amersham ECL Mouse IgG, HRP-linked whole Ab (from sheep) |
| His-tagged FBP1 | Mouse anti-His monoclonal antibody (Cat. No. OB05, CalBioChem, LaJolla, CA) | Amersham ECL Mouse IgG, HRP-linked whole Ab (from sheep) |

Figure 19:
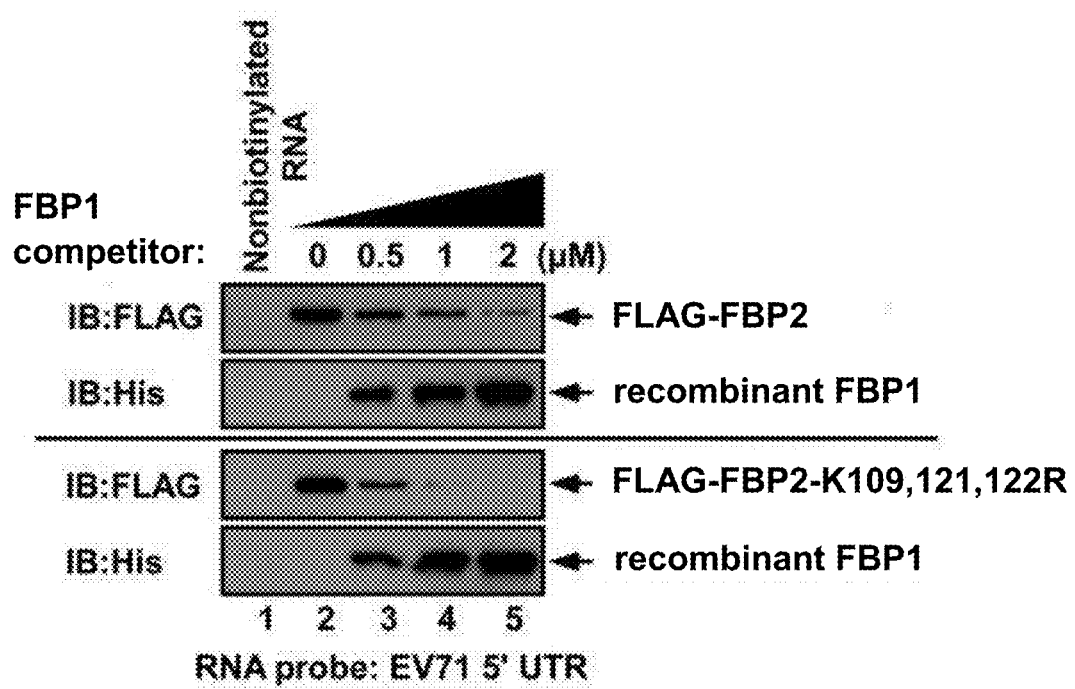
FIG. 19 shows the competitive capability of different concentrations of a recombinant FBP1 protein against wild-type FBP2 and FBP2-K109, 121, 122R in interacting with biotinylated EV71 5'UTR RNA probe.

Results:

FIG. 19 shows the result of the immunoblot assay evaluating the EV71 5' UTR RNA competition dynamics for wild-type FBP2, FBP2-K109, 121, 122R and the positive ITAF FBP1. As shown in FIG. 19, increasing amounts of FBP1 competed against both wild-type FBP2 and FBP2-K109, 121, 122R for binding to EV71 5' UTR RNA. In addition, under the same amount of FBP1, FBP2-K109, 121, 122R was more significantly outcompeted for binding to the EV71 5' UTR as compared to wild-type FBP2. On the other hand, a reverse competition assay using wild-type FBP2 or FBP2-K109, 121, 122R against FBP1 was also conducted, and the results suggest that increasing levels of wild-type FBP2 and FBP2-K109, 121, 122R outcompeted FBP1 for binding to EV71 5'UTR RNA (data not shown). Taken together, these results demonstrate that reduction of FBP2 ubiquitination may diminish the competitive capability of FBP2 against FBP1 for binding to EV71 5'UTR RNA, thereby suppressing the inhibitory effect of FBP2 on EV71 IRES-driven translation.

Example 10

Evaluation for Ability of Mutant FBP2 with Reduced Ubiquitination to Increase EV71 Viral Yield In order to investigate how the ubiquitination of FBP2 affects EV71 and CVB3 virus yield in infected RD cells, the following experiments were conducted.

Experimental Procedures:

A. Determination of Viral Protein Synthesis shFBP2-RD cells obtained in Example 8 were transfected with a respective one of pFLAG-CMV2 vector as a vector control, pFLAG-CMV2-FBP2 and pFLAG-CMV2-FBP2-K109, 121, 122R.

At 24 hours post-transfection, 2.5×10$^5$ transfected cells were seeded into each well of a 12-well plate and incubated at 37° C. for additional 24 hours. The obtained cell culture was infected with EV71 at a m.o.i. of 10 according to the procedures as described in the preceding section, entitled "1. Virus infection," of the General Experimental Procedures. The medium was replaced with methionine-free DMEM, and incubation was continued at 37° C. for 1 hour. Afterwards, the medium was replaced with DMEM containing [$^{35}$S]-methionine (50 μCi/mL) to label the newly synthesized viral proteins. After 1 hour of labeling, the cells were washed with PBS and lysed with a lysis buffer (150 mM NaCl, 50 mM Tris-Base, 1% IGEPAL CA630 (octylphenoxy poly(ethyleneoxy) ethanol), pH 8.0). The cell lysate was centrifuged at 10000× g for 10 min at 4° C. The resultant supernatant was subjected to SDS-PAGE, followed by transfer to a PVDF membrane and detection by autoradiography and immunoblotting.

Viral proteins seen from autoradiography were identified according to the protein size. The levels of [$^{35}$S]-methionine-labeled VP1 and 3C$^{pro}$ proteins were quantified and normalized against the actin level, based on two repeated experiments.

B. Plaque Assay shFBP2-RD cells as obtained in Example 8 were transfected with a respective one of the following plasmids: pFLAG-CMV2 as a vector control, pFLAG-CMV2-FBP2, pFLAG-CMV2-FBP2-K109, 121, 122R, pFLAG-CMV2-FBP2-K109R, pFLAG-CMV2-FBP2-K121R and pFLAG-CMV2-FBP2-K122R. After incubation at 37° C. for 2 days, the transfected cells were subjected to virus infection with EV71 or CVB3 virus at a m.o.i. of 40 according to the procedures as described in the preceding section, entitled "1. Virus infection," of the General Experimental Procedures. The EV71 and CVB3 viruses thus produced were harvested at 9 hours post-infection, and the virus titers were titrated according to the procedures as described in the preceding section, entitled "5. Viral plaque assay," of the General Experimental Procedures. The virus titer in the FLAG vector control was set as 100%.

Statistical significance of the experimental data was analyzed by performing one-way ANOVA using Prism 6 software (GraphPad Software, San Diego, Calif.), where $p<0.05$ was considered to be statistically significant.

Figure 20:
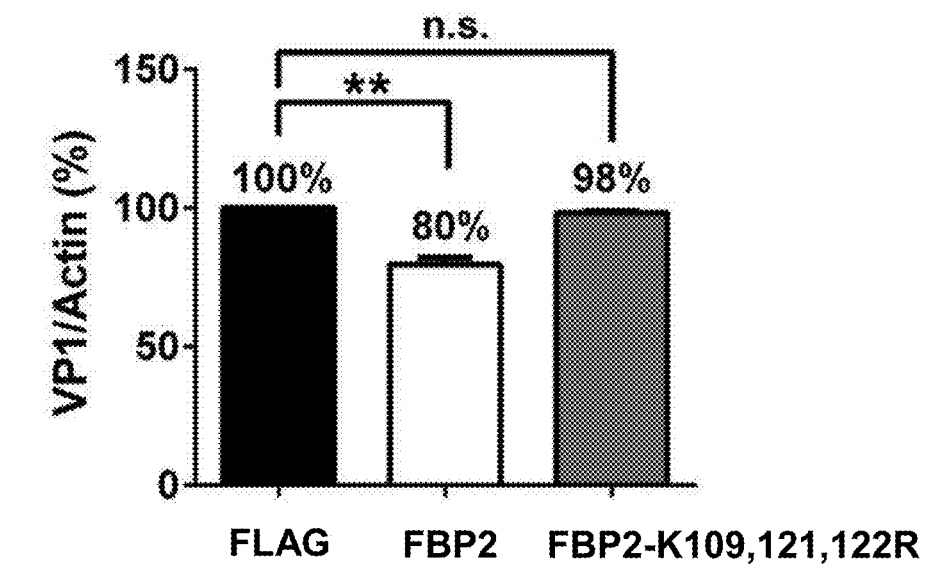
FIG. 20 shows the relative expression levels of VP1 and $3C^{pro}$ against actin in shFBP2-RD stable cells overexpressing wild-type FBP2 and FBP2-K109, 121, 122R after infection with EV71 at 10 m.o.i. for 5-6 hours, in which the abbreviation "n.s." indicates non-significance, and the symbol "**" represents p<0.01.
Figure 20:
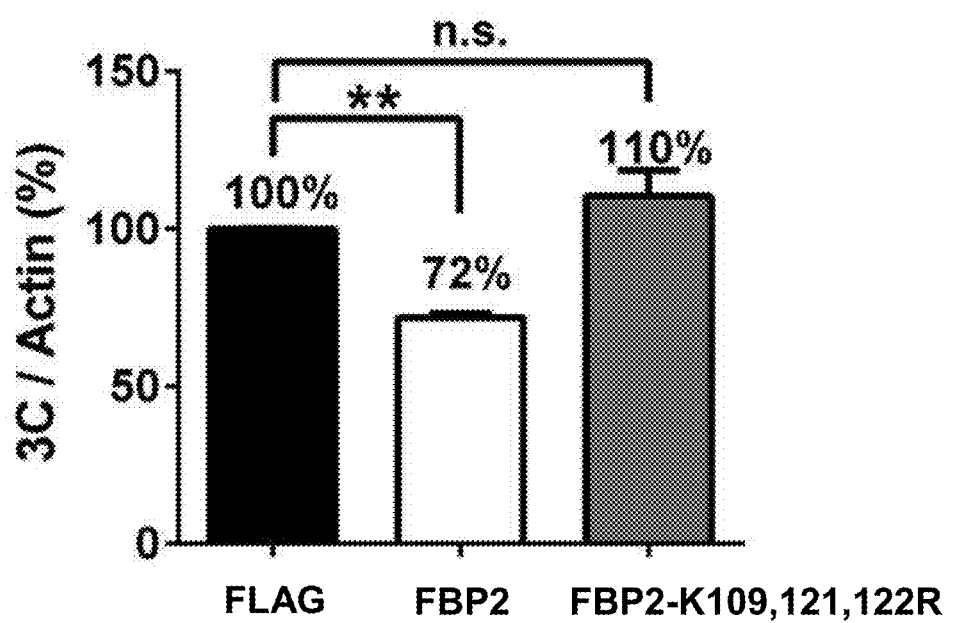

Results:

FIG. 20 illustrates the relative expression levels of newly synthesized viral proteins VP1 and 3C$^{pro}$ against the actin level in the shFBP2-RD cells overexpressing the FLAG vector control, wild-type FBP2 and mutant FBP2-K109, 121, 122R with reduced ubiquitination. As shown in FIG. 20, the relative expression levels of VP1 and 3C$^{pro}$ were significantly lower in the wild-type FBP2-expressing cells as compared to those in the cells expressing the FLAG vector control and FBP2-K109, 121, 122R.

Figure 21:
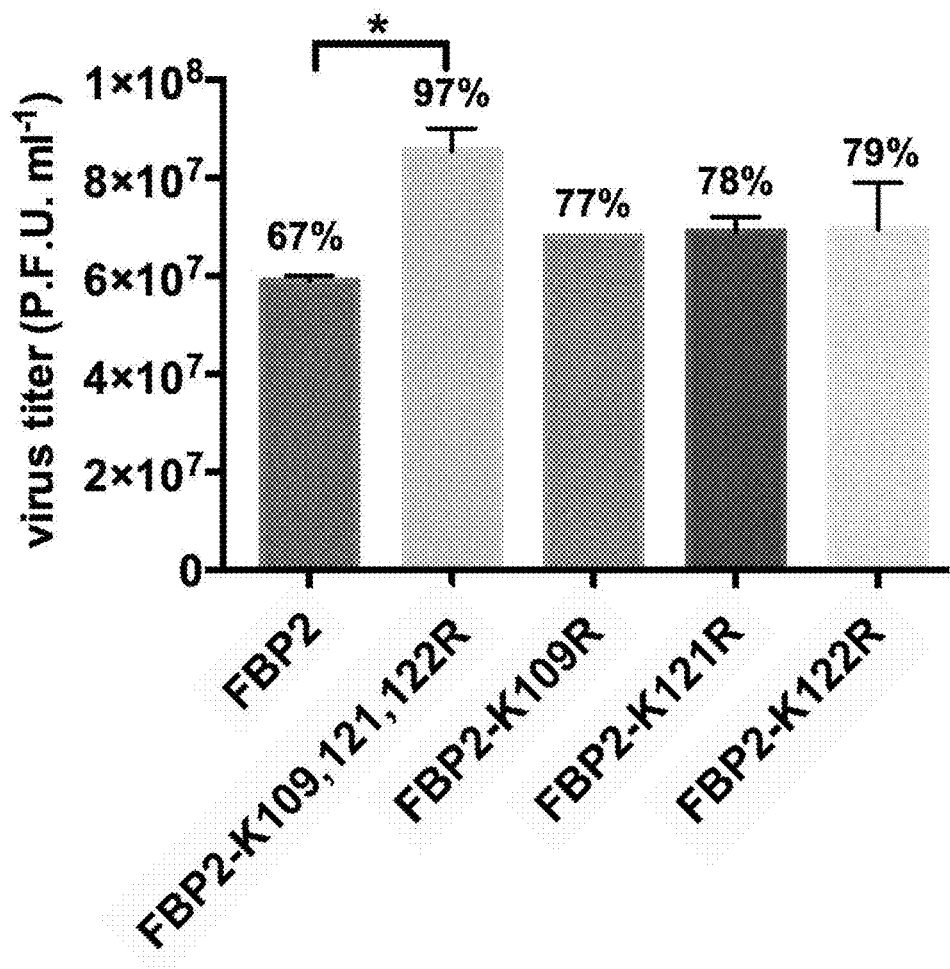
FIG. 21 shows the viral titers titrated by plaque assays in shFBP2-RD stable cells overexpressing wild-type FBP2 or each of four mutant FBP2 proteins (FBP2-K109, 121, 122R, FBP2-K109R, FBP2-K121R and FBP2-K122R) after infection with EV71 at m.o.i. of 40 for 9 hours, in which the symbol "*" represents p<0.05.
Figure 22:
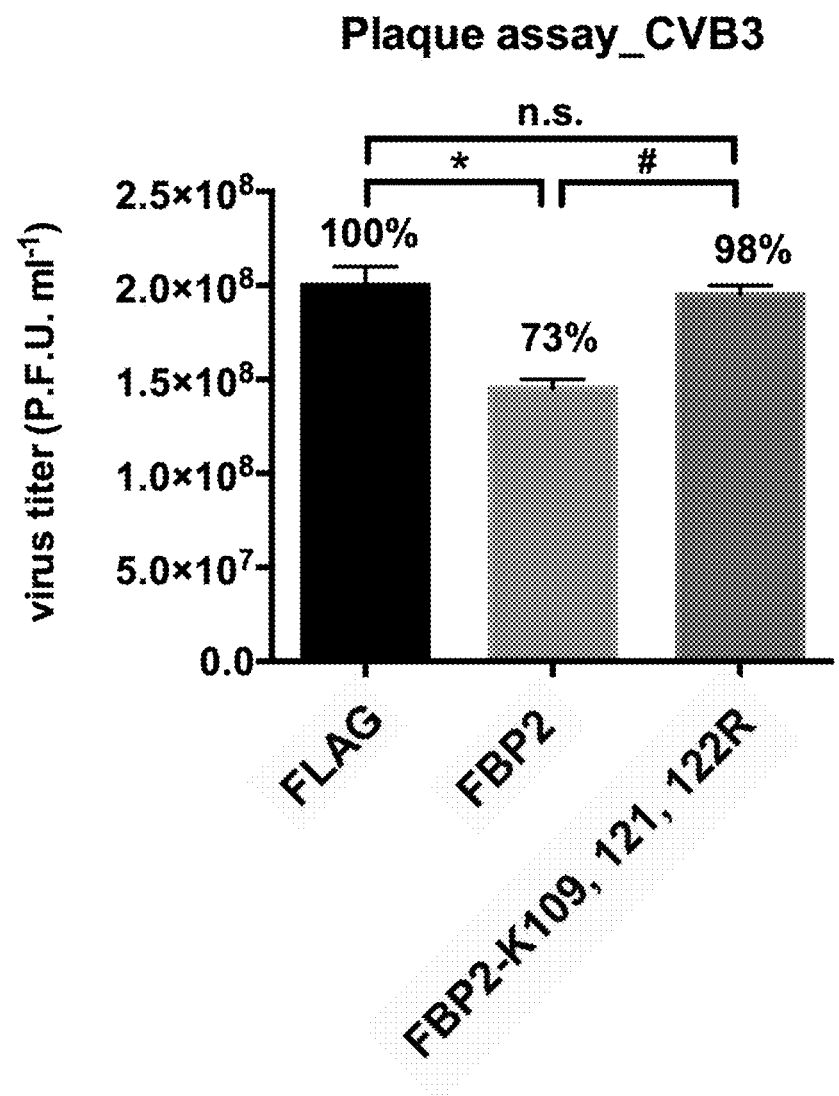
FIG. 22 shows the viral titers titrated by plaque assays in shFBP2-RD stable cells overexpressing FLAG, wild-type FBP2 or FBP2-K109, 121,122R after infection with CVB3 at m.o.i. of 40 for 9 hours, in which the abbreviation "n.s."

FIGS. 21 and 22 respectively illustrate the virus titers of EV71 and CBV3 in the shFBP2-RD cells overexpressing the respective one of the FLAG vector control, wild-type FBP2, and mutant FBP2 at 9 hours post-infection. As shown in FIG. 21, the FBP2 mutants with reduced ubiquitination, including FBP2-K109, 121, 122R, FBP2-K109R, FBP2-K121R and FBP2-K122R, increased the viral yield as compared to wild-type FBP2, with FBP2-K109, 121, 122R being the most potent in increasing EV71 viral yield.

Similarly, as revealed in FIG. 22, FBP2-K109, 121, 122R showed a significant increase in the CVB3 viral yield as compared to wild-type FBP2, however, no significant difference in the virus titer was observed in FBP2-K109, 121, 122R as compared to the FLAG vector control. These results thus infer that FBP2 mutants with at least one of the lysine residues K109, K121 and K122 that are mutated to arginine could be effective in enhancing viral IRES-driven translation activity and thereby increasing viral yield.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for producing a picornavirus with a type I internal ribosome entry site (IRES), the method comprising the steps of:

providing a recombinant cell including a recombinant expression vector, the recombinant expression vector containing a recombinant nucleic acid encoding a recombinant polypeptide which has an amino acid sequence corresponding to that of a truncated mutant product of a wild-type FBP1 protein having 644 amino acids in length, the truncated mutant product lacking a C-terminal domain of the wild-type FBP1 protein;

infecting the recombinant cell with the picornavirus;

incubating the infected recombinant cell; and harvesting the picornavirus produced, wherein the truncated mutant product of the wild-type FBP1 protein is at least one selected from the group consisting of a truncated mutant product which has an amino acid sequence of SEQ ID NO: 4, and a truncated mutant product which has an amino acid sequence of SEQ ID NO: 46.

2. The method of claim 1, wherein the recombinant nucleic acid has a nucleotide sequence selected from SEQ ID NO: 3, SEQ ID NO: 44 and SEQ ID NO: 45.

3. The method of claim 1, wherein the picornavirus with the type I IRES is an enterovirus selected from the group consisting of enterovirus A, enterovirus B, enterovirus C, enterovirus D, rhinovirus A, rhinovirus B, rhinovirus C, and combinations thereof.

4. The method of claim 3, wherein the enterovirus is selected from the group consisting of enterovirus A71, coxsackievirus B3, human rhinovirus type 2, and combinations thereof.

5. A method for preparing a viral vaccine comprising formulating a harvested picornavirus as obtained by the method of claim 1 into the viral vaccine.

6. A method for producing a picornavirus with a type I internal ribosome entry site (IRES), the method comprising the steps of:

providing a recombinant cell including a recombinant expression vector, the recombinant expression vector containing a recombinant nucleic acid encoding a recombinant polypeptide which has an amino acid sequence corresponding to that of a mutant product of a wild-type FBP2 protein having 711 amino acids in length, each of amino acid residues at positions 109, 121 and 122 of the wild-type FBP2 protein being lysine, at least one of amino acid residues at positions 109, 121 and 122 of the mutant product being arginine instead of lysine;
infecting the recombinant cell with the picornavirus;
incubating the infected recombinant cell; and
harvesting the picornavirus produced.

7. The method of claim 6, wherein the amino acid sequence of the recombinant polypeptide is selected from the group consisting of SEQ ID NO: 8, SEQ ID NO: 10, SEQ ID NO: 12, SEQ ID NO: 14 and SEQ ID NO: 16.

8. The method of claim 6, wherein the recombinant nucleic acid has a nucleotide sequence selected from the group consisting of SEQ ID NO: 7, SEQ ID NO: 9, SEQ ID NO: 11, SEQ ID NO: 13 and SEQ ID NO: 15.

9. The method of claim 6, wherein the picornavirus with the type I IRES is an enterovirus selected from the group consisting of enterovirus A, enterovirus B, enterovirus C, enterovirus D, rhinovirus A, rhinovirus B, rhinovirus C, and combinations thereof.

10. The method of claim 9, wherein the enterovirus is selected from the group consisting of enterovirus A71, coxsackievirus B3, human rhinovirus type 2, and combinations thereof.

11. The method of claim 6, wherein the recombinant cell further includes a recombinant expression vector that contains a recombinant nucleic acid encoding a recombinant polypeptide which has an amino acid sequence corresponding to that of a truncated mutant product of a wild-type FBP1 protein having 644 amino acids in length, the truncated mutant product lacking a C-terminal domain of the wild-type FBP1 protein.

12. The method of claim 11, wherein the truncated mutant product of the wild-type FBP1 protein has an amino acid sequence selected from SEQ ID NO: 4 and SEQ ID NO: 46.

13. The method of claim 11, wherein the picornavirus with the type I IRES is an enterovirus selected from the group consisting of enterovirus A, enterovirus B, enterovirus C, enterovirus D, rhinovirus A, rhinovirus B, rhinovirus C, and combinations thereof.

14. The method of claim 12, wherein the enterovirus is selected from the group consisting of enterovirus A71, coxsackievirus B3, human rhinovirus type 2, and combinations thereof.

15. A method for preparing a viral vaccine comprising formulating a harvested picornavirus as obtained by the method of claim 6 into the viral vaccine.

16. A method for preparing a viral vaccine comprising formulating a harvested picornavirus as obtained by the method of claim 11 into the viral vaccine.

* * * * *

SEQUENCE LISTING

```
<160> NUMBER OF SEQ ID NOS: 83

<210> SEQ ID NO 1
<211> LENGTH: 1935
<212> TYPE: DNA
<213> ORGANISM: Homo sapiens

<400> SEQUENCE: 1
atggcagact attcaacagt gcctcccccc tcttctggct cagctggtgg cggtggtggc      60
ggcggtggtg gtggaggagt taacgacgct ttcaaagatg cactgcagag agcccggcag     120
attgcagcaa aaattggagg tgatgcaggg acatcactga attcaaatga ctatggttat     180
gggggacaaa aaagaccttt agaagatgga gatcaaccag atgctaagaa agttgctcct     240
caaaatgact cttttggaac acagttacca ccgatgcatc agcagcaaag cagatctgta     300
aggacagaag aatacaaagt tccagatgga atggttggat tcataattgg cagaggaggt     360
gaacagatct cacgcataca acaggaatct ggatgcagaa tacagatagc tcctgacagt     420
ggtggccttc cagaaaggtc ctgtatgtta actggaacac ctgaatctgt ccagtcagca     480
aaacggttac tggaccagat tgttgaaaaa ggaagaccag ctcctggctt ccatcatggc     540
gatggaccgg gaaatgcagt tcaagaaatc atgattccag ctagcaaggc aggattagtc     600
attggaaaag gggagaaac tattaaacag cttcaggaac gggctggagt taaaatggtt     660
atgattcaag acgggccgca gaacactggt gctgacaaac ctcttaggat tacaggagac     720
ccatataaag ttcaacaagc caaggaaatg gtgttagagt taattcgtga tcaaggcggt     780
ttcagagaag ttcggaatga gtatgggtca agaataggag gaaatgaagg gatagatgtc     840
cccattccaa gatttgctgt tggcattgta ataggaagaa atggagagat gatcaaaaaa     900 atacaaatg atgctggtgt tcgcattcag tttaagccag atgatgggac aacacccgaa     960
aggatagcac aaataacagg acctccagac cgatgtcaac atgctgcaga aattattaca    1020
gaccttcttc gaagtgttca ggctggtaat cctggtggac ctggacctgg tggtcgagga    1080
agaggtagag gtcaaggcaa ctggaacatg ggaccacctg gtggactaca ggaatttaat    1140
tttattgtgc caactgggaa aactggatta ataataggaa aaggaggtga aaccataaaa    1200
agcataagcc agcagtctgg tgcaagaata gaacttcaga gaaatcctcc accaaatgca    1260
gatcctaata tgaagttatt acaattcgt ggcactccac aacagataga ctatgctcgg    1320
caactcatag aagaaagat tggtggccca gtaaatcctt tagggccacc tgtaccccat    1380 gggcccatg gtgtcccagg ccccatgga cctcctgggc ctccagggcc tggaactcca    1440
atgggaccat caaccctgc accttataat cctggaccac caggcccggc tcctcatggt    1500
cctccagccc catatgctcc ccagggatgg ggaaatgcat atccacactg gcagcagcag    1560
gctcctccgt atccagctaa ggcaggaacg gatccaaatt cagcagcttg ggctgcttat    1620
tacgctcact attatcaaca gcaagcacag ccaccaccag cagcccctgc aggtgcatca    1680
actacaactc aaactaatgg acaaggagat cagcagaatc cagcccagc tggacaggtt    1740 gattatacca aggcttggga agagtactac aagaaaatgg gtcaggcagt tcctgctccg    1800
actggggctc ctccaggtgg tcagccagat tatagtgcag cctgggctga gtattataga    1860
```

-continued

```
caacaagcag cctattatgc ccagacaagt ccccagggaa tgccacagca tcctccagca      1920
cctcagggcc aataa                                                       1935
```

<210> SEQ ID NO 2
<211> LENGTH: 644
<212> TYPE: PRT
<213> ORGANISM: Homo sapiens

<400> SEQUENCE: 2

```
Met Ala Asp Tyr Ser Thr Val Pro Pro Ser Ser Gly Ser Ala Gly
1               5                   10                  15

Gly Gly Gly Gly Gly Gly Gly Gly Gly Val Asn Asp Ala Phe Lys
            20                  25                  30

Asp Ala Leu Gln Arg Ala Arg Gln Ile Ala Ala Lys Ile Gly Gly Asp
            35                  40                      45

Ala Gly Thr Ser Leu Asn Ser Asn Asp Tyr Gly Tyr Gly Gly Gln Lys
    50                  55                      60

Arg Pro Leu Glu Asp Gly Asp Gln Pro Asp Ala Lys Lys Val Ala Pro
65                  70                  75                      80

Gln Asn Asp Ser Phe Gly Thr Gln Leu Pro Pro Met His Gln Gln Gln
                85                  90                      95

Ser Arg Ser Val Arg Thr Glu Glu Tyr Lys Val Pro Asp Gly Met Val
                100                 105                     110

Gly Phe Ile Ile Gly Arg Gly Gly Glu Gln Ile Ser Arg Ile Gln Gln
            115                 120                     125

Glu Ser Gly Cys Arg Ile Gln Ile Ala Pro Asp Ser Gly Gly Leu Pro
130                 135                     140

Glu Arg Ser Cys Met Leu Thr Gly Thr Pro Glu Ser Val Gln Ser Ala
145                 150                     155                     160

Lys Arg Leu Leu Asp Gln Ile Val Glu Lys Gly Arg Pro Ala Pro Gly
                165                 170                     175

Phe His His Gly Asp Gly Pro Gly Asn Ala Val Gln Glu Ile Met Ile
            180                 185                     190

Pro Ala Ser Lys Ala Gly Leu Val Ile Gly Lys Gly Gly Glu Thr Ile
            195                 200                     205

Lys Gln Leu Gln Glu Arg Ala Gly Val Lys Met Val Met Ile Gln Asp
            210                 215                     220

Gly Pro Gln Asn Thr Gly Ala Asp Lys Pro Leu Arg Ile Thr Gly Asp
225                 230                     235                     240

Pro Tyr Lys Val Gln Gln Ala Lys Glu Met Val Leu Glu Leu Ile Arg
                245                 250                     255

Asp Gln Gly Gly Phe Arg Glu Val Arg Asn Glu Tyr Gly Ser Arg Ile
            260                 265                     270

Gly Gly Asn Glu Gly Ile Asp Val Pro Ile Pro Arg Phe Ala Val Gly
            275                 280                     285

Ile Val Ile Gly Arg Asn Gly Glu Met Ile Lys Lys Ile Gln Asn Asp
            290                 295                     300

Ala Gly Val Arg Ile Gln Phe Lys Pro Asp Asp Gly Thr Thr Pro Glu
305                 310                     315                     320

Arg Ile Ala Gln Ile Thr Gly Pro Pro Asp Arg Cys Gln His Ala Ala
                325                 330                     335

Glu Ile Ile Thr Asp Leu Leu Arg Ser Val Gln Ala Gly Asn Pro Gly
            340                 345                     350
```

```
Gly Pro Gly Pro Gly Gly Arg Gly Arg Gly Arg Gly Gln Gly Asn Trp
            355                 360                 365

Asn Met Gly Pro Pro Gly Gly Leu Gln Glu Phe Asn Phe Ile Val Pro
370                 375                 380

Thr Gly Lys Thr Gly Leu Ile Ile Gly Lys Gly Gly Glu Thr Ile Lys
385                 390                 395                 400

Ser Ile Ser Gln Gln Ser Gly Ala Arg Ile Glu Leu Gln Arg Asn Pro
                405                 410                 415

Pro Pro Asn Ala Asp Pro Asn Met Lys Leu Phe Thr Ile Arg Gly Thr
            420                 425                 430

Pro Gln Gln Ile Asp Tyr Ala Arg Gln Leu Ile Glu Glu Lys Ile Gly
        435                 440                 445

Gly Pro Val Asn Pro Leu Gly Pro Pro Val Pro His Gly Pro His Gly
    450                 455                 460

Val Pro Gly Pro His Gly Pro Pro Gly Pro Pro Gly Pro Gly Thr Pro
465                 470                 475                 480

Met Gly Pro Tyr Asn Pro Ala Pro Tyr Asn Pro Gly Pro Pro Gly Pro
                485                 490                 495

Ala Pro His Gly Pro Ala Pro Tyr Ala Pro Gln Gly Trp Gly Asn
            500                 505                 510

Ala Tyr Pro His Trp Gln Gln Ala Pro Pro Asp Pro Ala Lys Ala
        515                 520                 525

Gly Thr Asp Pro Asn Ser Ala Ala Trp Ala Ala Tyr Ala His Tyr
    530                 535                 540

Tyr Gln Gln Gln Ala Gln Pro Pro Ala Ala Pro Ala Gly Ala Ser
545                 550                 555                 560

Thr Thr Thr Gln Thr Asn Gly Gln Gly Asp Gln Gln Asn Pro Ala Pro
                565                 570                 575

Ala Gly Gln Val Asp Tyr Thr Lys Ala Trp Glu Glu Tyr Tyr Lys Lys
            580                 585                 590

Met Gly Gln Ala Val Pro Ala Pro Thr Gly Ala Pro Pro Gly Gly Gln
        595                 600                 605

Pro Asp Tyr Ser Ala Ala Trp Ala Glu Tyr Tyr Arg Gln Gln Ala Ala
    610                 615                 620

Tyr Tyr Ala Gln Thr Ser Pro Gln Gly Met Pro Gln His Pro Pro Ala
625                 630                 635                 640

Pro Gln Gly Gln

<210> SEQ ID NO 3
<211> LENGTH: 1116
<212> TYPE: DNA
<213> ORGANISM: Artificial Sequence
<220> FEATURE:
<223> OTHER INFORMATION: FBP11-371 coding sequence

<400> SEQUENCE: 3
atggcagact attcaacagt gcctccccc tcttctggct cagctggtgg cggtggtggc     60
ggcggtggtg gtggaggagt taacgacgct ttcaagatg cactgcagag agcccggcag    120
attgcagcaa aaattggagg tgatgcaggg acatcactga attcaaatga ctatggttat    180
gggggacaaa aaagaccttt agaagatgga gatcaaccag atgctaagaa agttgctcct    240
caaaatgact cttttggaac acagttacca ccgatgcatc agcagcaaag cagatctgta    300
aggacagaag aatacaaagt tccagatgga atggttggat tcataattgg cagaggaggt    360
gaacagatct cacgcataca acaggaatct ggatgcagaa tacagatagc tcctgacagt    420
```

-continued

```
ggtggccttc agaaaggtc ctgtatgtta actggaacac ctgaatctgt ccagtcagca    480
aaacggttac tggaccagat tgttgaaaaa ggaagaccac ctcctggctt ccatcatggc    540
gatggaccgg gaaatgcagt tcaagaaatc atgattccag ctagcaaggc aggattagtc    600
attggaaaag ggggagaaac tattaaacag cttcaggaac gggctggagt taaaatggtt    660
atgattcaag acgggccgca gaacactggt gctgacaaac ctcttaggat tacaggagac    720
ccatataaag ttcaacaagc caaggaaatg gtgttagagt taattcgtga tcaaggcggt    780
ttcagagaag ttcggaatga gtatgggtca agaataggag gaaatgaagg atagatgtc    840
cccattccaa gatttgctgt tggcattgta ataggaagaa atggagagat gatcaaaaaa    900
atacaaaatg atgctggtgt tcgcattcag tttaagccag atgatgggac aacacccgaa    960
aggatagcac aaataacagg acctccagac cgatgtcaac atgctgcaga aattattaca    1020
gaccttcttc gaagtgttca ggctggtaat cctggtggac ctggacctgg tggtcgagga    1080
agaggtagag gtcaaggcaa ctggaacatg ggataa                              1116
```

```
<210> SEQ ID NO 4
<211> LENGTH: 371
<212> TYPE: PRT
<213> ORGANISM: Artificial Sequence
<220> FEATURE:
<223> OTHER INFORMATION: FBP11-371 amino acid sequence

<400> SEQUENCE: 4

Met Ala Asp Tyr Ser Thr Val Pro Pro Ser Ser Gly Ser Ala Gly
1               5                   10                  15

Gly Gly Gly Gly Gly Gly Gly Gly Gly Val Asn Asp Ala Phe Lys
                20                  25                  30

Asp Ala Leu Gln Arg Ala Arg Gln Ile Ala Ala Lys Ile Gly Gly Asp
                35                  40                  45

Ala Gly Thr Ser Leu Asn Ser Asn Asp Tyr Gly Tyr Gly Gly Gln Lys
50                  55                  60

Arg Pro Leu Glu Asp Gly Asp Gln Pro Asp Ala Lys Lys Val Ala Pro
65                  70                  75                  80

Gln Asn Asp Ser Phe Gly Thr Gln Leu Pro Pro Met His Gln Gln Gln
                85                  90                  95

Ser Arg Ser Val Arg Thr Glu Glu Tyr Lys Val Pro Asp Gly Met Val
                100                 105                 110

Gly Phe Ile Ile Gly Arg Gly Gly Glu Gln Ile Ser Arg Ile Gln Gln
                115                 120                 125

Glu Ser Gly Cys Arg Ile Gln Ile Ala Pro Asp Ser Gly Gly Leu Pro
130                 135                 140

Glu Arg Ser Cys Met Leu Thr Gly Thr Pro Glu Ser Val Gln Ser Ala
145                 150                 155                 160

Lys Arg Leu Leu Asp Gln Ile Val Glu Lys Gly Arg Ala Pro Gly
                165                 170                 175

Phe His His Gly Asp Gly Pro Gly Asn Ala Val Gln Glu Ile Met Ile
                180                 185                 190

Pro Ala Ser Lys Ala Gly Leu Val Ile Gly Lys Gly Gly Glu Thr Ile
                195                 200                 205

Lys Gln Leu Gln Glu Arg Ala Gly Val Lys Met Val Met Ile Gln Asp
                210                 215                 220

Gly Pro Gln Asn Thr Gly Ala Asp Lys Pro Leu Arg Ile Thr Gly Asp
225                 230                 235                 240
```

Pro Tyr Lys Val Gln Gln Ala Lys Glu Met Val Leu Glu Leu Ile Arg
              245                 250                 255

Asp Gln Gly Gly Phe Arg Glu Val Arg Asn Glu Tyr Gly Ser Arg Ile
          260                 265                 270

Gly Gly Asn Glu Gly Ile Asp Val Pro Ile Pro Arg Phe Ala Val Gly
      275                 280                 285

Ile Val Ile Gly Arg Asn Gly Glu Met Ile Lys Lys Ile Gln Asn Asp
  290                 295                 300

Ala Gly Val Arg Ile Gln Phe Lys Pro Asp Asp Gly Thr Thr Pro Glu
305                 310                 315                 320

Arg Ile Ala Gln Ile Thr Gly Pro Pro Asp Arg Cys Gln His Ala Ala
              325                 330                 335

Glu Ile Ile Thr Asp Leu Leu Arg Ser Val Gln Ala Gly Asn Pro Gly
          340                 345                 350

Gly Pro Gly Pro Gly Gly Arg Gly Arg Gly Arg Gly Gln Gly Asn Trp
      355                 360                 365

Asn Met Gly
    370

<210> SEQ ID NO 5
<211> LENGTH: 2136
<212> TYPE: DNA
<213> ORGANISM: Artificial Sequence
<220> FEATURE:
<223> OTHER INFORMATION: optimized FBP2 coding sequence

<400> SEQUENCE: 5
atgagcgact acagcacagg cggaccacct ccaggaccac ctcctccagc tggcggtggc      60
ggaggtgctg gcggagctgg aggtggacct ccacctggac tcccggcgc tggcgataga     120
ggtggcggag gaccttgtgg gggcggacca ggtggtggat ctgccggtgg cccttctcag     180
cctcctggcg gagggggccc tggcatcaga aggatgcct cgccgacgc cgtgcagcgg      240
gccagacaga tcgctgctaa gattggcggc gatgctgcca ccaccgtgaa caacagcacc     300
cccgacttcg gcttcggcgg ccagaaacgg cagctggaag atggcgacca gcccgagagc     360
aagaagctgg cctcccaggg cgacagcatc agcagccagc tgggccccat ccaccccca      420
cccagaacca gcatgaccga ggaataccgg gtgcccgacg catggtcgg actgatcatc      480
ggcagaggcg gcgagcagat caacaagatc agcaggaca gcggctgcaa ggtgcagatc      540
agcccccgact ctggcggcct gcccgagaga tccgtgtctc tgactggcgc ccctgagagc     600
gtgcagaaag ccaagatgat gctggacgac atcgtgtccc ggggcagagg gggtcctcca     660
ggccagttcc acgacaatgc caacggcgga cagaacggca ccgtgcagga aatcatgatt     720
ccagccggca aggccggcct ggtcatcgga aagggcggcg agacaatcaa gcagctgcag     780
gaacgggctg cgtcaagat gatcctgatc caggacggca gccagaacac caacgtggac     840
aagcccctgc ggatcatcgg ggatccttac aaagtgcagc aagcctgtga gatggtgatg     900
gacatcctcc gggaacgtga ccaaggcggc tttggggacc ggaatgagta cggatctcgg     960
attggcggag catcgatgt gccagtgccc aggcattctg ttggcgtggt cattggccgg    1020
agtggagaga tgatcaagaa gatccagaat gatgctggcg tgcggataca gttcaagcaa   1080
gatgacggga cagggcccga gaagattgct catataatgg gcccccagca ggtgcgagag   1140
cacgcagccc ggatcatcaa cgacctcctc agagcctca ggagtggtcc cccaggtcct   1200
ccaggggggtc aggcatgcc cccgggggggc cgaggccgag aagaggcca aggcaattgg   1260

```
ggtcccctg gcggggagat gaccttctcc atccccactc acaagtgtgg gctggtcatc    1320
ggccgaggtg gcgagaatgt gaaagccata aaccagcaga cgggagcctt cgtagagatc    1380
tcccggcagc tgccacccaa cggggacccc aacttcaagt tgttcatcat ccggggttca    1440
ccccagcaga ttgaccacgc caagcagctt atcgaggaaa agatcgaggg tcctctctgc    1500
ccagttggac caggcccagg tggcccaggc cctgctggcc caatggggcc cttcaatcct    1560
gggcccttca accaggggcc acccggggct ccccacatg ccggggggcc ccctcctcac    1620
cagtacccac cccagggctg gggcaatacc taccccagt ggcagccgcc tgctcctcat    1680
gacccaagca aagcagctgc agcggccgcg accccaacg ccgcgtgggc cgcctactac    1740
tcacactact accagcagcc cccgggcccc gtcccggcc ccgcaccggc ccctgcggcc    1800
ccaccggctc agggtgagcc ccctcagccc cacccaccg gccagtcgga ctacactaag    1860
gcctgggaag agtattacaa aaagatcggc cagcagcccc agcagccgg agcgccccca    1920 cagcaggact acacgaaggc ttgggaggag tactacaaga agcaagcgca agtggccacc    1980
ggagggggtc caggagctcc cccaggctcc cagccagact acagtgccgc ctgggcggaa    2040
tattacagac agcaggccgc ttactacgga cagaccccag gtcctggcgg ccccagccg    2100 ccgcccacgc agcagggaca gcagcaggct caatga                              2136

<210> SEQ ID NO 6
<211> LENGTH: 711
<212> TYPE: PRT
<213> ORGANISM: Homo sapiens

<400> SEQUENCE: 6

Met Ser Asp Tyr Ser Thr Gly Gly Pro Pro Pro Gly Pro Pro Pro Pro
1               5                   10                  15

Ala Gly Gly Gly Gly Ala Gly Gly Ala Gly Gly Pro Pro Pro
            20                  25                  30

Gly Pro Pro Gly Ala Gly Asp Arg Gly Gly Gly Pro Cys Gly Gly
        35                  40                  45

Gly Pro Gly Gly Gly Ser Ala Gly Gly Pro Ser Gln Pro Pro Gly Gly
    50                  55                  60

Gly Gly Pro Gly Ile Arg Lys Asp Ala Phe Ala Asp Ala Val Gln Arg
65                  70                  75                  80

Ala Arg Gln Ile Ala Ala Lys Ile Gly Gly Asp Ala Ala Thr Thr Val
                85                  90                  95

Asn Asn Ser Thr Pro Asp Phe Gly Phe Gly Gly Gln Lys Arg Gln Leu
            100                 105                 110

Glu Asp Gly Asp Gln Pro Glu Ser Lys Lys Leu Ala Ser Gln Gly Asp
        115                 120                 125

Ser Ile Ser Ser Gln Leu Gly Pro Ile His Pro Pro Arg Thr Ser
    130                 135                 140

Met Thr Glu Glu Tyr Arg Val Pro Asp Gly Met Val Gly Leu Ile Ile
145                 150                 155                 160

Gly Arg Gly Gly Glu Gln Ile Asn Lys Ile Gln Gln Asp Ser Gly Cys
                165                 170                 175

Lys Val Gln Ile Ser Pro Asp Ser Gly Gly Leu Pro Glu Arg Ser Val
            180                 185                 190

Ser Leu Thr Gly Ala Pro Glu Ser Val Gln Lys Ala Lys Met Met Leu
        195                 200                 205

Asp Asp Ile Val Ser Arg Gly Arg Gly Gly Pro Pro Gly Gln Phe His
```

```
                210                 215                 220

Asp Asn Ala Asn Gly Gly Gln Asn Gly Thr Val Gln Glu Ile Met Ile
225                 230                 235                 240

Pro Ala Gly Lys Ala Gly Leu Val Ile Gly Lys Gly Gly Glu Thr Ile
                245                 250                 255

Lys Gln Leu Gln Glu Arg Ala Gly Val Lys Met Ile Leu Ile Gln Asp
                260                 265                 270

Gly Ser Gln Asn Thr Asn Val Asp Lys Pro Leu Arg Ile Ile Gly Asp
            275                 280                 285

Pro Tyr Lys Val Gln Gln Ala Cys Glu Met Val Met Asp Ile Leu Arg
            290                 295                 300

Glu Arg Asp Gln Gly Gly Phe Gly Asp Arg Asn Glu Tyr Gly Ser Arg
305                 310                 315                 320

Ile Gly Gly Gly Ile Asp Val Pro Val Pro Arg His Ser Val Gly Val
                325                 330                 335

Val Ile Gly Arg Ser Gly Glu Met Ile Lys Lys Ile Gln Asn Asp Ala
                340                 345                 350

Gly Val Arg Ile Gln Phe Lys Gln Asp Asp Gly Thr Gly Pro Glu Lys
            355                 360                 365

Ile Ala His Ile Met Gly Pro Pro Asp Arg Cys Glu His Ala Ala Arg
            370                 375                 380

Ile Ile Asn Asp Leu Leu Gln Ser Leu Arg Ser Gly Pro Pro Gly Pro
385                 390                 395                 400

Pro Gly Gly Pro Gly Met Pro Gly Gly Arg Gly Arg Gly Arg Gly
                405                 410                 415

Gln Gly Asn Trp Gly Pro Pro Gly Glu Met Thr Phe Ser Ile Pro
            420                 425                 430

Thr His Lys Cys Gly Leu Val Ile Gly Arg Gly Gly Glu Asn Val Lys
            435                 440                 445

Ala Ile Asn Gln Gln Thr Gly Ala Phe Val Glu Ile Ser Arg Gln Leu
450                 455                 460

Pro Pro Asn Gly Asp Pro Asn Phe Lys Leu Phe Ile Ile Arg Gly Ser
465                 470                 475                 480

Pro Gln Gln Ile Asp His Ala Lys Gln Leu Ile Glu Glu Lys Ile Glu
                485                 490                 495

Gly Pro Leu Cys Pro Val Gly Pro Gly Pro Gly Pro Gly Pro Ala
            500                 505                 510

Gly Pro Met Gly Pro Phe Asn Pro Gly Pro Phe Asn Gln Gly Pro Pro
            515                 520                 525

Gly Ala Pro Pro His Ala Gly Gly Pro Pro His Gln Tyr Pro Pro
530                 535                 540

Gln Gly Trp Gly Asn Thr Tyr Pro Gln Trp Gln Pro Ala Pro His
545                 550                 555                 560

Asp Pro Ser Lys Ala Ala Ala Ala Ala Asp Pro Asn Ala Ala Trp
                565                 570                 575

Ala Ala Tyr Tyr Ser His Tyr Tyr Gln Gln Pro Pro Gly Pro Val Pro
            580                 585                 590

Gly Pro Ala Pro Ala Pro Ala Ala Pro Ala Gln Gly Glu Pro Pro
            595                 600                 605

Gln Pro Pro Pro Thr Gly Gln Ser Asp Tyr Thr Lys Ala Trp Glu Glu
            610                 615                 620

Tyr Tyr Lys Lys Ile Gly Gln Gln Pro Gln Gln Pro Gly Ala Pro Pro
625                 630                 635                 640
```

Gln Gln Asp Tyr Thr Lys Ala Trp Glu Glu Tyr Tyr Lys Lys Gln Ala
                645                 650                 655

Gln Val Ala Thr Gly Gly Pro Gly Ala Pro Pro Gly Ser Gln Pro
            660                 665                 670

Asp Tyr Ser Ala Ala Trp Ala Glu Tyr Arg Gln Gln Ala Ala Tyr
        675                 680                 685

Tyr Gly Gln Thr Pro Gly Pro Gly Gly Pro Gln Pro Pro Thr Gln
    690                 695                 700

Gln Gly Gln Gln Gln Ala Gln
705                 710

<210> SEQ ID NO 7
<211> LENGTH: 2136
<212> TYPE: DNA
<213> ORGANISM: Artificial Sequence
<220> FEATURE:
<223> OTHER INFORMATION: FBP2-K109,121,122R coding sequence

<400> SEQUENCE: 7

```
atgagcgact acagcacagg cggaccacct ccaggaccac ctcctccagc tggcggtggc      60
ggaggtgctg gcggagctgg aggtggacct ccacctggac ctcccggcgc tggcgataga     120
ggtggcggag gaccttgtgg gggcggacca ggtggtggat ctgccggtgg cccttctcag     180
cctcctggcg aggggggccc tggcatcaga aggatgcct cgccgacgc cgtgcagcgg       240
gccagacaga tcgctgctaa gattggcggc gatgctgcca ccaccgtgaa caacagcacc     300
cccgacttcg gcttcggcgg ccagagacga cagctggaag atggcgacca gcccgagagc     360
aggaggctgg cctcccaggg cgacagcatc agcagccagc tgggccccat ccacccccca     420
cccagaacca gcatgaccga ggaataccgg gtgcccgacg gcatggtcgg actgatcatc     480
ggcagaggcg gcgagcagat caacaagatc agcaggaca cggctgcaa ggtgcagatc       540
agccccgact ctggcggcct gcccgagaga tccgtgtctc tgactggcgc ccctgagagc     600
gtgcagaaag ccaagatgat gctggacgac atcgtgtccc ggggcagagg gggtcctcca     660
ggccagttcc acgacaatgc caacggcgga cagaacggca ccgtgcagga aatcatgatt     720
ccagccggca aggccggcct ggtcatcgga aagggcggcg agacaatcaa gcagctgcag     780
gaacgggctg gcgtcaagat gatcctgatc caggacggca ccagaacac caacgtggac     840
aagcccctgc ggatcatcgg ggatccttac aaagtgcagc aagcctgtga gatggtgatg     900
gacatcctcc gggaacgtga ccaaggcggc tttgggacc ggaatgagta cggatctcgg     960
attggcggag gcatcgatgt gccagtgccc aggcattctg ttggcgtggt cattggccgg    1020
agtggagaga tgatcaagaa gatccagaat gatgctggcg tgcggataca gttcaagcaa    1080
gatgacggga cagggcccga aagattgct catataatgg ggccccaga caggtgcgag      1140
cacgcagccc ggatcatcaa cgacctcctc cagagcctca ggagtggtcc cccaggtcct    1200
ccaggggggtc caggcatgcc cccgggggcc cgaggccgag gaagaggcca aggcaattgg    1260
ggtccccctg gcggggagat gaccttctcc atccccactc acaagtgtgg gctggtcatc    1320
ggccgaggtg gcgagaatgt gaaagccata aaccagcaga cgggagcctt cgtagagatc    1380
tccccggcagc tgccacccaa cggggacccc aacttcaagt tgttcatcat ccggggttca    1440
ccccagcaga ttgaccacgc caagcagctt atcgaggaaa agatcgaggg tcctctctgc    1500
ccagttggac caggcccagg tggcccaggc ctgctggcc caatgggccc cttcaatcct    1560
gggcccttca accaggggcc accccgggggct ccccccacatg ccgggggggcc ccctcctcac    1620
```

-continued

```
cagtacccac cccagggctg gggcaatacc taccccagt ggcagccgcc tgctcctcat   1680
gacccaagca aagcagctgc agcggccgcg gaccccaacg ccgcgtgggc cgcctactac   1740
tcacactact accagcagcc cccgggcccc gtccccggcc ccgcaccggc ccctgcggcc   1800
ccaccggctc agggtgagcc ccctcagccc cacccaccg gccagtcgga ctacactaag    1860
gcctgggaag agtattacaa aaagatcggc cagcagcccc agcagccggg agcgccccca   1920
cagcaggact acacgaaggc ttgggaggag tactacaaga agcaagcgca agtgccaccc   1980 ggaggggtc caggagctcc cccaggctcc cagccagact acagtgccgc ctgggcggaa   2040
tattacagac agcaggccgc ttactacgga cagaccccag gtcctggcgg ccccagccg    2100 ccgcccacgc agcagggaca gcagcaggct caatga                             2136
```

<210> SEQ ID NO 8
<211> LENGTH: 711
<212> TYPE: PRT
<213> ORGANISM: Artificial Sequence
<220> FEATURE:
<223> OTHER INFORMATION: FBP2-K109,121,122R amino acid sequence
<400> SEQUENCE: 8

```
Met Ser Asp Tyr Ser Thr Gly Gly Pro Pro Gly Pro Pro Pro Pro
1               5                   10                  15

Ala Gly Gly Gly Gly Ala Gly Gly Ala Gly Gly Pro Pro Pro
            20                  25                  30

Gly Pro Pro Gly Ala Gly Asp Arg Gly Gly Gly Gly Pro Cys Gly Gly
        35                  40                  45

Gly Pro Gly Gly Gly Ser Ala Gly Pro Ser Gln Pro Pro Gly Gly
    50                  55                  60

Gly Gly Pro Gly Ile Arg Lys Asp Ala Phe Ala Asp Ala Val Gln Arg
65                  70                  75                  80

Ala Arg Gln Ile Ala Ala Lys Ile Gly Gly Asp Ala Ala Thr Thr Val
                85                  90                  95

Asn Asn Ser Thr Pro Asp Phe Gly Phe Gly Gly Gln Arg Arg Gln Leu
            100                 105                 110

Glu Asp Gly Asp Gln Pro Glu Ser Arg Arg Leu Ala Ser Gln Gly Asp
        115                 120                 125

Ser Ile Ser Ser Gln Leu Gly Pro Ile His Pro Pro Arg Thr Ser
    130                 135                 140

Met Thr Glu Glu Tyr Arg Val Pro Asp Gly Met Val Gly Leu Ile Ile
145                 150                 155                 160

Gly Arg Gly Gly Glu Gln Ile Asn Lys Ile Gln Gln Asp Ser Gly Cys
                165                 170                 175

Lys Val Gln Ile Ser Pro Asp Ser Gly Gly Leu Pro Glu Arg Ser Val
            180                 185                 190

Ser Leu Thr Gly Ala Pro Glu Ser Val Gln Lys Ala Lys Met Met Leu
        195                 200                 205

Asp Asp Ile Val Ser Arg Gly Arg Gly Gly Pro Pro Gly Gln Phe His
    210                 215                 220

Asp Asn Ala Asn Gly Gly Gln Asn Gly Thr Val Gln Glu Ile Met Ile
225                 230                 235                 240

Pro Ala Gly Lys Ala Gly Leu Val Ile Gly Lys Gly Gly Glu Thr Ile
                245                 250                 255

Lys Gln Leu Gln Glu Arg Ala Gly Val Lys Met Ile Leu Ile Gln Asp
            260                 265                 270
```

-continued

```
Gly Ser Gln Asn Thr Asn Val Asp Lys Pro Leu Arg Ile Ile Gly Asp
            275                 280                 285

Pro Tyr Lys Val Gln Gln Ala Cys Glu Met Val Met Asp Ile Leu Arg
        290                 295                 300

Glu Arg Asp Gln Gly Gly Phe Gly Asp Arg Asn Glu Tyr Gly Ser Arg
305                 310                 315                 320

Ile Gly Gly Gly Ile Asp Val Pro Val Pro Arg His Ser Val Gly Val
                325                 330                 335

Val Ile Gly Arg Ser Gly Glu Met Ile Lys Lys Ile Gln Asn Asp Ala
            340                 345                 350

Gly Val Arg Ile Gln Phe Lys Gln Asp Gly Thr Gly Pro Glu Lys
        355                 360                 365

Ile Ala His Ile Met Gly Pro Pro Asp Arg Cys Glu His Ala Ala Arg
    370                 375                 380

Ile Ile Asn Asp Leu Leu Gln Ser Leu Arg Ser Gly Pro Pro Gly Pro
385                 390                 395                 400

Pro Gly Gly Pro Gly Met Pro Pro Gly Gly Arg Gly Arg Gly Arg Gly
                405                 410                 415

Gln Gly Asn Trp Gly Pro Pro Gly Gly Glu Met Thr Phe Ser Ile Pro
            420                 425                 430

Thr His Lys Cys Gly Leu Val Ile Gly Arg Gly Gly Glu Asn Val Lys
        435                 440                 445

Ala Ile Asn Gln Gln Thr Gly Ala Phe Val Glu Ile Ser Arg Gln Leu
    450                 455                 460

Pro Pro Asn Gly Asp Pro Asn Phe Lys Leu Phe Ile Ile Arg Gly Ser
465                 470                 475                 480

Pro Gln Gln Ile Asp His Ala Lys Gln Leu Ile Glu Glu Lys Ile Glu
                485                 490                 495

Gly Pro Leu Cys Pro Val Gly Pro Gly Pro Gly Gly Pro Gly Pro Ala
            500                 505                 510

Gly Pro Met Gly Pro Phe Asn Pro Gly Pro Phe Asn Gln Gly Pro Pro
        515                 520                 525

Gly Ala Pro Pro His Ala Gly Gly Pro Pro His Gln Tyr Pro Pro
    530                 535                 540

Gln Gly Trp Gly Asn Thr Tyr Pro Gln Trp Gln Pro Pro Ala Pro His
545                 550                 555                 560

Asp Pro Ser Lys Ala Ala Ala Ala Ala Asp Pro Asn Ala Ala Trp
                565                 570                 575

Ala Ala Tyr Tyr Ser His Tyr Tyr Gln Pro Pro Gly Pro Val Pro
            580                 585                 590

Gly Pro Ala Pro Ala Pro Ala Ala Pro Pro Ala Gln Gly Glu Pro Pro
        595                 600                 605

Gln Pro Pro Pro Thr Gly Gln Ser Asp Tyr Thr Lys Ala Trp Glu Glu
    610                 615                 620

Tyr Tyr Lys Lys Ile Gly Gln Gln Pro Gln Pro Gly Ala Pro Pro
625                 630                 635                 640

Gln Gln Asp Tyr Thr Lys Ala Trp Glu Glu Tyr Tyr Lys Lys Gln Ala
                645                 650                 655

Gln Val Ala Thr Gly Gly Pro Gly Ala Pro Pro Gly Ser Gln Pro
            660                 665                 670

Asp Tyr Ser Ala Ala Trp Ala Glu Tyr Tyr Arg Gln Gln Ala Ala Tyr
        675                 680                 685
```

```
Tyr Gly Gln Thr Pro Gly Pro Gly Gly Pro Gln Pro Pro Thr Gln
    690                 695                 700
Gln Gly Gln Gln Gln Ala Gln
705                 710
```

<210> SEQ ID NO 9
<211> LENGTH: 2136
<212> TYPE: DNA
<213> ORGANISM: Artificial Sequence
<220> FEATURE:
<223> OTHER INFORMATION: FBP2-K109 coding sequence

<400> SEQUENCE: 9

| | | |
|---|---|---|
| atgagcgact acagcacagg cggaccacct ccaggaccac ctcctccagc tggcggtggc | 60 |
| ggaggtgctg gcggagctgg aggtggacct ccacctggac ctcccggcgc tggcgataga | 120 |
| ggtggcggag gaccttgtgg gggcggacca ggtggtggat ctgccggtgg cccttctcag | 180 |
| cctcctggcg gagggggccc tggcatcaga aggatgcct cgccgacgc cgtgcagcgg | 240 |
| gccagacaga tcgctgctaa gattggcggc gatgctgcca ccaccgtgaa caacagcacc | 300 |
| cccgacttcg gcttcggcgg ccagagacgg cagctggaag atggcgacca gcccgagagc | 360 |
| aagaagctgg cctcccaggg cgacagcatc agcagccagc tgggcccccat ccaccccca | 420 |
| cccagaacca gcatgaccga ggaataccgg gtgcccgacg gcatggtcgg actgatcatc | 480 |
| ggcagaggcg cgagcagat caacaagatc agcaggaca cgggctgcaa ggtgcagatc | 540 |
| agccccgact ctggcggcct gcccgagaga tccgtgtctc tgactggcgc ccctgagagc | 600 |
| gtgcagaaag ccaagatgat gctggacgac atcgtgtccc ggggcagagg gggtcctcca | 660 |
| ggccagttcc acgacaatgc caacggcgga cagaacggca ccgtgcagga aatcatgatt | 720 |
| ccagccggca aggccggcct ggtcatcgga agggcggcg agacaatcaa gcagctgcag | 780 |
| gaacgggctg gcgtcaagat gatcctgatc caggacggca ccagaacac caacgtggac | 840 |
| aagcccctgc ggatcatcgg ggatccttac aaagtgcagc aagcctgtga gatggtgatg | 900 |
| gacatcctcc gggaacgtga ccaaggcggc tttggggacc ggaatgagta cggatctcgg | 960 |
| attggcggag catcgatgt gccagtgccc aggcattctg ttggcgtggt cattggccgg | 1020 |
| agtggagaga tgatcaagaa gatccagaat gatgctggcg tgcggataca gttcaagcaa | 1080 |
| gatgacggga cagggcccga gaagattgct catataatgg ggccccccaga caggtgcgag | 1140 |
| cacgcagccc ggatcatcaa cgacctcctc cagagcctca ggagtggtcc cccaggtcct | 1200 |
| ccaggggggtc caggcatgcc cccgggggggc cgaggccgag aagaggcca aggcaattgg | 1260 |
| ggtcccctg gcggggagat gaccttctcc atccccactc acaagtgtgg gctggtcatc | 1320 |
| ggccgaggtg gcgagaatgt gaaagccata aaccagcaga cgggagcctt cgtagagatc | 1380 |
| tcccggcagc tgccacccaa cggggacccc aacttcaagt tgttcatcat ccggggttca | 1440 |
| ccccagcaga ttgaccacgc caagcagctt atcgaggaaa agatcgaggg tcctctctgc | 1500 |
| ccagttggac caggcccagg tggcccaggc cctgctggcc caatgggcc cttcaatcct | 1560 |
| gggcccttca ccaggggccc acccggggct ccccacatg ccggggggcc ccctcctcac | 1620 |
| cagtacccac cccagggctg gggcaatacc taccccagt ggcagccgcc tgctcctcat | 1680 |
| gacccaagca aagcagctgc agcggccgcg gaccccaacg ccgcgtgggc cgcctactac | 1740 |
| tcacactact accagcagcc cccggggccc gtcccggggc ccgcaccggc cctgcggcc | 1800 |
| ccaccggctc agggtgagcc ccctcagccc cacccaccg gccagtcgga ctacactaag | 1860 |
| gcctgggaag agtattacaa aaagatcggc cagcagcccc agcagcccgg agcgccccca | 1920 |

```
cagcaggact acacgaaggc ttgggaggag tactacaaga agcaagcgca agtggccacc   1980
ggagggggtc caggagctcc cccaggctcc cagccagact acagtgccgc ctgggcggaa   2040
tattacagac agcaggccgc ttactacgga cagaccccag gtcctggcgg ccccccagccg  2100 ccgcccacgc agcagggaca gcagcaggct caatga                             2136
```

<210> SEQ ID NO 10
<211> LENGTH: 711
<212> TYPE: PRT
<213> ORGANISM: Artificial Sequence
<220> FEATURE:
<223> OTHER INFORMATION: FBP2-K109 amino acid sequence

<400> SEQUENCE: 10

```
Met Ser Asp Tyr Ser Thr Gly Gly Pro Pro Gly Pro Pro Pro
1               5                   10                  15

Ala Gly Gly Gly Gly Ala Gly Gly Ala Gly Gly Pro Pro Pro
            20                  25                  30

Gly Pro Pro Gly Ala Gly Asp Arg Gly Gly Gly Pro Cys Gly Gly
        35                  40                  45

Gly Pro Gly Gly Gly Ser Ala Gly Gly Pro Ser Gln Pro Pro Gly Gly
    50                  55                  60

Gly Gly Pro Gly Ile Arg Lys Asp Ala Phe Ala Asp Ala Val Gln Arg
65                  70                  75                  80

Ala Arg Gln Ile Ala Ala Lys Ile Gly Gly Asp Ala Ala Thr Thr Val
                85                  90                  95

Asn Asn Ser Thr Pro Asp Phe Gly Phe Gly Gly Gln Arg Arg Gln Leu
            100                 105                 110

Glu Asp Gly Asp Gln Pro Glu Ser Lys Lys Leu Ala Ser Gln Gly Asp
        115                 120                 125

Ser Ile Ser Ser Gln Leu Gly Pro Ile His Pro Pro Arg Thr Ser
    130                 135                 140

Met Thr Glu Glu Tyr Arg Val Pro Asp Gly Met Val Gly Leu Ile Ile
145                 150                 155                 160

Gly Arg Gly Gly Glu Gln Ile Asn Lys Ile Gln Gln Asp Ser Gly Cys
                165                 170                 175

Lys Val Gln Ile Ser Pro Asp Ser Gly Gly Leu Pro Glu Arg Ser Val
            180                 185                 190

Ser Leu Thr Gly Ala Pro Glu Ser Val Gln Lys Ala Lys Met Met Leu
        195                 200                 205

Asp Asp Ile Val Ser Arg Gly Arg Gly Gly Pro Pro Gly Gln Phe His
    210                 215                 220

Asp Asn Ala Asn Gly Gly Gln Asn Gly Thr Val Gln Glu Ile Met Ile
225                 230                 235                 240

Pro Ala Gly Lys Ala Gly Leu Val Ile Gly Lys Gly Gly Glu Thr Ile
                245                 250                 255

Lys Gln Leu Gln Glu Arg Ala Gly Val Lys Met Ile Leu Ile Gln Asp
            260                 265                 270

Gly Ser Gln Asn Thr Asn Val Asp Lys Pro Leu Arg Ile Ile Gly Asp
        275                 280                 285

Pro Tyr Lys Val Gln Gln Ala Cys Glu Met Val Met Asp Ile Leu Arg
    290                 295                 300

Glu Arg Asp Gln Gly Gly Phe Gly Asp Arg Asn Glu Tyr Gly Ser Arg
305                 310                 315                 320
```

```
Ile Gly Gly Gly Ile Asp Val Pro Val Pro Arg His Ser Val Gly Val
            325                 330                 335

Val Ile Gly Arg Ser Gly Glu Met Ile Lys Lys Ile Gln Asn Asp Ala
        340                 345                 350

Gly Val Arg Ile Gln Phe Lys Gln Asp Asp Gly Thr Gly Pro Glu Lys
            355                 360                 365

Ile Ala His Ile Met Gly Pro Pro Asp Arg Cys Glu His Ala Ala Arg
    370                 375                 380

Ile Ile Asn Asp Leu Leu Gln Ser Leu Arg Ser Gly Pro Pro Gly Pro
385                 390                 395                 400

Pro Gly Gly Pro Gly Met Pro Pro Gly Gly Arg Gly Arg Gly Arg Gly
                405                 410                 415

Gln Gly Asn Trp Gly Pro Pro Gly Gly Glu Met Thr Phe Ser Ile Pro
            420                 425                 430

Thr His Lys Cys Gly Leu Val Ile Gly Arg Gly Gly Glu Asn Val Lys
        435                 440                 445

Ala Ile Asn Gln Gln Thr Gly Ala Phe Val Glu Ile Ser Arg Gln Leu
    450                 455                 460

Pro Pro Asn Gly Asp Pro Asn Phe Lys Leu Phe Ile Ile Arg Gly Ser
465                 470                 475                 480

Pro Gln Gln Ile Asp His Ala Lys Gln Leu Ile Glu Glu Lys Ile Glu
                485                 490                 495

Gly Pro Leu Cys Pro Val Gly Pro Gly Pro Gly Pro Gly Pro Gly Ala
            500                 505                 510

Gly Pro Met Gly Pro Phe Asn Pro Gly Pro Phe Asn Gln Gly Pro Pro
        515                 520                 525

Gly Ala Pro Pro His Ala Gly Gly Pro Pro His Gln Tyr Pro Pro
    530                 535                 540

Gln Gly Trp Gly Asn Thr Tyr Pro Gln Trp Gln Pro Pro Ala Pro His
545                 550                 555                 560

Asp Pro Ser Lys Ala Ala Ala Ala Ala Asp Pro Asn Ala Ala Trp
                565                 570                 575

Ala Ala Tyr Tyr Ser His Tyr Tyr Gln Gln Pro Pro Gly Pro Val Pro
            580                 585                 590

Gly Pro Ala Pro Ala Pro Ala Ala Pro Pro Ala Gln Gly Glu Pro Pro
        595                 600                 605

Gln Pro Pro Pro Thr Gly Gln Ser Asp Tyr Thr Lys Ala Trp Glu Glu
    610                 615                 620

Tyr Tyr Lys Lys Ile Gly Gln Gln Pro Gln Gln Pro Gly Ala Pro Pro
625                 630                 635                 640

Gln Gln Asp Tyr Thr Lys Ala Trp Glu Glu Tyr Tyr Lys Lys Gln Ala
                645                 650                 655

Gln Val Ala Thr Gly Gly Pro Gly Ala Pro Pro Gly Ser Gln Pro
            660                 665                 670

Asp Tyr Ser Ala Ala Trp Ala Glu Tyr Tyr Arg Gln Gln Ala Ala Tyr
        675                 680                 685

Tyr Gly Gln Thr Pro Gly Pro Gly Gly Pro Gln Pro Pro Pro Thr Gln
    690                 695                 700

Gln Gly Gln Gln Gln Ala Gln
705                 710

<210> SEQ ID NO 11
<211> LENGTH: 2136
<212> TYPE: DNA
```

<213> ORGANISM: Artificial Sequence
<220> FEATURE:
<223> OTHER INFORMATION: FBP2-K121R coding sequence

<400> SEQUENCE: 11

```
atgagcgact acagcacagg cggaccacct ccaggaccac ctcctccagc tggcggtggc    60
ggaggtgctg gcggagctgg aggtggacct ccacctggac ctcccggcgc tggcgataga   120
ggtggcggag gaccttgtgg gggcggacca ggtggtggat ctgccggtgg cccttctcag   180
cctcctggcg agggggccc tggcatcaga aggatgcct tcgccgacgc cgtgcagcgg    240
gccagacaga tcgctgctaa gattggcggc gatgctgcca ccaccgtgaa caacagcacc   300
cccgacttcg gcttcggcgg ccagaaacgg cagctggaag atggcgacca gcccgagagc   360
aggaagctgg cctcccaggg cgacagcatc agcagccagc tgggcccat ccaccccca    420
cccagaacca gcatgaccga ggaataccgg gtgcccgacg gcatggtcgg actgatcatc   480
ggcagaggcg gcgagcagat caacaagatc agcaggaca gcggctgcaa ggtgcagatc   540
agccccgact ctggcggcct gcccgagaga tccgtgtctc tgactggcgc ccctgagagc   600
gtgcagaaag ccaagatgat gctggacgac atcgtgtccc ggggcagagg gggtcctcca   660
ggccagttcc acgacaatgc caacggcgga cagaacggca ccgtgcagga aatcatgatt   720
ccagccggca aggccggcct ggtcatcgga agggcggcg agacaatcaa gcagctgcag   780
gaacgggctg gcgtcaagat gatcctgatc aggacggca gcagaacac caacgtggac   840
aagcccctgc ggatcatcgg ggatccttac aaagtgcagc aagcctgtga tggtgatg    900
gacatcctcc gggaacgtga ccaaggcggc tttgggacc ggaatgagta cggatctcgg   960
attggcggag gcatcgatgt gccagtgccc aggcattctg ttggcgtggt cattggccgg   1020
agtggagaga tgatcaagaa gatccagaat gatgctggcg tgcggataca gttcaagcaa   1080
gatgacggga cagggcccga gaagattgct catataatgg gcccccaga caggtgcgag   1140
cacgcagccc ggatcatcaa cgacctcctc cagagcctca ggagtggtcc cccaggtcct   1200
ccagggggtc caggcatgcc cccgggggc cgaggccgag gaagaggcca aggcaattgg   1260
ggtcccctg gcggggagat gaccttctcc atccccactc acaagtgtgg gctggtcatc   1320
ggccgaggtg gcgagaatgt gaaagccata accagcaga cgggagcctt cgtagagatc   1380
tcccggcagc tgccacccaa cggggacccc aacttcaagt tgttcatcat ccggggttca   1440
ccccagcaga ttgaccacgc caagcagctt atcgaggaaa agatcgaggg tcctctctgc   1500
ccagttggac caggcccagg tggcccaggc cctgctggcc caatgggcc cttcaatcct   1560
gggcccttca accaggggcc acccggggct ccccacatg ccgggggggcc ccctcctcac   1620
cagtacccac cccagggctg gggcaatacc taccccagt ggcagccgcc tgctcctcat   1680
gacccaagca aagcagctgc agcggccgcg accccaacg ccgcgtgggc cgcctactac   1740
tcacactact accagcagcc cccgggcccc gtccccggcc ccgcaccggc ccctgcggcc   1800
ccaccggctc agggtgagcc ccctcagccc cacccaccg gccagtcgga ctacactaag   1860
gcctgggaag agtattacaa aaagatcggc cagcagcccc agcagcccgg agcgcccca    1920
cagcaggact acacgaaggc ttgggaggag tactacaaga gcaagcgca agtgccacc    1980
ggagggggtc caggagctcc cccaggctcc cagccagact acagtgccgc ctgggcggaa   2040
tattacagac agcaggccgc ttactacgga cagaccccag gtcctggcgg ccccagccg    2100
ccgcccacgc agcagggaca gcagcaggct caatga                            2136
```

-continued

```
<210> SEQ ID NO 12
<211> LENGTH: 711
<212> TYPE: PRT
<213> ORGANISM: Artificial Sequence
<220> FEATURE:
<223> OTHER INFORMATION: FBP2-K121R amino acid sequence

<400> SEQUENCE: 12
```

| Met | Ser | Asp | Tyr | Ser | Thr | Gly | Gly | Pro | Pro | Gly | Pro | Pro | Pro |
|-----|-----|-----|-----|-----|-----|-----|-----|-----|-----|-----|-----|-----|-----|
| 1 | | | | 5 | | | | | 10 | | | | 15 |

Ala Gly Gly Gly Gly Ala Gly Gly Ala Gly Gly Gly Pro Pro
           20                25              30

Gly Pro Pro Gly Ala Gly Asp Arg Gly Gly Gly Pro Cys Gly Gly
       35            40               45

Gly Pro Gly Gly Ser Ala Gly Gly Pro Ser Gln Pro Pro Gly Gly
   50             55               60

Gly Gly Pro Gly Ile Arg Lys Asp Ala Phe Ala Asp Ala Val Gln Arg
65             70            75            80

Ala Arg Gln Ile Ala Ala Lys Ile Gly Gly Asp Ala Ala Thr Thr Val
             85          90            95

Asn Asn Ser Thr Pro Asp Phe Gly Phe Gly Gly Gln Lys Arg Gln Leu
        100             105           110

Glu Asp Gly Asp Gln Pro Glu Ser Arg Lys Leu Ala Ser Gln Gly Asp
      115            120            125

Ser Ile Ser Ser Gln Leu Gly Pro Ile His Pro Pro Pro Arg Thr Ser
   130             135            140

Met Thr Glu Glu Tyr Arg Val Pro Asp Gly Met Val Gly Leu Ile Ile
145            150            155            160

Gly Arg Gly Gly Glu Gln Ile Asn Lys Ile Gln Gln Asp Ser Gly Cys
            165            170            175

Lys Val Gln Ile Ser Pro Asp Ser Gly Gly Leu Pro Glu Arg Ser Val
        180             185           190

Ser Leu Thr Gly Ala Pro Glu Ser Val Gln Lys Ala Lys Met Met Leu
      195            200            205

Asp Asp Ile Val Ser Arg Gly Arg Gly Gly Pro Pro Gly Gln Phe His
210            215            220

Asp Asn Ala Asn Gly Gly Gln Asn Gly Thr Val Gln Glu Ile Met Ile
225            230            235            240

Pro Ala Gly Lys Ala Gly Leu Val Ile Gly Lys Gly Gly Glu Thr Ile
            245            250            255

Lys Gln Leu Gln Glu Arg Ala Gly Val Lys Met Ile Leu Ile Gln Asp
        260             265           270

Gly Ser Gln Asn Thr Asn Val Asp Lys Pro Leu Arg Ile Ile Gly Asp
      275            280            285

Pro Tyr Lys Val Gln Gln Ala Cys Glu Met Val Met Asp Ile Leu Arg
   290             295            300

Glu Arg Asp Gln Gly Gly Phe Gly Asp Arg Asn Glu Tyr Gly Ser Arg
305            310            315            320

Ile Gly Gly Gly Ile Asp Val Pro Val Pro Arg His Ser Val Gly Val
            325            330            335

Val Ile Gly Arg Ser Gly Glu Met Ile Lys Lys Ile Gln Asn Asp Ala
        340             345           350

Gly Val Arg Ile Gln Phe Lys Gln Asp Asp Gly Thr Gly Pro Glu Lys
      355            360            365

Ile Ala His Ile Met Gly Pro Pro Asp Arg Cys Glu His Ala Ala Arg

```
            370                 375                 380
Ile Ile Asn Asp Leu Leu Gln Ser Leu Arg Ser Gly Pro Pro Gly Pro
385                 390                 395                 400

Pro Gly Gly Pro Gly Met Pro Pro Gly Gly Arg Gly Arg Gly Arg Gly
                405                 410                 415

Gln Gly Asn Trp Gly Pro Pro Gly Gly Glu Met Thr Phe Ser Ile Pro
                420                 425                 430

Thr His Lys Cys Gly Leu Val Ile Gly Arg Gly Gly Glu Asn Val Lys
                435                 440                 445

Ala Ile Asn Gln Gln Thr Gly Ala Phe Val Glu Ile Ser Arg Gln Leu
450                 455                 460

Pro Pro Asn Gly Asp Pro Asn Phe Lys Leu Phe Ile Ile Arg Gly Ser
465                 470                 475                 480

Pro Gln Gln Ile Asp His Ala Lys Gln Leu Ile Glu Glu Lys Ile Glu
                485                 490                 495

Gly Pro Leu Cys Pro Val Gly Pro Gly Pro Gly Gly Pro Gly Pro Ala
                500                 505                 510

Gly Pro Met Gly Pro Phe Asn Pro Gly Pro Phe Asn Gln Gly Pro Pro
                515                 520                 525

Gly Ala Pro Pro His Ala Gly Gly Pro Pro His Gln Tyr Pro Pro
                530                 535                 540

Gln Gly Trp Gly Asn Thr Tyr Pro Gln Trp Gln Pro Ala Pro His
545                 550                 555                 560

Asp Pro Ser Lys Ala Ala Ala Ala Ala Asp Pro Asn Ala Ala Trp
                565                 570                 575

Ala Ala Tyr Tyr Ser His Tyr Tyr Gln Gln Pro Pro Gly Pro Val Pro
                580                 585                 590

Gly Pro Ala Pro Ala Pro Ala Ala Pro Ala Gln Gly Glu Pro Pro
                595                 600                 605

Gln Pro Pro Pro Thr Gly Gln Ser Asp Tyr Thr Lys Ala Trp Glu Glu
610                 615                 620

Tyr Tyr Lys Lys Ile Gly Gln Gln Pro Gln Gln Pro Gly Ala Pro Pro
625                 630                 635                 640

Gln Gln Asp Tyr Thr Lys Ala Trp Glu Glu Tyr Tyr Lys Lys Gln Ala
                645                 650                 655

Gln Val Ala Thr Gly Gly Pro Gly Ala Pro Pro Gly Ser Gln Pro
                660                 665                 670

Asp Tyr Ser Ala Ala Trp Ala Glu Tyr Tyr Arg Gln Gln Ala Ala Tyr
                675                 680                 685

Tyr Gly Gln Thr Pro Gly Pro Gly Gly Pro Gln Pro Pro Thr Gln
690                 695                 700

Gln Gly Gln Gln Gln Ala Gln
705                 710

<210> SEQ ID NO 13
<211> LENGTH: 2136
<212> TYPE: DNA
<213> ORGANISM: Artificial Sequence
<220> FEATURE:
<223> OTHER INFORMATION: FBP2-K122R coding sequence

<400> SEQUENCE: 13
atgagcgact acagcacagg cggaccacct ccaggaccac ctcctccagc tggcggtggc      60
ggaggtgctg gcggagctgg aggtggacct ccacctggac ctcccggcgc tggcgataga     120
```

| | |
|---|---|
| ggtggcggag gaccttgtgg gggcggacca ggtggtggat ctgccggtgg cccttctcag | 180 |
| cctcctggcg gagggggccc tggcatcaga aggatgcct tcgccgacgc cgtgcagcgg | 240 |
| gccagacaga tcgctgctaa gattggcggc gatgctgcca ccaccgtgaa caacagcacc | 300 |
| cccgacttcg gcttcggcgg ccagaaacgg cagctggaag atggcgacca gcccgagagc | 360 |
| aagaggctgg cctcccaggg cgacagcatc agcagccagc tgggccccat ccacccccca | 420 |
| cccagaacca gcatgaccga ggaataccgg gtgcccgacg catggtcgg actgatcatc | 480 |
| ggcagaggcg gcgagcagat caacaagatc cagcaggaca cggctgcaa ggtgcagatc | 540 |
| agccccgact ctggcggcct gcccgagaga tccgtgtctc tgactggcgc ccctgagagc | 600 |
| gtgcagaaag ccaagatgat gctggacgac atcgtgtccc ggggcagagg gggtcctcca | 660 |
| ggccagttcc acgacaatgc caacggcgga cagaacggca ccgtgcagga aatcatgatt | 720 |
| ccagccggca aggccggcct ggtcatcgga aagggcggcg agacaatcaa gcagctgcag | 780 |
| gaacgggctg gcgtcaagat gatcctgatc caggacggca gccagaacac caacgtggac | 840 |
| aagcccctgc ggatcatcgg ggatccttac aaagtgcagc aagcctgtga gatggtgatg | 900 |
| gacatcctcc gggaacgtga ccaaggcggc tttggggacc ggaatgagta cggatctcgg | 960 |
| attggcggag catcgatgt gccagtgccc aggcattctg ttggcgtggt cattggccgg | 1020 |
| agtggagaga tgatcaagaa gatccagaat gatgctggcg tgcggataca gttcaagcaa | 1080 |
| gatgacggga cagggcccga aagattgct catataatgg gccccccaga caggtgcgag | 1140 |
| cacgcagccc ggatcatcaa cgacctcctc cagagcctca ggagtggtcc cccaggtcct | 1200 |
| ccaggggggtc caggcatgcc cccggggggc cgaggccgag aagaggcca aggcaattgg | 1260 |
| ggtccccctg gcggggagat gaccttctcc atccccactc acaagtgtgg gctggtcatc | 1320 |
| ggccgaggtg gcgagaatgt gaaagccata accagcaga cggagccctt cgtagagatc | 1380 |
| tcccggcagc tgccacccaa cgggacccc aacttcaagt tgttcatcat ccggggttca | 1440 |
| ccccagcaga ttgaccacgc caagcagctt atcgaggaaa agatcgaggg tcctctctgc | 1500 |
| ccagttggac caggcccagg tgcccaggc cctgctggcc caatggggcc cttcaatcct | 1560 |
| gggcccttca accaggggcc acccgggggct ccccacatg ccgggggggcc ccctcctcac | 1620 |
| cagtacccac cccagggctg ggcaatacc taccccccagt ggcagccgcc tgctcctcat | 1680 |
| gacccaagca aagcagctgc agcggccgcg gaccccaacg ccgcgtgggc cgcctactac | 1740 |
| tcacactact accagcagcc cccgggcccc gtccccggcc ccgcaccggc ccctgcggcc | 1800 |
| ccaccggctc agggtgagcc ccctcagccc cacccaccg gccagtcgga ctacactaag | 1860 |
| gcctgggaag agtattacaa aaagatcggc cagcagcccc agcagcccgg agcgcccca | 1920 |
| cagcaggact acacgaaggc ttgggaggag tactacaaga gcaagcgca gtgccacc | 1980 |
| ggagggggtc caggagctcc cccaggctcc cagccagact acagtgccgc ctgggcggaa | 2040 |
| tattacagac agcaggccgc ttactacgga cagaccccag gtcctggcgg ccccagccg | 2100 |
| ccgcccacgc agcagggaca gcagcaggct caatga | 2136 |

<210> SEQ ID NO 14
<211> LENGTH: 711
<212> TYPE: PRT
<213> ORGANISM: Artificial Sequence
<220> FEATURE:
<223> OTHER INFORMATION: FBP2-K122R amino acid sequence

<400> SEQUENCE: 14

Met Ser Asp Tyr Ser Thr Gly Gly Pro Pro Gly Pro Pro Pro Pro

```
1               5                   10                  15
Ala Gly Gly Gly Gly Ala Gly Gly Ala Gly Gly Gly Pro Pro
                20                  25                  30
Gly Pro Pro Gly Ala Gly Asp Arg Gly Gly Gly Pro Cys Gly Gly
                35                  40                  45
Gly Pro Gly Gly Gly Ser Ala Gly Gly Pro Ser Gln Pro Pro Gly Gly
                50                  55                  60
Gly Gly Pro Gly Ile Arg Lys Asp Ala Phe Ala Asp Ala Val Gln Arg
65                  70                  75                  80
Ala Arg Gln Ile Ala Ala Lys Ile Gly Gly Asp Ala Ala Thr Thr Val
                85                  90                  95
Asn Asn Ser Thr Pro Asp Phe Gly Phe Gly Gly Gln Lys Arg Gln Leu
                100                 105                 110
Glu Asp Gly Asp Gln Pro Glu Ser Lys Arg Leu Ala Ser Gln Gly Asp
                115                 120                 125
Ser Ile Ser Ser Gln Leu Gly Pro Ile His Pro Pro Arg Thr Ser
130                 135                 140
Met Thr Glu Glu Tyr Arg Val Pro Asp Gly Met Val Gly Leu Ile Ile
145                 150                 155                 160
Gly Arg Gly Gly Glu Gln Ile Asn Lys Ile Gln Gln Asp Ser Gly Cys
                165                 170                 175
Lys Val Gln Ile Ser Pro Asp Ser Gly Gly Leu Pro Glu Arg Ser Val
                180                 185                 190
Ser Leu Thr Gly Ala Pro Glu Ser Val Gln Lys Ala Lys Met Met Leu
                195                 200                 205
Asp Asp Ile Val Ser Arg Gly Arg Gly Gly Pro Pro Gly Gln Phe His
210                 215                 220
Asp Asn Ala Asn Gly Gly Gln Asn Gly Thr Val Gln Glu Ile Met Ile
225                 230                 235                 240
Pro Ala Gly Lys Ala Gly Leu Val Ile Gly Lys Gly Gly Glu Thr Ile
                245                 250                 255
Lys Gln Leu Gln Glu Arg Ala Gly Val Lys Met Ile Leu Ile Gln Asp
                260                 265                 270
Gly Ser Gln Asn Thr Asn Val Asp Lys Pro Leu Arg Ile Ile Gly Asp
                275                 280                 285
Pro Tyr Lys Val Gln Gln Ala Cys Glu Met Val Met Asp Ile Leu Arg
                290                 295                 300
Glu Arg Asp Gln Gly Gly Phe Gly Asp Arg Asn Glu Tyr Gly Ser Arg
305                 310                 315                 320
Ile Gly Gly Gly Ile Asp Val Pro Val Pro Arg His Ser Val Gly Val
                325                 330                 335
Val Ile Gly Arg Ser Gly Glu Met Ile Lys Lys Ile Gln Asn Asp Ala
                340                 345                 350
Gly Val Arg Ile Gln Phe Lys Gln Asp Asp Gly Thr Gly Pro Glu Lys
                355                 360                 365
Ile Ala His Ile Met Gly Pro Pro Asp Arg Cys Glu His Ala Ala Arg
                370                 375                 380
Ile Ile Asn Asp Leu Leu Gln Ser Leu Arg Ser Gly Pro Pro Gly Pro
385                 390                 395                 400
Pro Gly Gly Pro Gly Met Pro Pro Gly Gly Arg Gly Arg Gly Arg Gly
                405                 410                 415
Gln Gly Asn Trp Gly Pro Pro Gly Gly Glu Met Thr Phe Ser Ile Pro
                420                 425                 430
```

```
Thr His Lys Cys Gly Leu Val Ile Gly Arg Gly Gly Glu Asn Val Lys
        435                 440                 445

Ala Ile Asn Gln Gln Thr Gly Ala Phe Val Glu Ile Ser Arg Gln Leu
    450                 455                 460

Pro Pro Asn Gly Asp Pro Asn Phe Lys Leu Phe Ile Ile Arg Gly Ser
465                 470                 475                 480

Pro Gln Gln Ile Asp His Ala Lys Gln Leu Ile Glu Glu Lys Ile Glu
                485                 490                 495

Gly Pro Leu Cys Pro Val Gly Pro Gly Pro Gly Gly Pro Gly Pro Ala
                500                 505                 510

Gly Pro Met Gly Pro Phe Asn Pro Gly Pro Phe Asn Gln Gly Pro Pro
            515                 520                 525

Gly Ala Pro Pro His Ala Gly Gly Pro Pro Pro His Gln Tyr Pro Pro
        530                 535                 540

Gln Gly Trp Gly Asn Thr Tyr Pro Gln Trp Gln Pro Pro Ala Pro His
545                 550                 555                 560

Asp Pro Ser Lys Ala Ala Ala Ala Ala Ala Asp Pro Asn Ala Ala Trp
                565                 570                 575

Ala Ala Tyr Tyr Ser His Tyr Tyr Gln Gln Pro Pro Gly Pro Val Pro
            580                 585                 590

Gly Pro Ala Pro Ala Pro Ala Ala Pro Pro Ala Gln Gly Glu Pro Pro
        595                 600                 605

Gln Pro Pro Pro Thr Gly Gln Ser Asp Tyr Thr Lys Ala Trp Glu Glu
610                 615                 620

Tyr Tyr Lys Lys Ile Gly Gln Gln Pro Gln Pro Gly Ala Pro Pro
625                 630                 635                 640

Gln Gln Asp Tyr Thr Lys Ala Trp Glu Glu Tyr Tyr Lys Lys Gln Ala
                645                 650                 655

Gln Val Ala Thr Gly Gly Pro Gly Ala Pro Pro Gly Ser Gln Pro
            660                 665                 670

Asp Tyr Ser Ala Ala Trp Ala Glu Tyr Tyr Arg Gln Gln Ala Ala Tyr
        675                 680                 685

Tyr Gly Gln Thr Pro Gly Pro Gly Gly Pro Gln Pro Pro Thr Gln
        690                 695                 700

Gln Gly Gln Gln Gln Ala Gln
705                 710

<210> SEQ ID NO 15
<211> LENGTH: 2136
<212> TYPE: DNA
<213> ORGANISM: Artificial Sequence
<220> FEATURE:
<223> OTHER INFORMATION: FBP2-K121,122R coding sequence

<400> SEQUENCE: 15
atgagcgact acagcacagg cggaccacct ccaggaccac ctcctccagc tggcggtggc      60
ggaggtgctg gcggagctgg aggtggacct ccacctggac ctcccggcgc tggcgataga     120
ggtggcggag gaccttgtgg gggcggacca ggtggtggat ctgccggtgg cccttctcag     180
cctcctggcg agggggccc tggcatcaga aaggatgcct cgccgacgc cgtgcagcgg       240 gccagacaga tcgctgctaa gattggcggc gatgctgcca ccaccgtgaa caacagcacc     300
cccgacttcg gcttcggcgg ccagaaacgg cagctggaag atggcgacca gcccgagagc     360
aggaggctgg cctcccaggg cgacagcatc agcagccagc tgggccccat ccaccccccca    420
```

-continued

```
cccagaacca gcatgaccga ggaataccgg gtgcccgacg gcatggtcgg actgatcatc      480
ggcagaggcg gcgagcagat caacaagatc cagcaggaca gcggctgcaa ggtgcagatc      540
agccccgact ctggcggcct gcccgagaga tccgtgtctc tgactggcgc ccctgagagc      600
gtgcagaaag ccaagatgat gctggacgac atcgtgtccc ggggcagagg gggtcctcca      660
ggccagttcc acgacaatgc caacggcgga cagaacggca ccgtgcagga aatcatgatt      720
ccagccggca aggccggcct ggtcatcgga aagggcggcg agacaatcaa gcagctgcag      780
gaacgggctg gcgtcaagat gatcctgatc aggacggca gccagaacac caacgtggac       840
aagcccctgc ggatcatcgg ggatccttac aaagtgcagc aagcctgtga gatggtgatg      900
gacatcctcc gggaacgtga ccaaggcggc tttggggacc ggaatgagta cggatctcgg      960
attggcggag catcgatgt gccagtgccc aggcattctg ttggcgtggt cattggccgg      1020
agtggagaga tgatcaagaa gatccagaat gatgctggcg tgcggataca gttcaagcaa     1080
gatgacggga cagggcccga gaagattgct catataatgg ggcccccaga caggtgcgag     1140
cacgcagccc ggatcatcaa cgacctcctc cagagcctca ggagtggtcc cccaggtcct     1200
ccagggggtc caggcatgcc cccggggggc cgaggccgag aagaggcca aggcaattgg      1260
ggtccccctg gcggggagat gaccttctcc atccccactc acaagtgtgg gctggtcatc     1320
ggccgaggtg gcgagaatgt gaaagccata accagcaga cgggagcctt cgtagagatc      1380
tcccggcagc tgccacccaa cggggacccc aacttcaagt tgttcatcat ccggggttca     1440
ccccagcaga ttgaccacgc caagcagctt atcgaggaaa agatcgaggg tcctctctgc     1500
ccagttggac caggcccagg tggcccaggc cctgctggcc caatgggcc cttcaatcct     1560
ggcccttca accaggggcc acccggggct ccccacatg ccggggggcc ccctcctcac      1620
cagtacccac cccagggctg gggcaatacc tacccccagt ggcagccgcc tgctcctcat     1680
gacccaagca aagcagctgc agcggccgcg gaccccaacg ccgcgtgggc cgcctactac     1740
tcacactact accagcagcc cccggggccc gtccccggcc ccgcaccggc ccctgcggcc     1800
ccaccggctc agggtgagcc ccctcagccc ccacccaccg gccagtcgga ctacactaag     1860
gcctgggaag agtattacaa aaagatcggc cagcagcccc agcagcccgg agcgccccca     1920
cagcaggact acacgaaggc ttgggaggag tactacaaga gcaagcgca gtggccacc      1980
ggagggggtc caggagctcc cccaggctcc cagccagact acagtgccgc ctgggcggaa    2040
tattacagac agcaggccgc ttactacgga cagaccccag gtcctggcgg ccccccagccg   2100
ccgcccacgc agcagggaca gcagcaggct caatga                              2136
```

<210> SEQ ID NO 16
<211> LENGTH: 711
<212> TYPE: PRT
<213> ORGANISM: Artificial Sequence
<220> FEATURE:
<223> OTHER INFORMATION: FBP2-K121,122R amino acid sequence

<400> SEQUENCE: 16

```
Met Ser Asp Tyr Ser Thr Gly Gly Pro Pro Pro Gly Pro Pro Pro
1               5                   10                  15

Ala Gly Gly Gly Gly Ala Gly Gly Ala Gly Gly Pro Pro
            20                  25                  30

Gly Pro Pro Gly Ala Gly Asp Arg Gly Gly Gly Gly Pro Cys Gly Gly
        35                  40                  45

Gly Pro Gly Gly Gly Ser Ala Gly Gly Pro Ser Gln Pro Pro Gly Gly
    50                  55                  60
```

```
Gly Gly Pro Gly Ile Arg Lys Asp Ala Phe Ala Asp Ala Val Gln Arg
65                  70                  75                  80

Ala Arg Gln Ile Ala Ala Lys Ile Gly Gly Asp Ala Ala Thr Thr Val
                85                  90                  95

Asn Asn Ser Thr Pro Asp Phe Gly Phe Gly Gly Gln Lys Arg Gln Leu
            100                 105                 110

Glu Asp Gly Asp Gln Pro Glu Ser Arg Arg Leu Ala Ser Gln Gly Asp
        115                 120                 125

Ser Ile Ser Ser Gln Leu Gly Pro Ile His Pro Pro Arg Thr Ser
    130                 135                 140

Met Thr Glu Glu Tyr Arg Val Pro Asp Gly Met Val Gly Leu Ile Ile
145                 150                 155                 160

Gly Arg Gly Gly Glu Gln Ile Asn Lys Ile Gln Gln Asp Ser Gly Cys
                165                 170                 175

Lys Val Gln Ile Ser Pro Asp Ser Gly Gly Leu Pro Glu Arg Ser Val
            180                 185                 190

Ser Leu Thr Gly Ala Pro Glu Ser Val Gln Lys Ala Lys Met Met Leu
        195                 200                 205

Asp Asp Ile Val Ser Arg Gly Arg Gly Gly Pro Pro Gly Gln Phe His
210                 215                 220

Asp Asn Ala Asn Gly Gln Asn Gly Thr Val Gln Glu Ile Met Ile
225                 230                 235                 240

Pro Ala Gly Lys Ala Gly Leu Val Ile Gly Lys Gly Gly Glu Thr Ile
                245                 250                 255

Lys Gln Leu Gln Glu Arg Ala Gly Val Lys Met Ile Leu Ile Gln Asp
            260                 265                 270

Gly Ser Gln Asn Thr Asn Val Asp Lys Pro Leu Arg Ile Ile Gly Asp
        275                 280                 285

Pro Tyr Lys Val Gln Gln Ala Cys Glu Met Val Met Asp Ile Leu Arg
            290                 295                 300

Glu Arg Asp Gln Gly Gly Phe Gly Asp Arg Asn Glu Tyr Gly Ser Arg
305                 310                 315                 320

Ile Gly Gly Gly Ile Asp Val Pro Val Pro Arg His Ser Val Gly Val
                325                 330                 335

Val Ile Gly Arg Ser Gly Glu Met Ile Lys Lys Ile Gln Asn Asp Ala
            340                 345                 350

Gly Val Arg Ile Gln Phe Lys Gln Asp Asp Gly Thr Gly Pro Glu Lys
        355                 360                 365

Ile Ala His Ile Met Gly Pro Pro Asp Arg Cys Glu His Ala Ala Arg
    370                 375                 380

Ile Ile Asn Asp Leu Leu Gln Ser Leu Arg Ser Gly Pro Pro Gly Pro
385                 390                 395                 400

Pro Gly Pro Gly Met Pro Pro Gly Gly Arg Gly Arg Gly Arg Gly
                405                 410                 415

Gln Gly Asn Trp Gly Pro Pro Gly Gly Glu Met Thr Phe Ser Ile Pro
            420                 425                 430

Thr His Lys Cys Gly Leu Val Ile Gly Arg Gly Gly Glu Asn Val Lys
        435                 440                 445

Ala Ile Asn Gln Gln Thr Gly Ala Phe Val Glu Ile Ser Arg Gln Leu
    450                 455                 460

Pro Pro Asn Gly Asp Pro Asn Phe Lys Leu Phe Ile Ile Arg Gly Ser
465                 470                 475                 480
```

```
Pro Gln Gln Ile Asp His Ala Lys Gln Leu Ile Glu Glu Lys Ile Glu
                485                 490                 495
Gly Pro Leu Cys Pro Val Gly Pro Gly Pro Gly Gly Pro Gly Pro Ala
            500                 505                 510
Gly Pro Met Gly Pro Phe Asn Pro Gly Pro Phe Asn Gln Gly Pro Pro
            515                 520                 525
Gly Ala Pro Pro His Ala Gly Gly Pro Pro His Gln Tyr Pro Pro
            530                 535                 540
Gln Gly Trp Gly Asn Thr Tyr Pro Gln Trp Gln Pro Ala Pro His
545                 550                 555                 560
Asp Pro Ser Lys Ala Ala Ala Ala Ala Asp Pro Asn Ala Ala Trp
                565                 570                 575
Ala Ala Tyr Tyr Ser His Tyr Tyr Gln Gln Pro Pro Gly Pro Val Pro
            580                 585                 590
Gly Pro Ala Pro Ala Pro Ala Ala Pro Pro Ala Gln Gly Glu Pro Pro
            595                 600                 605
Gln Pro Pro Pro Thr Gly Gln Ser Asp Tyr Thr Lys Ala Trp Glu Glu
            610                 615                 620
Tyr Tyr Lys Lys Ile Gly Gln Gln Pro Gln Gln Pro Gly Ala Pro Pro
625                 630                 635                 640
Gln Gln Asp Tyr Thr Lys Ala Trp Glu Glu Tyr Tyr Lys Lys Gln Ala
                645                 650                 655
Gln Val Ala Thr Gly Gly Gly Pro Gly Ala Pro Pro Gly Ser Gln Pro
            660                 665                 670
Asp Tyr Ser Ala Ala Trp Ala Glu Tyr Tyr Arg Gln Gln Ala Ala Tyr
            675                 680                 685
Tyr Gly Gln Thr Pro Gly Pro Gly Gly Pro Gln Pro Pro Thr Gln
            690                 695                 700
Gln Gly Gln Gln Gln Ala Gln
705                 710

<210> SEQ ID NO 17
<211> LENGTH: 33
<212> TYPE: DNA
<213> ORGANISM: Artificial Sequence
<220> FEATURE:
<223> OTHER INFORMATION: Forward primer FBP1-F1

<400> SEQUENCE: 17
aagcttgcgg ccgcgatggc agactattca aca                              33

<210> SEQ ID NO 18
<211> LENGTH: 32
<212> TYPE: DNA
<213> ORGANISM: Artificial Sequence
<220> FEATURE:
<223> OTHER INFORMATION: Reverse primer FBP1-R1

<400> SEQUENCE: 18
ggtaccgata tcagttattg gccctgaggt gc                               32

<210> SEQ ID NO 19
<211> LENGTH: 35
<212> TYPE: DNA
<213> ORGANISM: Artificial Sequence
<220> FEATURE:
<223> OTHER INFORMATION: Reverse primer FBP1-R2

<400> SEQUENCE: 19
```
ggtaccgata tcagttatcc catgttccag ttgcc                                    35

<210> SEQ ID NO 20
<211> LENGTH: 36
<212> TYPE: DNA
<213> ORGANISM: Artificial Sequence
<220> FEATURE:
<223> OTHER INFORMATION: Forward primer FBP1-F2

<400> SEQUENCE: 20
aagcttgcgg ccgcgatgcc acctggtgga ctacag                                   36

<210> SEQ ID NO 21
<211> LENGTH: 35
<212> TYPE: DNA
<213> ORGANISM: Artificial Sequence
<220> FEATURE:
<223> OTHER INFORMATION: Reverse primer FBP1-R3

<400> SEQUENCE: 21
ggtaccgata tcagttatat gagttgccga gcata                                    35

<210> SEQ ID NO 22
<211> LENGTH: 39
<212> TYPE: DNA
<213> ORGANISM: Artificial Sequence
<220> FEATURE:
<223> OTHER INFORMATION: Forward primer FBP1-F3

<400> SEQUENCE: 22
aagcttgcgg ccgcgatgaa tgcagttcaa gaaatcatg                                39

<210> SEQ ID NO 23
<211> LENGTH: 32
<212> TYPE: DNA
<213> ORGANISM: Artificial Sequence
<220> FEATURE:
<223> OTHER INFORMATION: Forward primer

<400> SEQUENCE: 23
gctctagaat ggcagactat tcaacagtgc ct                                       32

<210> SEQ ID NO 24
<211> LENGTH: 30
<212> TYPE: DNA
<213> ORGANISM: Artificial Sequence
<220> FEATURE:
<223> OTHER INFORMATION: Reverse primer

<400> SEQUENCE: 24
cggggtacct cccatgttcc agttgccttg                                          30

<210> SEQ ID NO 25
<211> LENGTH: 66
<212> TYPE: DNA
<213> ORGANISM: Artificial Sequence
<220> FEATURE:
<223> OTHER INFORMATION: Forward primer FBP1-MF1

<400> SEQUENCE: 25
agtgttcagg ctaaaaatcc taaaaaacct aaacctaaaa acgaaaaag aaaaagaggt          60 caaggc                                                                   66

<210> SEQ ID NO 26
<211> LENGTH: 66

```
<212> TYPE: DNA
<213> ORGANISM: Artificial Sequence
<220> FEATURE:
<223> OTHER INFORMATION: Reverse primer FBP1-MR1

<400> SEQUENCE: 26
gccttgacct cttttctttt ttcgtttttt aggtttaggt ttttaggat ttttagcctg      60 aacact                                                                66

<210> SEQ ID NO 27
<211> LENGTH: 63
<212> TYPE: DNA
<213> ORGANISM: Artificial Sequence
<220> FEATURE:
<223> OTHER INFORMATION: Forward primer FBP1-MF2

<400> SEQUENCE: 27
ggaagaggta gaaacaaaa aaactggaac atgaaccac ctaaaaaact acaggaattt       60
aat                                                                   63

<210> SEQ ID NO 28
<211> LENGTH: 63
<212> TYPE: DNA
<213> ORGANISM: Artificial Sequence
<220> FEATURE:
<223> OTHER INFORMATION: Reverse primer FBP1-MR2

<400> SEQUENCE: 28
attaaattcc tgtagttttt taggtggttt catgttccag tttttttgtt ttctacctct    60
tcc                                                                   63

<210> SEQ ID NO 29
<211> LENGTH: 21
<212> TYPE: DNA
<213> ORGANISM: Artificial Sequence
<220> FEATURE:
<223> OTHER INFORMATION: Forward primer FBP1-MF3

<400> SEQUENCE: 29
agaggtagaa aacaaggcaa c                                               21

<210> SEQ ID NO 30
<211> LENGTH: 21
<212> TYPE: DNA
<213> ORGANISM: Artificial Sequence
<220> FEATURE:
<223> OTHER INFORMATION: Reverse primer FBP1-MR3

<400> SEQUENCE: 30
gttgccttgt tttctacctc t                                               21

<210> SEQ ID NO 31
<211> LENGTH: 21
<212> TYPE: DNA
<213> ORGANISM: Artificial Sequence
<220> FEATURE:
<223> OTHER INFORMATION: Forward primer FBP1-MF4

<400> SEQUENCE: 31
agaggtcaaa aaaactggaa c                                               21

<210> SEQ ID NO 32
<211> LENGTH: 21
<212> TYPE: DNA
```

<213> ORGANISM: Artificial Sequence
<220> FEATURE:
<223> OTHER INFORMATION: Reverse primer FBP1-MR4

<400> SEQUENCE: 32
gttccagttt ttttgacctc t        21

<210> SEQ ID NO 33
<211> LENGTH: 21
<212> TYPE: DNA
<213> ORGANISM: Artificial Sequence
<220> FEATURE:
<223> OTHER INFORMATION: Forward primer FBP1-MF5

<400> SEQUENCE: 33
tggaacatga aaccacctgg t        21

<210> SEQ ID NO 34
<211> LENGTH: 21
<212> TYPE: DNA
<213> ORGANISM: Artificial Sequence
<220> FEATURE:
<223> OTHER INFORMATION: Reverse primer FBP1-MR5

<400> SEQUENCE: 34
accaggtggt ttcatgttcc a        21

<210> SEQ ID NO 35
<211> LENGTH: 21
<212> TYPE: DNA
<213> ORGANISM: Artificial Sequence
<220> FEATURE:
<223> OTHER INFORMATION: Forward primer FBP1-MF6

<400> SEQUENCE: 35
ggaccaccta aaggactaca g        21

<210> SEQ ID NO 36
<211> LENGTH: 21
<212> TYPE: DNA
<213> ORGANISM: Artificial Sequence
<220> FEATURE:
<223> OTHER INFORMATION: Reverse primer FBP1-MR6

<400> SEQUENCE: 36
ctgtagtcct ttaggtggtc c        21

<210> SEQ ID NO 37
<211> LENGTH: 21
<212> TYPE: DNA
<213> ORGANISM: Artificial Sequence
<220> FEATURE:
<223> OTHER INFORMATION: Forward primer FBP1-MF7

<400> SEQUENCE: 37
ccacctggta aactacagga a        21

<210> SEQ ID NO 38
<211> LENGTH: 21
<212> TYPE: DNA
<213> ORGANISM: Artificial Sequence
<220> FEATURE:
<223> OTHER INFORMATION: Reverse primer FBP1-MR7

<400> SEQUENCE: 38
ttcctgtagt ttaccaggtg g        21

<210> SEQ ID NO 39
<211> LENGTH: 68
<212> TYPE: DNA
<213> ORGANISM: Artificial Sequence
<220> FEATURE:
<223> OTHER INFORMATION: Reverse primer FBP1-HA-R1

<400> SEQUENCE: 39
ggtaccgata tcagttaagc gtaatctgga acatcgtatg ggtaagagcc accttggccc    60
tgaggtgc    68

<210> SEQ ID NO 40
<211> LENGTH: 35
<212> TYPE: DNA
<213> ORGANISM: Artificial Sequence
<220> FEATURE:
<223> OTHER INFORMATION: Forward primer FBP1-WMF1

<400> SEQUENCE: 40
ccattcctag gttcgcagtc ggtatagtta tagga    35

<210> SEQ ID NO 41
<211> LENGTH: 35
<212> TYPE: DNA
<213> ORGANISM: Artificial Sequence
<220> FEATURE:
<223> OTHER INFORMATION: Reverse primer FBP1-WMR1

<400> SEQUENCE: 41
tcctataact ataccgactg cgaacctagg aatgg    35

<210> SEQ ID NO 42
<211> LENGTH: 32
<212> TYPE: DNA
<213> ORGANISM: Artificial Sequence
<220> FEATURE:
<223> OTHER INFORMATION: Reverse primer FBP1-WMR2

<400> SEQUENCE: 42
agtcattttg aggagctccc ccataaccat ag    32

<210> SEQ ID NO 43
<211> LENGTH: 32
<212> TYPE: DNA
<213> ORGANISM: Artificial Sequence
<220> FEATURE:
<223> OTHER INFORMATION: Forward primer FBP1-WMF2

<400> SEQUENCE: 43
ctatggttat gggggagctc ctcaaaatga ct    32

<210> SEQ ID NO 44
<211> LENGTH: 1116
<212> TYPE: DNA
<213> ORGANISM: Artificial Sequence
<220> FEATURE:
<223> OTHER INFORMATION: FBP11-371-WM coding sequence

<400> SEQUENCE: 44
atggcagact attcaacagt gcctcccccc tcttctggct cagctggtgg cggtggtggc    60
ggcggtggtg gtggaggagt taacgacgct ttcaaagatg cactgcagag agcccggcag    120
attgcagcaa aaattggagg tgatgcaggg acatcactga attcaaatga ctatggttat    180

```
gggggacaaa aaagacctttt agaagatgga gatcaaccag atgctaagaa agttgctcct    240
caaaatgact cttttggaac acagttacca ccgatgcatc agcagcaaag cagatctgta    300
aggacagaag aatacaaagt tccagatgga atggttggat tcataattgg cagaggaggt    360
gaacagatct cacgcataca acaggaatct ggatgcagaa tacagatagc tcctgacagt    420
ggtggccttc agaaaggtc ctgtatgtta actggaacac ctgaatctgt ccagtcagca     480
aaacggttac tggaccagat tgttgaaaaa ggaagaccag ctcctggctt ccatcatggc    540
gatggaccgg gaaatgcagt tcaagaaatc atgattccag ctagcaaggc aggattagtc    600
attggaaaag ggggagaaac tattaaacag cttcaggaac gggctggagt taaaatggtt    660
atgattcaag acgggccgca gaacactggt gctgacaaac ctcttaggat tacaggagac    720
ccatataaag ttcaacaagc caaggaaatg gtgttagagt taattcgtga tcaaggcgt    780 ttcagagaag ttcggaatga gtatgggtca agaataggag gaaatgaagg gatagatgtc    840
cccattccta ggttcgcagt cggtatagtt ataggaagaa atggagagat gatcaaaaaa    900
atacaaaatg atgctggtgt tcgcattcag tttaagccag atgatgggac aacacccgaa    960
aggatagcac aaataacagg acctccagac cgatgtcaac atgctgcaga aattattaca   1020
gaccttcttc gaagtgttca ggctggtaat cctggtggac ctggacctgg tggtcgagga   1080
agaggtagag gtcaaggcaa ctggaacatg ggataa                             1116
```

<210> SEQ ID NO 45
<211> LENGTH: 1068
<212> TYPE: DNA
<213> ORGANISM: Artificial Sequence
<220> FEATURE:
<223> OTHER INFORMATION: FBP11-371-WM-delNLS coding sequence

<400> SEQUENCE: 45

```
atggcagact attcaacagt gcctccccc tcttctggct cagctggtgg cggtggtggc     60
ggcggtggtg gtggaggagt taacgacgct ttcaaagatg cactgcagag agcccggcag    120
attgcagcaa aaattggagg tgatgcaggg acatcactga attcaaatga ctatggttat    180
gggggagctc ctcaaaatga ctcttttgga acacagttac caccgatgca tcagcagcaa    240
agcagatctg taaggacaga agaatacaaa gttccagatg gaatggttgg attcataatt    300
ggcagaggag gtgaacagat ctcacgcata caacaggaat ctggatgcag aatacagata    360
gctcctgaca gtggtggcct tccagaaagg tcctgtatgt taactggaac acctgaatct    420
gtccagtcag caaaacggtt actggaccag attgttgaaa aaggaagacc agctcctggc    480
ttccatcatg gcgatggacc gggaaatgca gttcaagaaa tcatgattcc agctagcaag    540
gcaggattag tcattggaaa aggggagaaa actattaaac agcttcagga acgggctgga    600
gttaaaatgg ttatgattca agacgggccg cagaacactg gtgctgacaa acctcttagg    660
attacaggag acccatataa agttcaacaa gccaaggaaa tggtgttaga gttaattcgt    720
gatcaaggcg gtttcagaga agttcggaat gagtatgggt caagaatagg aggaaatgaa    780
gggatagatg tccccattcc taggttcgca gtcggtatag ttataggaag aaatggagag    840
atgatcaaaa aatacaaaa tgatgctggt gttcgcattc agtttaagcc agatgatggg    900
acaacacccg aaaggatagc acaaataaca ggacctccag accgatgtca acatgctgca    960
gaaattatta cagaccttct tcgaagtgtt caggctggta atcctggtgg acctggacct   1020
ggtggtcgag gaagaggtag aggtcaaggc aactggaaca tgggataa                 1068
```

<210> SEQ ID NO 46
<211> LENGTH: 355
<212> TYPE: PRT
<213> ORGANISM: Artificial Sequence
<220> FEATURE:
<223> OTHER INFORMATION: FBP11-371-WM-delNLS protein

<400> SEQUENCE: 46

```
Met Ala Asp Tyr Ser Thr Val Pro Pro Ser Ser Gly Ser Ala Gly
1               5                   10                  15

Gly Gly Gly Gly Gly Gly Gly Gly Gly Val Asn Asp Ala Phe Lys
            20                  25                  30

Asp Ala Leu Gln Arg Ala Arg Gln Ile Ala Ala Lys Ile Gly Gly Asp
        35                  40                  45

Ala Gly Thr Ser Leu Asn Ser Asn Asp Tyr Gly Tyr Gly Gly Ala Pro
    50                  55                  60

Gln Asn Asp Ser Phe Gly Thr Gln Leu Pro Pro Met His Gln Gln Gln
65                  70                  75                  80

Ser Arg Ser Val Arg Thr Glu Glu Tyr Lys Val Pro Asp Gly Met Val
                85                  90                  95

Gly Phe Ile Ile Gly Arg Gly Gly Glu Gln Ile Ser Arg Ile Gln Gln
            100                 105                 110

Glu Ser Gly Cys Arg Ile Gln Ile Ala Pro Asp Ser Gly Gly Leu Pro
        115                 120                 125

Glu Arg Ser Cys Met Leu Thr Gly Thr Pro Glu Ser Val Gln Ser Ala
    130                 135                 140

Lys Arg Leu Leu Asp Gln Ile Val Glu Lys Gly Arg Pro Ala Pro Gly
145                 150                 155                 160

Phe His His Gly Asp Gly Pro Gly Asn Ala Val Gln Glu Ile Met Ile
                165                 170                 175

Pro Ala Ser Lys Ala Gly Leu Val Ile Gly Lys Gly Gly Glu Thr Ile
            180                 185                 190

Lys Gln Leu Gln Glu Arg Ala Gly Val Lys Met Val Met Ile Gln Asp
        195                 200                 205

Gly Pro Gln Asn Thr Gly Ala Asp Lys Pro Leu Arg Ile Thr Gly Asp
    210                 215                 220

Pro Tyr Lys Val Gln Gln Ala Lys Glu Met Val Leu Glu Leu Ile Arg
225                 230                 235                 240

Asp Gln Gly Gly Phe Arg Glu Val Arg Asn Glu Tyr Gly Ser Arg Ile
                245                 250                 255

Gly Gly Asn Glu Gly Ile Asp Val Pro Ile Pro Arg Phe Ala Val Gly
            260                 265                 270

Ile Val Ile Gly Arg Asn Gly Glu Met Ile Lys Lys Ile Gln Asn Asp
        275                 280                 285

Ala Gly Val Arg Ile Gln Phe Lys Pro Asp Asp Gly Thr Thr Pro Glu
    290                 295                 300

Arg Ile Ala Gln Ile Thr Gly Pro Pro Asp Arg Cys Gln His Ala Ala
305                 310                 315                 320

Glu Ile Ile Thr Asp Leu Leu Arg Ser Val Gln Ala Gly Asn Pro Gly
                325                 330                 335

Gly Pro Gly Pro Gly Gly Arg Gly Arg Gly Arg Gly Gln Gly Asn Trp
            340                 345                 350

Asn Met Gly
        355
```

```
<210> SEQ ID NO 47
<211> LENGTH: 32
<212> TYPE: DNA
<213> ORGANISM: Artificial Sequence
<220> FEATURE:
<223> OTHER INFORMATION: Forward primer FBP2-F1

<400> SEQUENCE: 47
accgaattcg ccaccatgag cgactacagc ac                              32

<210> SEQ ID NO 48
<211> LENGTH: 33
<212> TYPE: DNA
<213> ORGANISM: Artificial Sequence
<220> FEATURE:
<223> OTHER INFORMATION: Reverse primer FBP2-R1

<400> SEQUENCE: 48
gtaccgatat cagttgagcc tgctgctgtc cct                             33

<210> SEQ ID NO 49
<211> LENGTH: 21
<212> TYPE: DNA
<213> ORGANISM: Artificial Sequence
<220> FEATURE:
<223> OTHER INFORMATION: Forward primer FBP2-F109

<400> SEQUENCE: 49
ggcggccaga gacggcagct g                                          21

<210> SEQ ID NO 50
<211> LENGTH: 21
<212> TYPE: DNA
<213> ORGANISM: Artificial Sequence
<220> FEATURE:
<223> OTHER INFORMATION: Reverse primer FBP2-R109

<400> SEQUENCE: 50
cagctgccgt ctctggccgc c                                          21

<210> SEQ ID NO 51
<211> LENGTH: 21
<212> TYPE: DNA
<213> ORGANISM: Artificial Sequence
<220> FEATURE:
<223> OTHER INFORMATION: Forward primer FBP2-F121

<400> SEQUENCE: 51
cccgagagca ggaagctggc c                                          21

<210> SEQ ID NO 52
<211> LENGTH: 21
<212> TYPE: DNA
<213> ORGANISM: Artificial Sequence
<220> FEATURE:
<223> OTHER INFORMATION: Reverse primer FBP2-R121

<400> SEQUENCE: 52
ggccagcttc ctgctctcgg g                                          21

<210> SEQ ID NO 53
<211> LENGTH: 21
<212> TYPE: DNA
<213> ORGANISM: Artificial Sequence
<220> FEATURE:
<223> OTHER INFORMATION: Forward primer FBP2-F122
```

```
<400> SEQUENCE: 53
gagagcaaga ggctggcctc c                                              21

<210> SEQ ID NO 54
<211> LENGTH: 21
<212> TYPE: DNA
<213> ORGANISM: Artificial Sequence
<220> FEATURE:
<223> OTHER INFORMATION: Reverse primer FBP2-R122

<400> SEQUENCE: 54
ggaggccagc ctcttgctct c                                              21

<210> SEQ ID NO 55
<211> LENGTH: 21
<212> TYPE: DNA
<213> ORGANISM: Artificial Sequence
<220> FEATURE:
<223> OTHER INFORMATION: Forward primer FBP2-F251

<400> SEQUENCE: 55
gtcatcggaa ggggcggcga g                                              21

<210> SEQ ID NO 56
<211> LENGTH: 21
<212> TYPE: DNA
<213> ORGANISM: Artificial Sequence
<220> FEATURE:
<223> OTHER INFORMATION: Reverse primer FBP2-R251

<400> SEQUENCE: 56
ctcgccgccc cttccgatga c                                              21

<210> SEQ ID NO 57
<211> LENGTH: 21
<212> TYPE: DNA
<213> ORGANISM: Artificial Sequence
<220> FEATURE:
<223> OTHER INFORMATION: Forward primer FBP2-F628

<400> SEQUENCE: 57
tattacaaaa ggatcggcca g                                              21

<210> SEQ ID NO 58
<211> LENGTH: 21
<212> TYPE: DNA
<213> ORGANISM: Artificial Sequence
<220> FEATURE:
<223> OTHER INFORMATION: Reverse primer FBP2-R628

<400> SEQUENCE: 58
ctggccgatc tttttgtaat a                                              21

<210> SEQ ID NO 59
<211> LENGTH: 21
<212> TYPE: DNA
<213> ORGANISM: Artificial Sequence
<220> FEATURE:
<223> OTHER INFORMATION: Forward primer FBP2-F646

<400> SEQUENCE: 59
gactacacga gggcttggga g                                              21

<210> SEQ ID NO 60
<211> LENGTH: 21
```

<212> TYPE: DNA
<213> ORGANISM: Artificial Sequence
<220> FEATURE:
<223> OTHER INFORMATION: Reverse primer FBP2-R646

<400> SEQUENCE: 60
ctcccaagcc ctcgtgtagt c                                          21

<210> SEQ ID NO 61
<211> LENGTH: 21
<212> TYPE: DNA
<213> ORGANISM: Artificial Sequence
<220> FEATURE:
<223> OTHER INFORMATION: Forward primer FBP2-F654

<400> SEQUENCE: 61
tactacaaga ggcaagcgca a                                          21

<210> SEQ ID NO 62
<211> LENGTH: 21
<212> TYPE: DNA
<213> ORGANISM: Artificial Sequence
<220> FEATURE:
<223> OTHER INFORMATION: Reverse primer FBP2-R654

<400> SEQUENCE: 62
ttgcgcttgc ctcttgtagt a                                          21

<210> SEQ ID NO 63
<211> LENGTH: 24
<212> TYPE: DNA
<213> ORGANISM: Artificial Sequence
<220> FEATURE:
<223> OTHER INFORMATION: Forward primer FBP2-F121/122

<400> SEQUENCE: 63
cccgagagca ggaggctggc ctcc                                       24

<210> SEQ ID NO 64
<211> LENGTH: 24
<212> TYPE: DNA
<213> ORGANISM: Artificial Sequence
<220> FEATURE:
<223> OTHER INFORMATION: Reverse primer FBP2-R121/122

<400> SEQUENCE: 64
ggaggccagc ctcctgctct cggg                                       24

<210> SEQ ID NO 65
<211> LENGTH: 21
<212> TYPE: DNA
<213> ORGANISM: Artificial Sequence
<220> FEATURE:
<223> OTHER INFORMATION: Forward primer FBP2-F71

<400> SEQUENCE: 65
tggcatcaga gaggatgcct t                                          21

<210> SEQ ID NO 66
<211> LENGTH: 21
<212> TYPE: DNA
<213> ORGANISM: Artificial Sequence
<220> FEATURE:
<223> OTHER INFORMATION: Reverse primer FBP2-R71

<400> SEQUENCE: 66
aaggcatcct ctctgatgcc a                                    21

<210> SEQ ID NO 67
<211> LENGTH: 21
<212> TYPE: DNA
<213> ORGANISM: Artificial Sequence
<220> FEATURE:
<223> OTHER INFORMATION: Forward primer FBP2-F87

<400> SEQUENCE: 67
atcgctgcta ggattggcgg c                                    21

<210> SEQ ID NO 68
<211> LENGTH: 21
<212> TYPE: DNA
<213> ORGANISM: Artificial Sequence
<220> FEATURE:
<223> OTHER INFORMATION: Reverse primer FBP2-R87

<400> SEQUENCE: 68
gccgccaatc ctagcagcga t                                    21

<210> SEQ ID NO 69
<211> LENGTH: 27
<212> TYPE: DNA
<213> ORGANISM: Artificial Sequence
<220> FEATURE:
<223> OTHER INFORMATION: Forward primer 2Apro-F1

<400> SEQUENCE: 69
ccggaattcg ggaaatttgg acagcag                              27

<210> SEQ ID NO 70
<211> LENGTH: 31
<212> TYPE: DNA
<213> ORGANISM: Artificial Sequence
<220> FEATURE:
<223> OTHER INFORMATION: Reverse primer 2Apro-R1

<400> SEQUENCE: 70
cacgatgcgg ccgctcctgc tccatggctt c                         31

<210> SEQ ID NO 71
<211> LENGTH: 21
<212> TYPE: DNA
<213> ORGANISM: Artificial Sequence
<220> FEATURE:
<223> OTHER INFORMATION: Forward primer 2Apro-F2

<400> SEQUENCE: 71 ccagggatt ccggtggcat t                                     21

<210> SEQ ID NO 72
<211> LENGTH: 21
<212> TYPE: DNA
<213> ORGANISM: Artificial Sequence
<220> FEATURE:
<223> OTHER INFORMATION: Reverse primer 2Apro-R2

<400> SEQUENCE: 72
aatgccaccg gaatcccctg g                                    21

<210> SEQ ID NO 73
<211> LENGTH: 60
<212> TYPE: DNA
<213> ORGANISM: Artificial Sequence

```
<220> FEATURE:
<223> OTHER INFORMATION: Forward primer FBP1-F4

<400> SEQUENCE: 73
ggatcctaat acgactcact atagggaaca gccaccatgg cagactattc aacagtgcct    60

<210> SEQ ID NO 74
<211> LENGTH: 51
<212> TYPE: DNA
<213> ORGANISM: Artificial Sequence
<220> FEATURE:
<223> OTHER INFORMATION: Reverse primer FBP1-R4

<400> SEQUENCE: 74
ccagcacctc agggccaata aaaaaaaaaa aaaaaaaaa aaaaaaaaaa a             51

<210> SEQ ID NO 75
<211> LENGTH: 21
<212> TYPE: DNA
<213> ORGANISM: Artificial Sequence
<220> FEATURE:
<223> OTHER INFORMATION: Reverse primer FBP-R5

<400> SEQUENCE: 75
ttatcccatg ttccagttgc c                                              21

<210> SEQ ID NO 76
<211> LENGTH: 60
<212> TYPE: DNA
<213> ORGANISM: Artificial Sequence
<220> FEATURE:
<223> OTHER INFORMATION: Forward primer FBP1-F5

<400> SEQUENCE: 76
ggatcctaat acgactcact atagggaaca gccaccatgc cacctggtgg actacaggaa    60

<210> SEQ ID NO 77
<211> LENGTH: 21
<212> TYPE: DNA
<213> ORGANISM: Artificial Sequence
<220> FEATURE:
<223> OTHER INFORMATION: Reverse primer FBP1-R6

<400> SEQUENCE: 77
ttatatgagt tgccgagcat a                                              21

<210> SEQ ID NO 78
<211> LENGTH: 60
<212> TYPE: DNA
<213> ORGANISM: Artificial Sequence
<220> FEATURE:
<223> OTHER INFORMATION: Forward primer FBP1-F6

<400> SEQUENCE: 78
ggatcctaat acgactcact atagggaaca gccaccatga atgcagttca agaaatcatg    60

<210> SEQ ID NO 79
<211> LENGTH: 44
<212> TYPE: DNA
<213> ORGANISM: Artificial Sequence
<220> FEATURE:
<223> OTHER INFORMATION: Forward primer for amplifying T7-EV71 5'UTR
      linker region RNA

<400> SEQUENCE: 79
taatacgact cactataggg ccatccggtg tgcaacaggg caat                     44
```

-continued

```
<210> SEQ ID NO 80
<211> LENGTH: 21
<212> TYPE: DNA
<213> ORGANISM: Artificial Sequence
<220> FEATURE:
<223> OTHER INFORMATION: Reverse primer for amplifying T7-EV71 5'UTR
      linker region RNA

<400> SEQUENCE: 80
gtttgattgt gttgagggtc a                                              21

<210> SEQ ID NO 81
<211> LENGTH: 25
<212> TYPE: DNA
<213> ORGANISM: Artificial Sequence
<220> FEATURE:
<223> OTHER INFORMATION: sequence encoding shFBP1 shRNA

<400> SEQUENCE: 81
ccaagatttg ctgttggcat tgtaa                                          25

<210> SEQ ID NO 82
<211> LENGTH: 23
<212> TYPE: DNA
<213> ORGANISM: Artificial Sequence
<220> FEATURE:
<223> OTHER INFORMATION: sequence encoding scramble control (shNC) shRNA

<400> SEQUENCE: 82
aatttgcgcc cgcttaccca gtt                                            23

<210> SEQ ID NO 83
<211> LENGTH: 25
<212> TYPE: DNA
<213> ORGANISM: Artificial Sequence
<220> FEATURE:
<223> OTHER INFORMATION: sequence encoding shFBP2 shRNA

<400> SEQUENCE: 83
cacattcgta ttctgagatc cgtcc                                          25
```